United States Patent
Sakuma et al.

(10) Patent No.: US 8,648,208 B2
(45) Date of Patent: Feb. 11, 2014

(54) ACTIVATING AGENT FOR PEROXISOME PROLIFERATOR ACTIVATED RECEPTOR

(75) Inventors: Shogo Sakuma, Saitama (JP); Rie Takahashi, Saitama (JP); Hideki Nakamura, Saitama (JP)

(73) Assignee: Nippon Chemiphar Co. Ltd., Tokyo (JP)

( * ) Notice: Subject to any disclaimer, the term of this patent is extended or adjusted under 35 U.S.C. 154(b) by 46 days.

(21) Appl. No.: 12/937,986

(22) PCT Filed: Apr. 15, 2009

(86) PCT No.: PCT/JP2009/057946
§ 371 (c)(1),
(2), (4) Date: Dec. 15, 2010

(87) PCT Pub. No.: WO2009/128558
PCT Pub. Date: Oct. 22, 2009

(65) Prior Publication Data
US 2011/0098480 A1 Apr. 28, 2011

(30) Foreign Application Priority Data
Apr. 15, 2008 (JP) ................. 2008-105899

(51) Int. Cl.
*C07D 209/12* (2006.01)
*C07D 209/18* (2006.01)
*A61K 31/405* (2006.01)

(52) U.S. Cl.
USPC ............... 548/494; 548/400; 514/415

(58) Field of Classification Search
USPC ................. 548/400, 494; 514/415
See application file for complete search history.

(56) References Cited

U.S. PATENT DOCUMENTS

| | | | |
|---|---|---|---|
| 4,956,379 A | 9/1990 | Meanwell | |
| 5,089,514 A | 2/1992 | Hulin | |
| 5,723,479 A | 3/1998 | Sohda et al. | |
| 6,043,264 A | 3/2000 | Ohtake et al. | |
| 6,300,364 B1 | 10/2001 | Shomikawa et al. | |
| 6,589,969 B1 | 7/2003 | Tajima et al. | |
| 6,787,552 B2 | 9/2004 | Sakuma et al. | |
| 7,078,422 B2 | 7/2006 | Sakuma et al. | |
| 7,119,104 B2 | 10/2006 | Sakuma et al. | |
| 7,265,137 B2 | 9/2007 | Sakuma et al. | |
| 2002/0032330 A1 | 3/2002 | Nomura et al. | |
| 2003/0109570 A1 | 6/2003 | Tsunoda et al. | |
| 2003/0171377 A1 | 9/2003 | Bigge et al. | |
| 2005/0080115 A1 | 4/2005 | Jeppesen et al. | |
| 2007/0155805 A1 | 7/2007 | Harling et al. | |
| 2008/0194564 A1 | 8/2008 | Zeiller et al. | |

FOREIGN PATENT DOCUMENTS

| | | |
|---|---|---|
| CA | 2457054 | 2/2003 |
| EP | 505322 | 9/1992 |
| EP | 558062 | 9/1993 |
| EP | 1184366 | 3/2002 |
| EP | 1310494 | 5/2003 |
| JP | 2003-292439 | 10/2003 |
| WO | WO 92/10468 | 6/1992 |
| WO | WO 96/20935 | 7/1996 |
| WO | WO 96/35688 | 11/1996 |
| WO | WO 97/27190 | 7/1997 |
| WO | WO 97/28115 | 8/1997 |
| WO | WO 01/00603 | 1/2001 |
| WO | WO 01/16120 | 3/2001 |
| WO | WO 01/40207 | 6/2001 |
| WO | WO 01/79197 | 10/2001 |
| WO | WO 02/50048 | 6/2002 |
| WO | WO 02/059098 | 8/2002 |
| WO | WO 02/67912 | 9/2002 |
| WO | WO 02/092590 | 11/2002 |
| WO | WO 03/018553 | 3/2003 |
| WO | WO 03/099793 | 12/2003 |
| WO | WO 2004/007439 | 1/2004 |
| WO | WO 2004/018475 | 3/2004 |
| WO | WO 2004/022551 | 3/2004 |
| WO | WO 2004/063166 | 7/2004 |
| WO | WO 2004/063184 | 7/2004 |
| WO | WO 2004/063190 | 7/2004 |
| WO | WO 2004/071509 | 8/2004 |
| WO | WO 2005/049578 | 6/2005 |
| WO | WO 2005/054213 | 6/2005 |
| WO | WO 2005/077926 | 8/2005 |
| WO | WO 2005/115384 | 12/2005 |
| WO | WO 2006/125324 | * 11/2006 |
| WO | WO 2007/004733 | 1/2007 |
| WO | WO 2007/119887 | 10/2007 |
| WO | WO 2008/016175 | 2/2008 |

OTHER PUBLICATIONS

Kidwai, Acta Pharmaceutica, 47(1):53-57 (1997).*

(Continued)

*Primary Examiner* — Yong Chu
*Assistant Examiner* — Sonya Wright
(74) *Attorney, Agent, or Firm* — Jones Day

(57) ABSTRACT

A compound represented by the formula (I) or a pharmacologically acceptable salt thereof is used as an activator of PPAR (I)

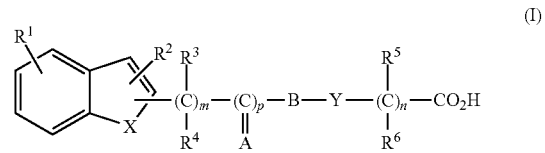

wherein each of $R^1$ and $R^2$ is hydrogen, $C_{1-8}$ alkyl, $C_{1-8}$ alkyl substituted with halogen, or the like; each of $R^3$, $R^4$, $R^5$, and $R^6$ is hydrogen, $C_{1-8}$ alkyl, or the like; X is sulfur or the like; Y is oxygen, a bond, or the like; p is 0 or 1; A is oxygen, $CH_2$, $N-NH_2$, or the like; when p is 1, B is phenyl, which can have a substituent; when p is 0, B is a condensed ring such as benzisoxazole, which can have a substituent; m is an integer of 1 to 4; and n is an integer of 0 to 5.

22 Claims, No Drawings

(56) References Cited

OTHER PUBLICATIONS

Berger, J. et al., 1999, *J Biol Chem* 274:6718-6725.
Bright, S. et al., 1997, *J. Immunol Methods* 207(1):23-31.
He, T.-C. et al., 1999, *Cell* 99:335-345.
Isseman, I. et al., 1990, *Nature* 347:645-650.
Kidwai et al., *Acta Pharmaceutica* (Zagreb), 47(1):53-57 (1997).
Kliewer et al., *Nature* 358:771-774 (1992).
Kliewer et al., *Proc Natl Acad Sci USA* 91:7335-7359 (1994).
Kuwabara et al., J Pmarmacol Exp Ther 309(3):970-977 (2004).
Lehmann, J. et al., 1997, *J Biol Chem* 272(6):3406-3410.
Mano H., et al., 2000, *J Biol Chem* 175:8126-8132.
Pilli et al., Archiv der Pharmazie 326(9):559-561, 1993.
Oliver, W. et al., 2001, *Proc Natl Acad Sci USA* 98(9):5306-5311.
Sznaidman et al. Bioorg Med Chem Lett 13:1517-1521, 2003.
Uhle & Harris, *J Am Chem Society* 79:102-109 (1957).
Office Action dated Nov. 3, 2006 for U.S. Appl. No. 10/486,783.
Office Action dated Apr. 3, 2007 for U.S. Appl. No. 11/544,505.
Office Action dated Sep. 17, 2007 for U.S. Appl. No. 11/544,505.
Advisory Action dated Jan. 4, 2008 for U.S. Appl. No. 11/544,505.
Office Action dated May 20, 2011 for U.S. Appl. No. 12/297,436.
Office Action dated Jan. 10, 2012 for U.S. Appl. No. 12/297,436.
Advisory Action dated May 16, 2012 for U.S. Appl. No. 12/297,436.
Office Action dated Feb. 4, 2009 for U.S. Appl. No. 11/888,492.
Office Action dated Mar. 25, 2009 for U.S. Appl. No. 11/888,493.

\* cited by examiner

ACTIVATING AGENT FOR PEROXISOME PROLIFERATOR ACTIVATED RECEPTOR

This application is a national stage under 35 U.S.C. 371 of the International Application No. PCT/JP2009/057946, filed on Apr. 15, 2009, which claims the benefit of the Japanese Application No. 2008-105899, filed on Apr. 15, 2008, the content of which is incorporated herein by reference in its entirety.

TECHNICAL FIELD

The present invention relates to an activator of peroxisome proliferator activated receptor (PPAR).

PRIOR ART

As the activator of peroxisome proliferator activated receptor (PPAR), three subtypes, namely PPARα, PPARγ and PPARδ have been identified (Non-Patent document 1: Proc. Natl. Acad. Sci. USA, 91, p 7335-7359, 1994).

Various compounds have been reported with respect to functions of activating transcription of the PPAR subtypes, lowering blood sugar level, or improving metabolism of lipid.

For example, WO 01/000603 (Patent Document 1) reports that GW-501516 (GSK) represented by the following formula has been developed as an agent for improving metabolism of lipid.

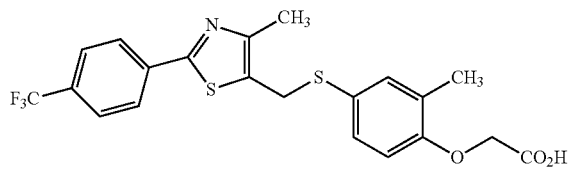 [SMILES: Cc1cc(SCc2sc(-c3ccc(C(F)(F)F)cc3)nc2C)ccc1OCC(=O)O]

WO 2005/077926 (Patent Document 2) discloses the following compound, in which the thiazole ring of GW-501516 is replaced with a benzothiophene ring or a benzofuran ring.

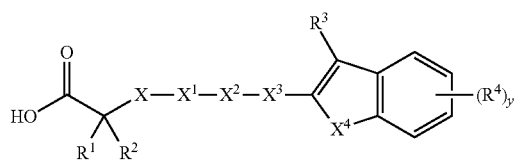

The present inventors have found that the following compound disclosed in WO 2005/090920 (Patent Document 3) and the compounds disclosed in Patent Documents 4-10 have a function of activating transcription of PPAR.

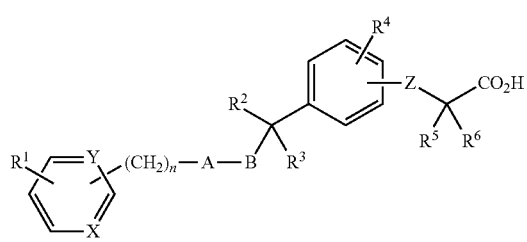

Patent Document 4: WO 02/014291
Patent Document 5: WO 02/076957
Patent Document 6: WO 03/016291
Patent Document 7: WO 03/033493
Patent Document 8: WO 2007/004733
Patent Document 9: WO 2007/119887
Patent Document 10: WO 2008/016175

In the compound disclosed in Patent Document 2, the linker between the benzothiophene ring and the phenoxyacetic acid is an alkylene chain interrupted with sulfur or oxygen atom ($X^2$), while the alkylene chain is not interrupted in the compound of the present invention represented by the below-described formula (I). In this regard, the compound of the present invention is distinct from the compound disclosed in Patent Document 2.

The linker in the compound of the present invention is also different from that of GW-501516 in the same manner as in the difference between the compound of the present invention and the compound disclosed in Patent Document 2. Further, the condensed ring such as benzothiophene ring contained in the compound of the present invention is replaced with the thiazole ring in GW-501516.

Turning to the compounds disclosed in Patent Documents 3-10, A in the compound disclosed in Patent Document 3 is a monocyclic ring such as pyrazole, thiophene, furan, pyrrole, while the compound of the present invention has a condensed ring such as benzothiophene ring. The compounds disclosed in Patent Documents 4-10 also has a monocyclic ring corresponding to A of the compound disclosed in Patent Document 3.

As is described above, there are clear structural differences between the compound of the present invention and the above-mentioned compounds disclosed in the prior art documents.

DISCLOSURE OF INVENTION

An object of the invention is to provide a compound represented by the formula (I), (II), or (III) or a pharmacologically acceptable salt thereof, which has a function of activating peroxisome proliferator activated receptor.

The present invention resides in a compound having the following formula (I) or a pharmacologically acceptable salt thereof:

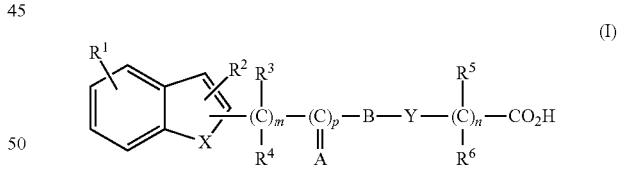

(I)

wherein $R^1$ is hydrogen, halogen, hydroxyl, nitro, amino, cyano, carboxyl, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, a heterocyclic group of five-membered or six-membered ring, aralkyl consisting of $C_{6-10}$ aryl and $C_{1-8}$ alkylene, or $C_{1-8}$ alkyl substituted with a heterocyclic group of five-membered or six-membered ring;

$R^2$ is hydrogen, $C_{1-8}$ alkyl, $C_{2-8}$ alkenyl, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{2-8}$ acyl, $C_{6-10}$ aryl, or aralkyl consisting of $C_{6-10}$ aryl and $C_{1-8}$ alkylene;

each of $R^3$, $R^4$, $R^5$, and $R^6$ independently is hydrogen, $C_{1-8}$ alkyl, or $C_{1-8}$ alkyl substituted with halogen;

X is oxygen, sulfur, or $NR^7$, wherein $R^7$ is hydrogen, $C_{1-8}$ alkyl, $C_{1-8}$ alkyl substituted with halogen, aralkyl consisting of $C_{6-10}$ aryl and $C_{1-8}$ alkylene, $C_{2-8}$ acyl, or $C_{2-8}$ alkenyl;

Y is oxygen, sulfur, $NR^8$, or a bond, wherein $R^8$ is hydrogen, $C_{1-8}$ alkyl, $C_{1-8}$ alkyl substituted with halogen, $C_{2-8}$ acyl, or $C_{2-8}$ alkenyl;

p is 0 or 1;

A is oxygen, $CH_2$, N—$NH_2$, or N—$OR^9$, wherein $R^9$ is hydrogen, $C_{1-8}$ alkyl, $C_{1-8}$ alkyl substituted with halogen, $C_{2-8}$ acyl, $C_{2-8}$ alkenyl, or aralkyl consisting of $C_{6-10}$ aryl and $C_{1-8}$ alkylene;

when p is 1, B is phenyl, which can have a substituent selected from the group consisting of halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene;

when p is 0, B is a condensed ring selected from the group consisting of indole, benzofuran, benzisoxazole, or 1,2-benzisothiazole, each of which can have a substituent selected from the group consisting of halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene, wherein Y binds to the benzene ring of B, and —(C($R^3$)($R^4$))m- binds to the condensed ring at the 3-position of B;

m is an integer of 1 to 4;

n is an integer of 0 to 5; and when n is 0, Y is a bond.

The invention also resides in a compound having the following formula (II) or a pharmacologically acceptable salt thereof:

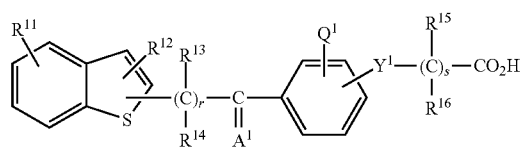

(II)

wherein $R^{11}$ is hydrogen, halogen, hydroxyl, nitro, amino, cyano, carboxyl, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, a heterocyclic group of five-membered or six-membered ring, aralkyl consisting of $C_{6-10}$ aryl and $C_{1-8}$ alkylene, or $C_{1-8}$ alkyl substituted with a heterocyclic group of five-membered or six-membered ring;

$R^{12}$ is hydrogen, $C_{1-8}$ alkyl, $C_{2-8}$ alkenyl, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{2-8}$ acyl, $C_{6-10}$ aryl, or aralkyl consisting of $C_{6-10}$ aryl and $C_{1-8}$ alkylene;

each of $R^{13}$, $R^{14}$, $R^{15}$, and $R^{16}$ independently is hydrogen, $C_{1-8}$ alkyl, or $C_{1-8}$ alkyl substituted with halogen;

$Y^1$ is oxygen, sulfur, $NR^{18}$, or a bond, wherein $R^{18}$ is hydrogen, $C_{1-8}$ alkyl, $C_{1-8}$ alkyl substituted with halogen, $C_{2-8}$ acyl, or $C_{2-8}$ alkenyl;

$A^1$ is oxygen, $CH_2$, N—$NH_2$, or N—$OR^{19}$, wherein $R^{19}$ is hydrogen, $C_{1-8}$ alkyl, $C_{1-8}$ alkyl substituted with halogen, $C_{2-8}$ acyl, $C_{2-8}$ alkenyl, or aralkyl consisting of $C_{6-10}$ aryl and $C_{1-8}$ alkylene;

$Q^1$ is hydrogen, halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene;

r is an integer of 1 to 4; and s is an integer of 1 to 5.

The invention further resides in a compound having the following formula (III) or a pharmacologically acceptable salt thereof:

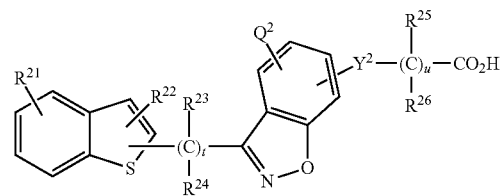

(III)

wherein $R^{21}$ is hydrogen, halogen, hydroxyl, nitro, amino, cyano, carboxyl, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, a heterocyclic group of five-membered or six-membered ring, aralkyl consisting of $C_{6-10}$ aryl and $C_{1-8}$ alkylene, or $C_{1-8}$ alkyl substituted with a heterocyclic group of five-membered or six-membered ring;

$R^{22}$ is hydrogen, $C_{1-8}$ alkyl, $C_{2-8}$ alkenyl, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{2-8}$ acyl, $C_{6-10}$ aryl, or aralkyl consisting of $C_{6-10}$ aryl and $C_{1-8}$ alkylene;

each of $R^{23}$, $R^{24}$, $R^{25}$, and $R^{26}$ independently is hydrogen, $C_{1-8}$ alkyl, or $C_{1-8}$ alkyl substituted with halogen;

$Y^2$ is oxygen, sulfur, $NR^{18}$, or a bond, wherein $R^{28}$ is hydrogen, $C_{1-8}$ alkyl, $C_{1-8}$ alkyl substituted with halogen, $C_{2-8}$ acyl, or $C_{2-8}$ alkenyl;

$Q^2$ is hydrogen, halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene;

t is an integer of 1 to 4; and u is an integer of 1 to 5.

The invention also relates to an activator of peroxisome proliferator activated receptor δ which contains as an effective component a compound represented by the formula (I), (II), or (III), or a pharmacologically acceptable salt thereof.

The invention further relates to a medicament for treatment and/or prophylaxis of a disease mediated by peroxisome proliferator activated receptor which contains as an effective component a compound represented by the formula (I), (II), or (III), or a pharmacologically acceptable salt thereof.

BEST EMBODIMENTS OF INVENTION

The present invention is described below in more detail.

In the formula (I), $R^1$, $R^2$, $R^3$, $R^4$, $R^5$, $R^6$, $R^7$, $R^8$, $R^9$, and a substituent of phenyl or a condensed ring represented by B can be $C_{1-8}$ alkyl. Examples of the $C_{1-8}$ alkyl include methyl, ethyl, propyl, isopropyl, butyl, isobutyl, t-butyl, pentyl, and hexyl.

$R^1$, $R^2$, $R^7$, $R^8$, $R^9$, and a substituent of phenyl or a condensed ring represented by B can be $C_{2-8}$ alkenyl. Examples of the $C_{2-8}$ alkenyl include vinyl and allyl.

$R^1$ and a substituent of phenyl or a condensed ring represented by B can be $C_{2-8}$ alkynyl. Examples of the $C_{2-8}$ alkynyl include propargyl.

$R^1$ and a substituent of phenyl or a condensed ring represented by B can be cycloalkyl of three-membered to seven-membered ring. Examples of the cycloalkyl of three-membered to seven-membered ring include cyclopropyl, cyclopentyl, and cyclohexyl.

$R^1$ and a substituent of phenyl or a condensed ring represented by B can be $C_{1-8}$ alkoxy. Examples of the $C_{1-8}$ alkoxy include methoxy, ethoxy, propoxy, isopropoxy, butoxy, isobutoxy, t-butoxy, pentyloxy, and hexyloxy.

$R^1$ and a substituent of phenyl or a condensed ring represented by B can be halogen. Examples of the halogen include fluorine, chlorine, and bromine.

$R^1$, $R^2$, $R^3$, $R^4$, $R^5$, $R^6$, $R^7$, $R^8$, $R^9$, and a substituent of phenyl or a condensed ring represented by B can be $C_{1-8}$ alkyl substituted with halogen. Examples of the $C_{1-8}$ alkyl substituted with halogen include methyl, ethyl, propyl, isopropyl, butyl, and t-butyl which are substituted with 1-3 halogens such as fluorine, chlorine, and bromine. Preferred are trifluoromethyl, chloromethyl, 2-chloroethyl, 2-bromoethyl, and 2-fluoroethyl.

$R^1$, $R^2$, and a substituent of phenyl or a condensed ring represented by B can be $C_{1-8}$ alkyl substituted with $C_{1-8}$ alkoxy. Examples of the $C_{1-8}$ alkyl substituted with $C_{1-8}$ alkoxy include methyl, ethyl, propyl, isopropyl, butyl, isobutyl, t-butyl, pentyl, and hexyl which are substituted with methoxy, ethoxy, propoxy, isopropoxy, butoxy, isobutoxy, t-butoxy, pentyloxy, or hexyloxy. Preferred is ethoxyethyl.

$R^1$ and a substituent of phenyl or a condensed ring represented by B can be $C_{1-8}$ alkoxy substituted with halogen. Examples of the $C_{1-8}$ alkoxy substituted with halogen include methoxy, ethoxy, propoxy, isopropoxy, butoxy, and t-butoxy which are substituted with 1-3 halogen atoms such as fluorine atom, chlorine atom, or bromine atom. Preferred are trifluoromethoxy, chloromethoxy, 2-chloroethoxy, 2-bromoethoxy, and 2-fluoroethoxy.

$R^1$, $R^2$, and a substituent of phenyl or a condensed ring represented by B can be $C_{6-10}$ aryl. Examples of the $C_{6-10}$ aryl include phenyl.

$R^1$, $R^2$, $R^7$, $R^8$, $R^9$, and a substituent of phenyl or a condensed ring represented by B can be $C_{2-8}$ acyl. Examples of the $C_{2-8}$ acyl include acetyl.

$R^1$ and a substituent of phenyl or a condensed ring represented by B can be a five-membered or six-membered heterocyclic group. Examples of the five-membered or six-membered heterocyclic group include pyridyl.

$R^1$, $R^2$, and a substituent of phenyl or a condensed ring represented by B can be $C_{1-8}$ alkyl substituted with cycloalkyl of three-membered to seven-membered ring. Examples of the $C_{1-8}$ alkyl substituted with cycloalkyl of three-membered to seven-membered ring include methyl, ethyl, propyl, isopropyl, butyl, isobutyl, t-butyl, pentyl, and hexyl that are substituted with cyclopropyl, cyclopentyl, or cyclohexyl.

$R^1$, $R^2$, $R^7$, $R^9$, and a substituent of phenyl or a condensed ring represented by B can be aralkyl consisting of $C_{6-10}$ aryl and $C_{1-8}$ alkylene. Examples of the aralkyl include benzyl and, phenethyl.

$R^1$ can be $C_{1-8}$ alkyl substituted with a heterocyclic group of five-membered or six-membered ring. Examples of the $C_{1-8}$ alkyl substituted with a heterocyclic group of five-membered or six-membered ring include methyl, ethyl, propyl, isopropyl, butyl, isobutyl, t-butyl, pentyl, and hexyl that are substituted with pyridyl.

$R^1$ (except for hydrogen) and a substituent of phenyl or a condensed ring represented by B can be present as 1 to 3 groups, two of which can be different from each other.

$R^1$ can also be dialkylamino. Examples of dialkylamino include dimethylamino and diethylamino. $R^2$ can also be cycloalkyl of three-membered to seven-membered ring. Examples of the cycloalkyl of three-membered to seven-membered ring include cyclopropyl, cyclopentyl, and cyclohexyl.

$R^1$ preferably is a group or an atom other than hydrogen, and $R^2$ preferably is $C_{2-6}$ alkyl.

In the formula (II), $R^{11}$, $R^{12}$, $R^{13}$, $R^{14}$, $R^{15}$, $R^{16}$, $R^{18}$, $R^{19}$, and $Q^1$ can be $C_{1-8}$ alkyl. Examples of the $C_{1-8}$ alkyl include methyl, ethyl, propyl, isopropyl, butyl, isobutyl, t-butyl, pentyl, and hexyl.

$R^{11}$, $R^{12}$, $R^{18}$, $R^{19}$, and $Q^1$ can be $C_{2-8}$ alkenyl. Examples of the $C_{2-8}$ alkenyl include vinyl and allyl.

$R^{11}$ and $Q^1$ can be $C_{2-8}$ alkynyl. Examples of the $C_{2-8}$ alkynyl include propargyl.

$R^{11}$ and $Q^1$ can be cycloalkyl of three-membered to seven-membered ring. Examples of the cycloalkyl of three-membered to seven-membered ring include cyclopropyl, cyclopentyl, and cyclohexyl.

$R^{11}$ and $Q^1$ can be $C_{1-8}$ alkoxy. Examples of the $C_{1-8}$ alkoxy include methoxy, ethoxy, propoxy, isopropoxy, butoxy, isobutoxy, t-butoxy, pentyloxy, and hexyloxy.

$R^{11}$ and $Q^1$ can be halogen. Examples of the halogen include fluorine, chlorine, and bromine.

$R^{11}$, $R^{12}$, $R^{13}$, $R^{14}$, $R^{15}$, $R^{16}$, $R^{18}$, $R^{19}$, and $Q^1$ can be $C_{1-8}$ alkyl substituted with halogen. Examples of the $C_{1-8}$ alkyl substituted with halogen include methyl, ethyl, propyl, isopropyl, butyl, and t-butyl that are substituted with 1-3 halogens such as fluorine, chlorine, and bromine. Preferred are trifluoromethyl, chloromethyl, 2-chloroethyl, 2-bromoethyl, and 2-fluoroethyl.

$R^{11}$, $R^{12}$, and $Q^1$ can be $C_{1-8}$ alkyl substituted with $C_{1-8}$ alkoxy. Examples of the $C_{1-8}$ alkyl substituted with $C_{1-8}$ alkoxy include methyl, ethyl, propyl, isopropyl, butyl, isobutyl, t-butyl, pentyl, and hexyl which are substituted with methoxy, ethoxy, propoxy, isopropoxy, butoxy, isobutoxy, t-butoxy, pentyloxy, or hexyloxy. Preferred is ethoxyethyl.

$R^{11}$ and $Q^1$ can be $C_{1-8}$ alkoxy substituted with halogen. Examples of the $C_{1-8}$ alkoxy substituted with halogen include methoxy, ethoxy, propoxy, isopropoxy, butoxy, and t-butoxy that are substituted with 1-3 halogen atoms such as fluorine atom, chlorine atom, or bromine atom. Preferred are trifluoromethoxy, chloromethoxy, 2-chloroethoxy, 2-bromoethoxy, and 2-fluoroethoxy.

$R^{11}$, $R^{12}$, and $Q^1$ can be $C_{6-10}$ aryl. Examples of the $C_{6-10}$ aryl include phenyl.

$R^{11}$, $R^{12}$, $R^{18}$, $R^{19}$, and $Q^1$ can be $C_{2-8}$ acyl. Examples of the $C_{2-8}$ acyl include acetyl.

$R^{11}$ can be a five-membered or six-membered heterocyclic group. Examples of the five-membered or six-membered heterocyclic group include pyridyl.

$R^{11}$, $R^{12}$, and $Q^1$ can be $C_{1-8}$ alkyl substituted with cycloalkyl of three-membered to seven-membered ring. Examples of the $C_{1-8}$ alkyl substituted with cycloalkyl of three-membered to seven-membered ring include methyl, ethyl, propyl, isopropyl, butyl, isobutyl, t-butyl, pentyl, and hexyl that are substituted with cyclopropyl, cyclopentyl, or cyclohexyl.

$R^{11}$, $R^{12}$, $R^{19}$, and $Q^1$ can be aralkyl consisting of $C_{6-10}$ aryl and $C_{1-8}$ alkylene. Examples of the aralkyl include benzyl and phenethyl.

$R^{11}$ can be $C_{1-8}$ alkyl substituted with a heterocyclic group of five-membered or six-membered ring. Examples of the $C_{1-8}$ alkyl substituted with a heterocyclic group of five-membered or six-membered ring include methyl, ethyl, propyl, isopropyl, butyl, isobutyl, t-butyl, pentyl, and hexyl that are substituted with pyridyl.

$R^{11}$ (except for hydrogen) and $Q^1$ can be present as 1 to 3 groups, two of which can be different from each other.

In the formula (III), $R^{21}$, $R^{22}$, $R^{23}$, $R^{24}$, $R^{25}$, $R^{26}$, $R^{28}$, and $Q^2$ can be $C_{1-8}$ alkyl. Examples of the $C_{1-8}$ alkyl include methyl, ethyl, propyl, isopropyl, butyl, isobutyl, t-butyl, pentyl, and hexyl.

$R^{21}$, $R^{22}$, $R^{28}$, $Q^2$ can be $C_{2-8}$ alkenyl. Examples of the $C_{2-8}$ alkenyl include vinyl and allyl.

$R^{21}$ and $Q^2$ can be $C_{2-8}$ alkynyl. Examples of the $C_{2-8}$ alkynyl include propargyl.

$R^{21}$ and $Q^2$ can be cycloalkyl of three-membered to seven-membered ring. Examples of the cycloalkyl of three-membered to seven-membered ring include cyclopropyl, cyclopentyl, and cyclohexyl.

$R^{21}$ and $Q^2$ can be $C_{1-8}$ alkoxy. Examples of the $C_{1-8}$ alkoxy include methoxy, ethoxy, propoxy, isopropoxy, butoxy, isobutoxy, t-butoxy, pentyloxy, and hexyloxy.

$R^{21}$ and $Q^2$ can be halogen. Examples of the halogen include fluorine, chlorine, and bromine.

$R^{21}$, $R^{22}$, $R^{23}$, $R^{24}$, $R^{25}$, $R^{26}$, $R^{28}$, and $Q^2$ can be $C_{1-8}$ alkyl substituted with halogen. Examples of the $C_{1-8}$ alkyl substituted with halogen include methyl, ethyl, propyl, isopropyl, butyl, and t-butyl that are substituted with 1-3 halogens such as fluorine, chlorine, and bromine. Preferred are trifluoromethyl, chloromethyl, 2-chloroethyl, 2-bromoethyl, and 2-fluoroethyl.

$R^{21}$, $R^{22}$, and $Q^2$ can be $C_{1-8}$ alkyl substituted with $C_{1-8}$ alkoxy. Examples of the $C_{1-8}$ alkyl substituted with $C_{1-8}$ alkoxy include methyl, ethyl, propyl, isopropyl, butyl, isobutyl, t-butyl, pentyl, and hexyl which are substituted with methoxy, ethoxy, propoxy, isopropoxy, butoxy, isobutoxy, t-butoxy, pentyloxy, or hexyloxy. Preferred is ethoxyethyl.

$R^{21}$ and $Q^2$ can be $C_{1-8}$ alkoxy substituted with halogen. Examples of the $C_{1-8}$ alkoxy substituted with halogen include methoxy, ethoxy, propoxy, isopropoxy, butoxy, and t-butoxy that are substituted with 1-3 halogen atoms such as fluorine atom, chlorine atom, or bromine atom. Preferred are trifluoromethoxy, chloromethoxy, 2-chloroethoxy, 2-bromoethoxy, and 2-fluoroethoxy.

$R^{21}$, $R^{22}$, and $Q^2$ can be $C_{6-10}$ aryl. Examples of the $C_{6-10}$ aryl include phenyl.

$R^{21}$, $R^{22}$, $R^{28}$, and $Q^2$ can be $C_{2-8}$ acyl. Examples of the $C_{2-8}$ acyl include acetyl.

$R^{21}$ can be a five-membered or six-membered heterocyclic group. Examples of the five-membered or six-membered heterocyclic group include pyridyl.

$R^{21}$, $R^{22}$ and $Q^2$ can be $C_{1-8}$ alkyl substituted with cycloalkyl of three-membered to seven-membered ring. Examples of the $C_{1-8}$ alkyl substituted with cycloalkyl of three-membered to seven-membered ring include methyl, ethyl, propyl, isopropyl, butyl, isobutyl, t-butyl, pentyl, and hexyl that are substituted with cyclopropyl, cyclopentyl, or cyclohexyl.

$R^{21}$, $R^{22}$, and $Q^2$ can be aralkyl consisting of $C_{6-10}$ aryl and $C_{1-8}$ alkylene. Examples of the aralkyl include benzyl and phenethyl.

$R^{21}$ can be $C_{1-8}$ alkyl substituted with a heterocyclic group of five-membered or six-membered ring. Examples of the $C_{1-8}$ alkyl substituted with a heterocyclic group of five-membered or six-membered ring include methyl, ethyl, propyl, isopropyl, butyl, isobutyl, t-butyl, pentyl, and hexyl that are substituted with pyridyl.

$R^{21}$ (except for hydrogen) and $Q^2$ can be present as 1 to 3 groups, two of which can be different from each other.

Preferred compounds of the present invention are shown below.

(1) A compound having the formula (II) or a pharmacologically acceptable salt thereof, wherein $R^{11}$ is hydrogen, $C_{1-8}$ alkyl, or $C_{1-8}$ alkyl substituted with halogen.

(2) A compound having the formula (II) or a pharmacologically acceptable salt thereof, wherein $R^{12}$ is $C_{1-8}$ alkyl or $C_{1-8}$ alkyl substituted with halogen.

(3) A compound having the formula (II) or a pharmacologically acceptable salt thereof, wherein each of $R^{13}$ and $R^{14}$ is hydrogen.

(4) A compound having the formula (II) or a pharmacologically acceptable salt thereof, wherein each of $R^{15}$ and $R^{16}$ independently is hydrogen or $C_{1-8}$ alkyl.

(5) A compound having the formula (II), or a pharmacologically acceptable salt thereof, wherein $Y^1$ is oxygen, $N(C_{1-8}$ alkyl), or a bond.

(6) A compound having the formula (II) or a pharmacologically acceptable salt thereof, wherein $A^1$ is oxygen, $CH_2$, N—OH, or N—O-benzyl.

(7) A compound having the formula (II) or a pharmacologically acceptable salt thereof, wherein $Q^1$ is $C_{1-8}$ alkyl or $C_{1-8}$ alkyl substituted with halogen.

(8) A compound having the formula (II) or a pharmacologically acceptable salt thereof, wherein r is 2.

(9) A compound having the formula (II) or a pharmacologically acceptable salt thereof, wherein s is 1 or 2.

(10) A compound having the formula (III) or a pharmacologically acceptable salt thereof, wherein $R^{21}$ is hydrogen, $C_{1-8}$ alkyl, or $C_{1-8}$ alkyl substituted with halogen.

(11) A compound having the formula (III) or a pharmacologically acceptable salt thereof, wherein $R^{22}$ is $C_{1-8}$ alkyl or alkyl substituted with halogen.

(12) A compound having the formula (III) or a pharmacologically acceptable salt thereof, wherein each of $R^{23}$ and $R^{24}$ is hydrogen.

(13) A compound or a pharmacologically acceptable salt thereof, wherein each of $R^{25}$ and $R^{26}$ independently is hydrogen or $C_{1-8}$ alkyl.

(14) A compound or a pharmacologically acceptable salt thereof, wherein $Y^2$ is oxygen, $N(C_{1-8}$ alkyl), or a bond.

(15) A compound or a pharmacologically acceptable salt thereof, wherein $Q^2$ is $C_{1-8}$ alkyl or $C_{1-8}$ alkyl substituted with halogen.

(16) A compound defined in claim 12 or a salt thereof, wherein t is 2.

(17) A compound defined in claim 12 or a pharmacologically acceptable salt thereof, wherein u is 1 or 2.

(18) A compound or a pharmacologically acceptable salt thereof, wherein the compound is selected from the group consisting of 2-methyl-4-[3-(3-methylbenzothiophen-2-yl)propionyl]phenoxyacetic acid, 2-methyl-2-[2-methyl-4-[3-(3-methylbenzothiophen-2-yl)propionyl]phenoxy]propionic acid, 2-methyl-4-[3-[3-methyl-5-(trifluoromethyl)-benzothiophen-2-yl]propionyl]phenoxyacetic acid, 2-methyl-2-[2-methyl-4-[3-[3-methyl-5-(trifluoromethyl)-benzothiophen-2-yl]propionyl]phenoxy]propionic acid, 2-methyl-4-[3-[3-methyl-6-(trifluoromethyl)benzothiophen-2-yl]propionyl]phenoxyacetic acid, 2-methyl-2-[2-methyl-4-[3-[3-methyl-6-(trifluoromethyl)benzothiophen-2-yl]propionyl]phenoxy]propionic acid, 3-[4-[3-[3-methyl-6-(trifluoromethyl)benzothiophen-2-yl]propionyl]-2-methylphenyl]propionic acid, 3-[4-[3-[3-ethyl-6-(trifluoromethyl)benzothiophen-2-yl]propionyl]-2-methylphenyl]propionic acid, 3-[2-methyl-4-[3-[3-propyl-6-(trifluoromethyl)benzothiophen-2-yl]propionyl]phenyl]propionic acid, 3-[2-methyl-4-[3-[3-butyl-6-(trifluoromethyl)benzothiophen-2-yl]propionyl]phenyl]propionic acid, 3-[2-methyl-4-[3-[3-isobutyl-6-(trifluoromethyl)benzothiophen-2-yl]propionyl]phenyl]propionic acid, 3-[2-methyl-4-[3-[3-isopropyl-6-(trifluoromethyl)benzothiophen-2-yl]propionyl]phenyl]propionic acid, 3-[4-[1-hydroxyimino-3-[3-isopropyl-6-(trifluoromethyl)benzothiophen-2-yl]propyl]-2-methylphenyl]propionic acid, 3-[4-[1-[2-[3-isopropyl-6-(trifluoromethyl)benzothiophen-2-yl]ethyl]vinyl]-2-methylphenyl]propionic acid, 4-[3-[3-isopropyl-6-(trifluoromethyl)benzothiophen-2-yl]propionyl]-2-methylphenoxyacetic acid, 4-[1-hydroxyimino-3-[3-isopropyl-6-(trifluoromethyl)benzothiophen-2-yl]propyl]-2-methylphenoxyacetic acid, 4-[3-[3-isopropyl-6-(trifluoromethyl)benzothiophen-2-yl]-1-methoxyiminopropyl]-2-methylphenoxyacetic acid, 4-[1-benzyloxyimino-3-[3-isopropyl-6-(trifluoromethyl)benzothiophen-2-yl]propyl]-2-methylphenoxyacetic acid, [3-[2-[3-isopropyl-6-(trifluoromethyl)benzothiophen-2-yl]ethyl]-5-methylbenzisoxazol-6-yloxy]acetic acid, N-[3-[2-[3-isopropyl-6-(trifluoromethyl)benzothiophen-2-yl]ethyl]-5-methylbenzisoxazol-6-yl]-N-methylglycine, and 3-[3-[2-[3-isopropyl-6-(trifluoromethyl)benzothiophen-2-yl]ethyl]-5-methylbenzisoxazol-6-yl]propionic acid.

(19) A compound or a pharmacologically acceptable salt thereof, wherein the compound is selected from the group consisting of 5-hydroxy-2-methyl-4-[3-[3-propyl-6-(trifluoromethyl)benzothiophen-2-yl]propionyl]phenoxyacetic acid, 5-hydroxy-4-[1-hydroxyimino-3-[3-propyl-6-(trifluoromethyl)benzothiophen-2-yl]propyl]-2-methylphenoxyacetic acid, N-[5-methyl-3-[2-[3-propyl-6-(trifluoromethyl)benzothiophen-2-yl]ethyl]benzisoxazol-6-yl]-N-methylglycine, [5-methyl-3-[2-[3-propyl-6-(trifluoromethyl)benzothiophen-2-yl]ethyl]benzisoxazol-6-yloxy]-acetic acid, 3-[5-methyl-3-[2-[3-propyl-6-(trifluoromethyl)benzothiophen-2-yl]ethyl]benzisoxazol-6-yl]propionic acid, 2-[3-[2-[3-isopropyl-6-(trifluoromethyl)-benzothiophen-2-yl]ethyl]-5-methylbenzisoxazol-6-yloxy]-propionic acid, and N-[3-[2-[3-isopropyl-6-(trifluoromethyl)benzothiophen-2-yl]ethyl]benzisoxazol-6-yl]-N-methylglycine.

The compound having the formula (I), (II), or (III) can be present in the form of a pharmacologically acceptable salt. Examples of the salt include an alkali metal salt, such as sodium salt, potassium salt and lithium salt.

The compound of the present invention can also be present in the form of an optical isomer such as enantiomer or racemic body, or a geometrical isomer such as cis or trans. These isomers are included in the scope of the present invention.

The synthesis scheme for preparing the compound of the formula (I) or (II) of the present invention are described below.

Synthetic Process 1 (Wherein Y is Oxygen in the Formula (I))

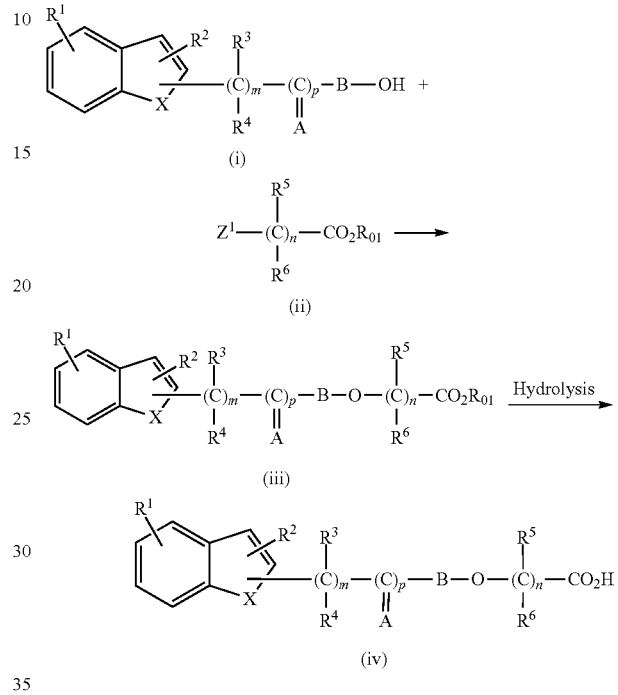

In the formulas, $Z^1$ is halogen such as bromine, $R^{01}$ is a lower alkyl such as ethyl, and each of $R^1$, $R^2$, $R^3$, $R^4$, $R^5$, $R^6$, X, p, A, B, m, and n are described above.

(a) The ester of the formula (iii) can be obtained by a reaction of the compound of the formula (i) with the compound of the formula (ii) in the presence of a base such as potassium carbonate in an inert solvent such as acetone.

(b) The compound of the present invention represented by the formula (iv) can be obtained by a reaction of the compound of the formula (iii) in the presence of lithium hydroxide in an inert solvent such as ethanol or methanol.

Synthetic Process 2 (Wherein the Combination of Y and $(C)_n(R^5)(R^6)$ is Ethylene in the Formula (I))

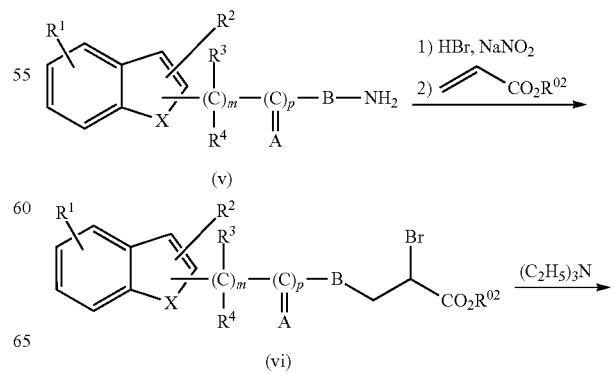

-continued

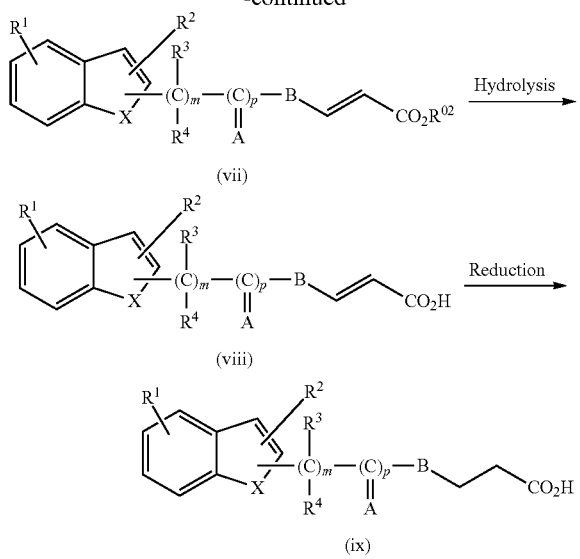

In the formulas, $R^{02}$ is a lower alkyl such as ethyl, and each of $R^1$, $R^2$, $R^3$, $R^4$, X, p, A, B, and m are described above.

(a) The compound of the formula (vi) can be obtained by subjecting the compound of the formula (v) to diazotization for example by using hydrobromic acid and sodium nitrite, and a reaction with an alkyl acrylate.

(b) The compound of the formula (vii) can be obtained by refluxing the compound of the formula (vi) while heating in the presence of a base such as triethylamine in an alcohol such as methanol.

(c) The compound of the formula (viii) can be obtained by subjecting the compound of the formula (vii) to a process analogous to the above-mentioned synthetic process 1(b).

(d) The compound of the present invention represented by the formula (ix) can be obtained by reducing the compound of the formula (viii) using hydrazine hydrate.

Synthetic Process 3 (Wherein Y is $NR^8$ in the Formula (I))

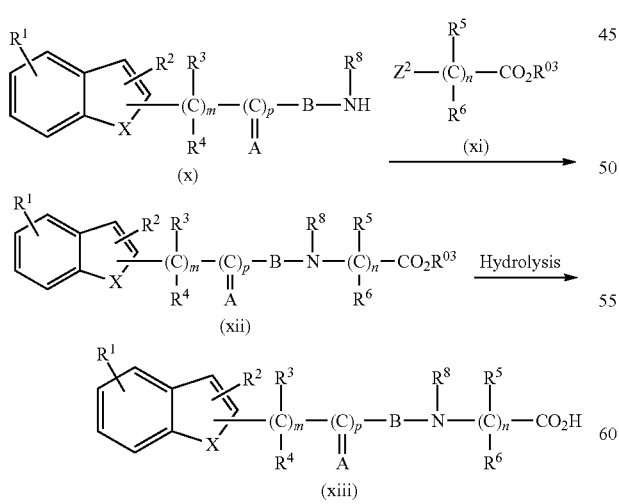

In the formulas, $Z^2$ is halogen such as bromine, $R^{03}$ is a lower alkyl such as ethyl, and each of $R^1$, $R^2$, $R^3$, $R^4$, $R^5$, $R^6$, $R^8$, X, p, A, B, m, and n are described above.

(a) The compound of the formula (xii) can be obtained by a reaction of the compound of the formula (x) with the compound of the formula (xi) in the presence of sodium hydride in a solvent such as DMF.

(b) The compound of the present invention represented by the formula (xiii) can be obtained by subjecting the compound of the formula (xii) to a process analogous to the above-mentioned synthetic process 1(b).

Synthetic Process 4 (Wherein $A^1$ is Oxygen, and $(C)_r(R^{13})(R^{14})$ is Ethylene in the Formula (II))

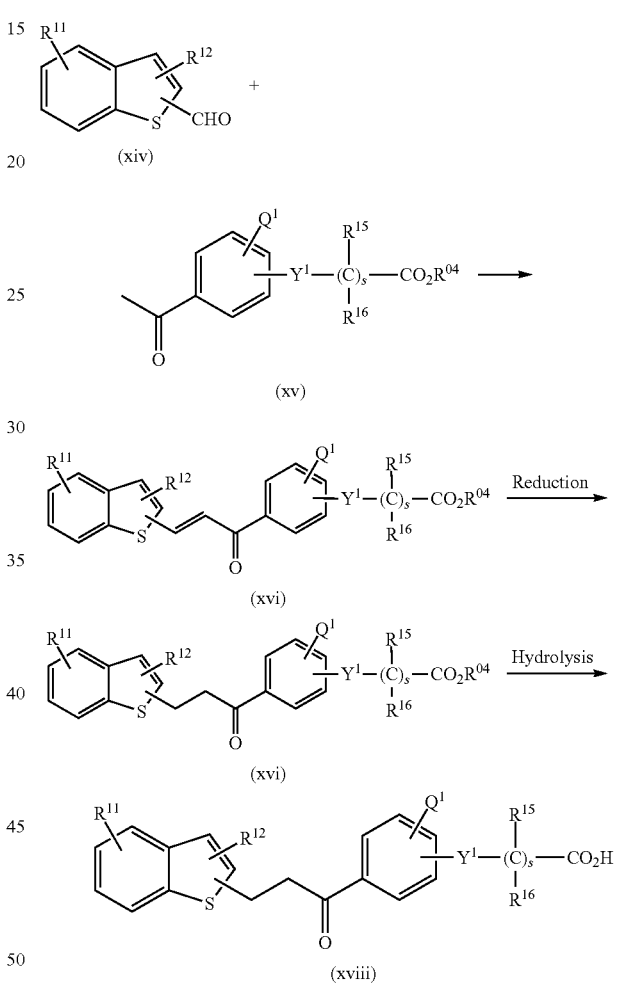

In the formulas, $R^{04}$ is a lower alkyl such as ethyl, and each of $R^{11}$, $R^{12}$, $R^{15}$, $R^{16}$, $Y^1$, $Q^1$, and s are described above.

(a) The compound of the formula (xvi) can be obtained by a reaction of the compound of the formula (xiv) with the compound of the formula (xv) in the presence of sodium methoxide in an inert solvent such as THF.

(b) The compound of the formula (xvii) can be obtained by subjecting the compound of the formula (xvi) to hydrogenation reduction in the presence of palladium-carbon.

(c) The compound of the present invention represented by the formula (xviii) can be obtained by subjecting the compound of the formula (xvii) to a process analogous to the above-mentioned synthetic process 1(b).

Synthetic Process 5 (wherein $A^1$ is N—OH in the Formula (II))

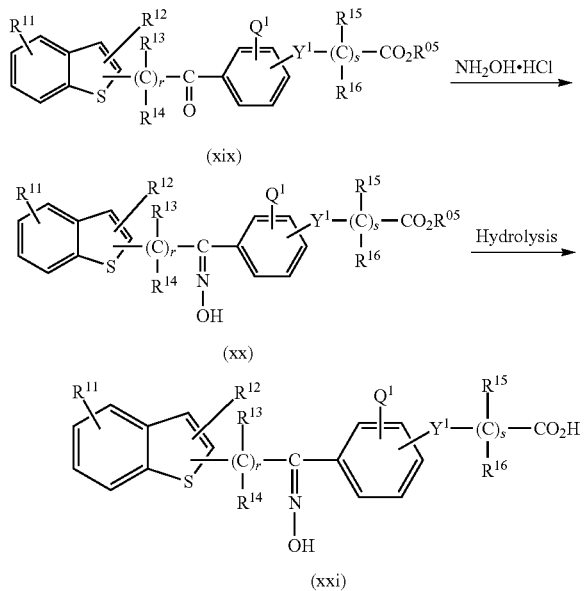

In the formulas, $R^{05}$ is a lower alkyl such as ethyl, and each of $R^{11}$, $R^{12}$, $R^{13}$, $R^{14}$, $R^{15}$, $R^{16}$, $Y^1$, $Q^1$, r, and s are described above.

(a) The compound of the formula (xx) can be obtained by a reaction of the compound of the formula (xix) with hydrochloric salt of hydroxylamine.

(b) The compound of the present invention represented by the formula (xxi) can be obtained by subjecting the compound of the formula (xx) to a process analogous to the above-mentioned synthetic process 1(b).

Synthetic Process 6 (Wherein $A^1$ is $CH_2$ in the Formula (II))

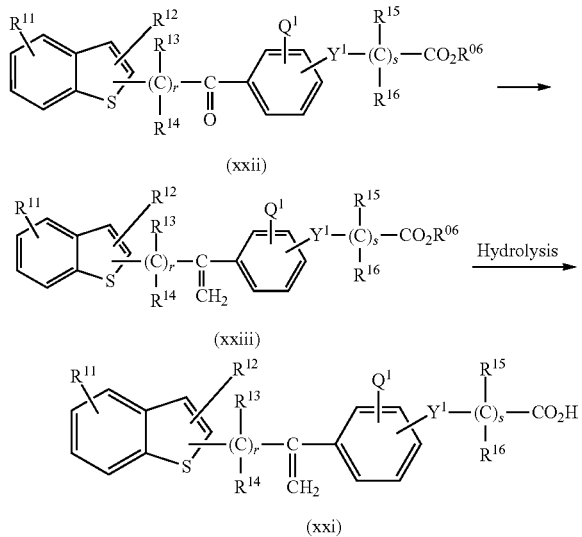

In the formulas, $R^{06}$ is a lower alkyl such as ethyl, and each of $R^{11}$, $R^{12}$, $R^{13}$, $R^{14}$, $R^{15}$, $R^{16}$, $Y^1$, $Q^1$, r, and s are described above.

(a) The compound of the formula (xxiii) can be obtained by a reaction of the compound of the formula (xxii) with trimethylphosphonium bromide in the presence of sodium amide in a solvent such as THF.

(b) The compound of the present invention represented by the formula (xxiv) can be obtained by subjecting the compound of the formula (xxiii) to a process analogous to the above-mentioned synthetic process 1(b).

The compounds of the present invention of the formulas (I), (II), and (III) can be prepared referring to the above-mentioned synthetic processes, as well as the below-mentioned synthesis examples, and the synthesis examples described in the above-mentioned patent documents 1-10.

Examples of the compounds of the present invention are shown below.

Representative Compound 1

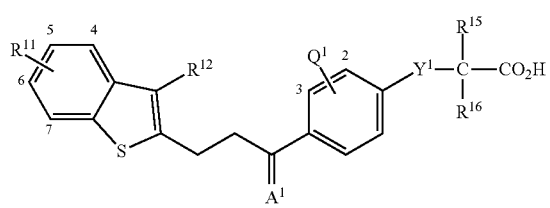

In the formula, $R^{11}$, $R^{12}$, $A^1$, $Q^1$, $Y^1$, $R^{15}$, and $R^{16}$ are set forth in Tables 1 to 3.

TABLE 1

| $R^{11}$ | $R^{12}$ | $A^1$ | $Q^1$ | $Y^1$ | $R^{15}/R^{16}$ |
|---|---|---|---|---|---|
| H | Methyl | O | 2-$CH_3$ | O | H/H |
| H | Methyl | O | 2-$CH_3$ | O | $CH_3$/$CH_3$ |
| 5-$CF_3$ | Methyl | O | 2-$CH_3$ | O | H/H |
| 5-$CF_3$ | Methyl | O | 2-$CH_3$ | O | $CH_3$/$CH_3$ |
| 6-$CF_3$ | Methyl | O | 2-$CH_3$ | O | H/H |
| 6-$CF_3$ | Methyl | O | 2-$CH_3$ | O | $CH_3$/$CH_3$ |
| 6-$CF_3$ | Isopropyl | O | 2-$CH_3$ | O | H/H |
| 6-$CF_3$ | Isopropyl | N—OH | 2-$CH_3$ | O | H/H |

TABLE 2

| $R^{11}$ | $R^{12}$ | $A^1$ | $Q^1$ | $Y^1$ | $R^{15}/R^{16}$ |
|---|---|---|---|---|---|
| 6-$CF_3$ | Isopropyl | N—O-Methyl | 2-$CH_3$ | O | H/H |
| 6-$CF_3$ | Isopropyl | N—O-Benzyl | 2-$CH_3$ | O | H/H |
| 6-$CF_3$ | Propyl | $CH_2$ | 3-$CH_3$ | O | H/H |
| 6-$CF_3$ | Hexyl | O | 2,5-$CH_3$ | S | H/H |
| 6-$CH_3$ | Hexyl | NOH | 2-$OCH_3$ | $NCH_3$ | H/H |
| 6-$CF_3$ | Hexyl | N—$NH_2$ | 2-Cl | N-Ethyl | H/H |
| 6-$CF_3$ | Cyclopropyl | O | 2,5-$CH_3$ | O | H/H |
| 6-Ethyl | Benzyl | O | 2,5-$CH_3$ | S | H/H |

TABLE 3

| $R^{11}$ | $R^{12}$ | $A^1$ | $Q^1$ | $Y^1$ | $R^{15}/R^{16}$ |
|---|---|---|---|---|---|
| 6-$OCF_3$ | Phenyl | O | 2,5-$CH_3$ | NH | H/H |
| 5,6-$OCH_3$ | $CH_2CH_2$—$OCH_3$ | O | 2,5-$CH_3$ | S | H/H |
| 7-$CF_3$ | Cyclohexyl | O | 2,5-$CH_3$ | O | H/H |
| 6-CN | Hexyl | O | 2,5-$CH_3$ | O | $CH_3$/$CH_3$ |
| 6-$NO_2$ | Hexyl | O | 2,5-$CH_3$ | O | H/H |

Representative Compound 2

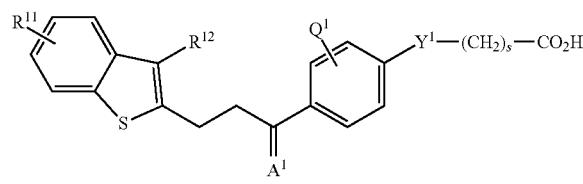

In the formula, $R^{11}$, $R^{12}$, $A^1$, $Q^1$, $Y^1$, and s are set forth in Tables 4 to 6.

TABLE 4

| $R^{11}$ | $R^{12}$ | $A^1$ | $Q^1$ | $Y^1$ | s |
|---|---|---|---|---|---|
| 6-CF$_3$ | Methyl | O | 2-CH$_3$ | Bond | 2 |
| 6-CF$_3$ | Ethyl | O | 2-CH$_3$ | Bond | 2 |
| 6-CF$_3$ | Propyl | O | 2-CH$_3$ | Bond | 2 |
| 6-CF$_3$ | Isopropyl | O | 2-CH$_3$ | Bond | 2 |
| 6-CF$_3$ | Isopropyl | N—OH | 2-CH$_3$ | Bond | 2 |
| 6-CF$_3$ | Isopropyl | CH$_2$ | 2-CH$_3$ | Bond | 2 |
| 6-CF$_3$ | Butyl | O | 2-CH$_3$ | Bond | 2 |

TABLE 5

| $R^{11}$ | $R^{12}$ | $A^1$ | $Q^1$ | $Y^1$ | s |
|---|---|---|---|---|---|
| 6-CF$_3$ | Isobutyl | O | 2-CH$_3$ | Bond | 2 |
| 6-CF$_3$ | Propyl | CH$_2$ | 2-CH$_3$ | Bond | 1 |
| 6-CF$_3$ | Hexyl | O | 2,5-CH$_3$ | Bond | 2 |
| 6-CH$_3$ | Hexyl | N—OH | 2-OCH$_3$ | Bond | 2 |
| 6-CF$_3$ | Hexyl | N—NH$_2$ | 2-Cl | Bond | 3 |
| 6-CF$_3$ | Cyclopropyl | O | 2,5-CH$_3$ | Bond | 1 |
| 6-Ethyl | Benzyl | O | 2,5-CH$_3$ | Bond | 1 |

TABLE 6

| $R^{11}$ | $R^{12}$ | $A^1$ | $Q^1$ | $Y^1$ | s |
|---|---|---|---|---|---|
| 6-OCF$_3$ | Phenyl | O | 2,5-CH$_3$ | Bond | 1 |
| 5,6-OH$_3$ | CH$_2$CH$_2$—OCH$_3$ | O | 2,5-CH$_3$ | Bond | 2 |
| 7-CF$_3$ | Cyclohexyl | O | 2,5-CH$_3$ | Bond | 2 |
| 6-CN | Hexyl | O | 2,5-CH$_3$ | Bond | 3 |
| 6-NO$_2$ | Hexyl | O | 2,5-CH$_3$ | Bond | 1 |

Representative Compound 3

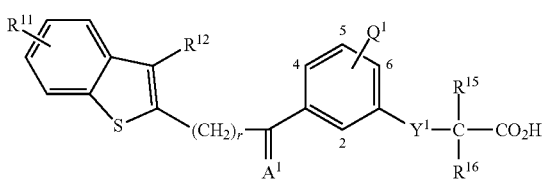

In the formula, $R^{11}$, $R^{12}$, r, $A^1$, $Q^1$, $Y^1$, $R^{15}$, and $R^{16}$ are set forth in Tables 7 and 8.

TABLE 7

| $R^{11}$ | $R^{12}$ | r | $A^1$ | $Q^1$ | $Y^1$ | $R^{15}/R^{16}$ |
|---|---|---|---|---|---|---|
| 5-CH$_3$ | Methyl | 2 | O | 6-CH$_3$ | O | H/H |
| 6-CH$_3$ | Methyl | 2 | O | 6-CH$_3$ | O | CH$_3$/CH$_3$ |
| 5-CF$_3$ | Propyl | 2 | O | 6-CH$_3$ | S | H/H |
| 6-CF$_3$ | Propyl | 3 | O | H | Bond | H/H |

TABLE 7-continued

| $R^{11}$ | $R^{12}$ | r | $A^1$ | $Q^1$ | $Y^1$ | $R^{15}/R^{16}$ |
|---|---|---|---|---|---|---|
| 6-CF$_3$ | Isopropyl | 3 | O | H | Bond | H/H |
| 6-OCF$_3$ | Hexyl | 3 | O | H | Bond | H/H |
| 6-CF$_3$ | Benzyl | 3 | CH$_2$ | H | Bond | H/H |
| 6-CF$_3$ | Methyl | 3 | O | 6-CH$_3$ | O | H/H |

TABLE 8

| $R^{11}$ | $R^{12}$ | r | $A^1$ | $Q^1$ | $Y^1$ | $R^{15}/R^{16}$ |
|---|---|---|---|---|---|---|
| 6-NO$_2$ | CH$_2$CH$_2$—OCH$_3$ | 3 | O | 6-Ethyl | NH | H/H |
| 6-NCH$_3$ | Benzyl | 3 | O | 6-CH$_3$ | Bond | H/H |
| 6-CF$_3$ | Ethyl | 3 | O | 3-Cl | Bond | H/H |
| 6-Ethyl | Propyl | 3 | O | 6-CH$_3$ | N—CH$_3$ | H/H |
| 6-CF$_3$ | Cyclopropyl | 4 | O | 6-CH$_3$ | Bond | H/H |
| 6-Phenyl | Isobutyl | 4 | O | 4-CH$_3$ | Bond | H/H |
| 6-CF$_3$ | Ethyl | 4 | N—OH | 4-CH$_3$ | Bond | H/H |
| 6-Cl | Propyl | 4 | N—OH | 4-CH$_3$ | Bond | H/H |

Representative Compound 4

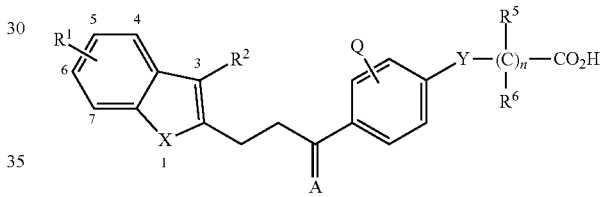

In the formula, X, $R^1$, $R^2$, A, Q, Y, n, $R^5$, and $R^6$ are set forth in Tables 9 and 10.

TABLE 9

| X | $R^1$ | $R^2$ | A | Q | Y | n | $R^5/R^6$ |
|---|---|---|---|---|---|---|---|
| O | 6-CF$_3$ | Hexyl | O | 2-CH$_3$ | O | 1 | CH$_3$/CH$_3$ |
| O | 6-CF$_3$ | Ethyl | O | 2-CH$_3$ | Bond | 2 | H/H |
| O | 6-CF$_3$ | Propyl | O | 2-CF$_3$ | Bond | 2 | H/H |
| O | 6-CH$_3$ | Propyl | O | H | N—CH$_3$ | 1 | H/H |
| O | 6-Ethyl | Isopropyl | O | H | NH | 1 | H/H |
| O | 6-CF$_3$ | Isopropyl | CH$_2$ | 2-CH$_3$ | Bond | 2 | H/H |
| O | 6-OCF$_3$ | Phenyl | O | 2-CH$_3$ | S | 1 | CH$_3$/CH$_3$ |
| O | 6-CF$_3$ | Isopropyl | N—OH | 2-Acetyl | Bond | 2 | H/H |

TABLE 10

| X | $R^1$ | $R^2$ | A | Q | Y | n | $R^5/R^6$ |
|---|---|---|---|---|---|---|---|
| O | 6-CF$_3$ | Isopropyl | N—OCH$_3$ | 2-CH$_3$ | Bond | 2 | H/H |
| NH | 6-CF$_3$ | Propyl | O | 2,5-CH$_3$ | O | 1 | CH$_3$/H |
| NH | 6-OCF$_3$ | Cyclopropyl | O | 2-CH$_3$ | Bond | 2 | H/Ethyl |
| NH | 5-CN | Isopropyl | N—OH | 2-CH$_3$ | Bond | 2 | H/H |
| NCH$_3$ | 6-CF$_3$ | Benzyl | O | 2-Ethyl | Bond | 2 | H/H |
| NCH$_3$ | 6-CF$_3$ | Isopropyl | O | 2-CH$_3$ | Bond | 2 | H/H |
| NCH$_3$ | 5-CF$_3$ | Isopropyl | N—OH | 2-OCH$_3$ | Bond | 2 | H/H |
| NCH$_3$ | 6-Cl | Isopropyl | O | 2-CH$_3$ | Bond | 2 | H/H |

Representative Compound 5

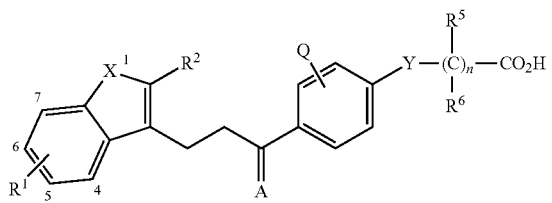

In the formula, X, $R^1$, $R^2$, A, Q, Y, n, $R^5$, and $R^6$ are set forth in Tables 11 to 13.

TABLE 11

| X | $R^1$ | $R^2$ | A | Q | Y | n | $R^5/R^6$ |
|---|---|---|---|---|---|---|---|
| O | 6-$CF_3$ | Methyl | O | 2-$CH_3$ | O | 1 | H/H |
| O | 6-$CF_3$ | Ethyl | O | 2-$CH_3$ | Bond | 2 | H/H |
| S | 6-$CF_3$ | Propyl | O | 2-$CH_3$ | Bond | 2 | H/H |
| S | 6-$CF_3$ | Isopropyl | O | 2-$CH_3$ | Bond | 2 | H/H |
| S | 5-$CF_3$ | Isopropyl | O | 2-$CH_3$ | Bond | 2 | H/H |
| O | 6-$CF_3$ | Propyl | O | 2-Allyl | Bond | 2 | H/H |

TABLE 12

| X | $R^1$ | $R^2$ | A | Q | Y | n | $R^5/R^6$ |
|---|---|---|---|---|---|---|---|
| S | 5,6-$CH_3$ | Hexyl | O | H | N—$CH_3$ | 1 | H/H |
| O | 6-$CF_3$ | Hexyl | O | 2-$CH_3$ | Bond | 2 | H/H |
| O | 6-$OCF_3$ | Isopropyl | O | 2-$CH_3$ | S | 1 | $CH_3$/$CH_3$ |
| O | 6-CN | Isopropyl | N—OH | 2-$OCH_3$ | Bond | 2 | H/H |
| O | 6-$CF_3$ | Isopropyl | N—$OCH_3$ | 2-$CH_3$ | Bond | 2 | H/H |
| NH | 6-$CF_3$ | Propyl | O | 2,5-$CH_3$ | NH | 1 | H/H |

TABLE 13

| X | $R^1$ | $R^2$ | A | Q | Y | n | $R^5/R^6$ |
|---|---|---|---|---|---|---|---|
| NH | 6-Ethyl | Isopropyl | O | 2-$CH_3$ | Bond | 2 | H/H |
| NH | 5-O-Ethyl | Isopropyl | N—OH | 2-$CH_3$ | Bond | 2 | H/H |
| $NCH_3$ | 6-$CF_3$ | Propyl | O | 2-Cl | Bond | 2 | H/H |
| $NCH_3$ | 6-$CF_3$ | Isopropyl | O | 2-Ethyl | Bond | 2 | H/H |
| $NCH_3$ | 5-$CF_3$ | Isopropyl | N—OH | 2-$CH_3$ | Bond | 2 | H/H |
| $NCH_3$ | 6-Cl | Isopropyl | O | 2-$CH_3$ | Bond | 2 | H/H |

Representative Compound 6

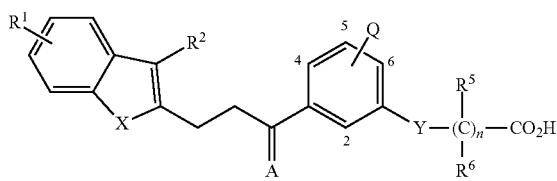

In the formula, X, $R^1$, $R^2$, A, Q, Y, n, $R^5$, and $R^6$ are set forth in Tables 14 and 15.

TABLE 14

| X | $R^1$ | $R^2$ | A | Q | Y | n | $R^5/R^6$ |
|---|---|---|---|---|---|---|---|
| O | 6-$CF_3$ | Methyl | O | 6-$CH_3$ | O | 1 | H/H |
| O | 6-$CF_3$ | Ethyl | O | 6-$CH_3$ | Bond | 2 | H/H |

TABLE 14-continued

| X | $R^1$ | $R^2$ | A | Q | Y | n | $R^5/R^6$ |
|---|---|---|---|---|---|---|---|
| O | 5,6-$CH_3$ | Propyl | O | H | N—$CH_3$ | 1 | H/H |
| O | 6-$CF_3$ | Propyl | O | 6-$CH_3$ | Bond | 2 | H/H |
| O | 6-$CH_3$ | Isopropyl | O | 6-Allyl | O | 1 | H/H |
| O | 6-Ethyl | Isopropyl | O | 6-$CH_3$ | Bond | 2 | H/H |
| O | 6-$CF_3$ | Isopropyl | O | 6-$CH_3$ | O | 1 | $CH_3$/$CH_3$ |
| O | 6-$OCF_3$ | Isopropyl | N—OH | 6-$CH_3$ | Bond | 2 | H/H |

TABLE 15

| X | $R^1$ | $R^2$ | A | Q | Y | n | $R^5/R^6$ |
|---|---|---|---|---|---|---|---|
| O | 6-$CF_3$ | Isopropyl | N—$OCH_3$ | 6-$CH_3$ | Bond | 2 | H/H |
| NH | 6-$OCF_3$ | Propyl | O | 2,6-$CH_3$ | O | 1 | H/H |
| NH | 6-$CF_3$ | Isopropyl | O | 6-$CH_3$ | Bond | 2 | H/Ethyl |
| NH | 5-$CF_3$ | Isopropyl | N—OH | 6-$CH_3$ | Bond | 2 | H/H |
| $NCH_3$ | 6-$CF_3$ | Propyl | O | 6-$CH_3$ | Bond | 2 | H/H |
| $NCH_3$ | 6-$CF_3$ | Isopropyl | O | 6-$CH_3$ | Bond | 2 | H/H |
| $NCH_3$ | 5-$CF_3$ | Isopropyl | N—OH | 6-$CH_3$ | Bond | 2 | H/H |
| $NCH_3$ | 6-Cl | Isopropyl | O | 6-$CH_3$ | Bond | 2 | H/H |

Representative Compound 7

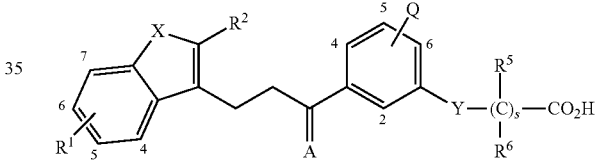

In the formula, X, $R^1$, $R^2$, A, Q, Y, s, $R^5$, and $R^6$ are set forth in Tables 16 and 17.

TABLE 16

| X | $R^1$ | $R^2$ | A | Q | Y | s | $R^5/R^6$ |
|---|---|---|---|---|---|---|---|
| O | 6-$CF_3$ | Methyl | O | 6-$CH_3$ | O | 1 | H/H |
| O | 6-$CF_3$ | Ethyl | O | 6-$CH_3$ | Bond | 2 | H/H |
| O | 6-$CF_2CF_3$ | Propyl | O | 6-$CH_3$ | Bond | 2 | H/H |
| O | 6-$OCF_3$ | Isopropyl | O | 6-$CH_3$ | Bond | 2 | H/H |
| O | 5-$CH_3$ | Hexyl | O | 6-$CH_3$ | $NCH_3$ | 1 | $CH_3$/$CH_3$ |
| O | 5,6-$CH_3$ | Isopropyl | N—OH | 6-$CH_3$ | Bond | 2 | H/H |
| O | 6-$CF_3$ | Isopropyl | N—$OCH_3$ | 6-$CH_3$ | Bond | 2 | H/H |

TABLE 17

| X | $R^1$ | $R^2$ | A | Q | Y | s | $R^5/R^6$ |
|---|---|---|---|---|---|---|---|
| NH | 6-$CF_3$ | Propyl | O | 2,6-$CH_3$ | O | 1 | H/H |
| NH | 6-$CF_3$ | Isopropyl | O | 6-$CH_3$ | S | 1 | H/Ethyl |
| NH | 5-$CH_3$ | Isopropyl | N—OH | 6-$CH_3$ | $NCH_3$ | 1 | H/H |
| $NCH_3$ | 6-$CF_3$ | Propyl | O | 6-$CH_3$ | Bond | 2 | H/H |
| $NCH_3$ | 5,6-$OCH_3$ | Isopropyl | O | 6-$CH_3$ | Bond | 2 | H/H |
| $NCH_3$ | 5-$CF_3$ | Isopropyl | N—OH | 6-$CH_3$ | Bond | 2 | H/H |
| $NCH_3$ | 6-Cl | Isopropyl | O | 6-$CH_3$ | Bond | 2 | H/H |

Representative Compound 8

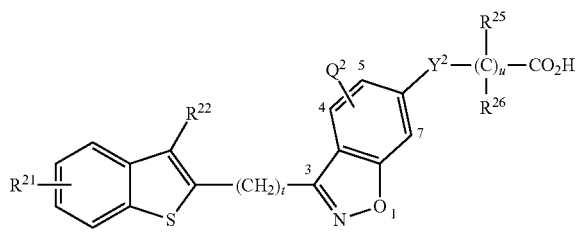

In the formula, $R^{21}$, $R^{22}$, t, $Q^2$, $Y^2$, u, $R^{25}$, and $R^{26}$ are set forth in Tables 18 and 19.

TABLE 18

| $R^{21}$ | $R^{22}$ | t | $Q^2$ | $Y^2$ | u | $R^{25}/R^{26}$ |
|---|---|---|---|---|---|---|
| 6-CF$_3$ | Isopropyl | 2 | 5-CH$_3$ | O | 1 | H/H |
| 6-CF$_3$ | Isopropyl | 2 | 5-CH$_3$ | NCH$_3$ | 1 | H/H |
| 6-CF$_3$ | Isopropyl | 2 | 5-CH$_3$ | Bond | 2 | H/H |
| 6-CF$_3$ | Isopropyl | 2 | H | O | 1 | H/H |
| 6-CF$_3$ | Isopropyl | 2 | H | NCH$_3$ | 1 | H/H |
| 6-Ethyl | Isopropyl | 2 | H | Bond | 2 | H/H |
| 6-CF$_3$ | Isopropyl | 3 | 5-CH$_3$ | Bond | 1 | H/H |

TABLE 19

| $R^{21}$ | $R^{22}$ | t | $Q^2$ | $Y^2$ | u | $R^{25}/R^{26}$ |
|---|---|---|---|---|---|---|
| 6-CF$_3$ | Propyl | 2 | 5-CH$_3$ | O | 1 | CH$_3$/CH$_3$ |
| 6-CF$_3$ | Propyl | 2 | 5-CH$_3$ | Bond | 2 | H/H |
| 6-CH$_3$ | Isopropyl | 2 | 5-CH$_3$ | S | 1 | H/H |
| 6-CH$_3$ | Methyl | 2 | 5-CH$_3$ | O | 1 | H/H |
| 6-CH$_3$ | Methyl | 2 | H | Bond | 1 | H/H |
| 6-Cl | Isopropyl | 2 | 5-CH$_3$ | NCH$_3$ | 1 | H/H |

Representative Compound 9

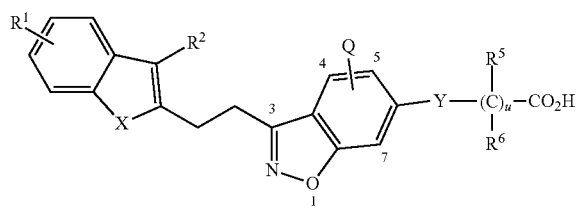

In the formula, X, $R^1$, $R^2$, Q, Y, u, $R^2$, and $R^6$ are set forth in Tables 20 and 21.

TABLE 20

| X | $R^1$ | $R^2$ | Q | Y | u | $R^5/R^6$ |
|---|---|---|---|---|---|---|
| O | 6-CF$_3$ | Propyl | 5-CH$_3$ | Bond | 2 | H/H |
| O | 6-CF$_3$ | Isopropyl | 5-CH$_3$ | Bond | 2 | H/H |
| O | 6-CF$_3$ | Isopropyl | H | O | 1 | CH$_3$/CH$_3$ |
| O | 6-CF$_3$ | Isopropyl | 4-CH$_3$ | Bond | 2 | H/H |
| O | 6-CF$_3$ | Hexyl | H | S | 1 | H/H |
| O | 6-CF$_3$ | Isopropyl | H | NCH$_3$ | 1 | H/H |
| O | 6-CF$_3$ | Isopropyl | 5-CH$_3$ | Bond | 2 | H/H |

TABLE 21

| X | $R^1$ | $R^2$ | Q | Y | u | $R^5/R^6$ |
|---|---|---|---|---|---|---|
| O | 5-CF$_3$ | Isopropyl | 5-CH$_3$ | Bond | 2 | H/H |
| O | 5-CF$_3$ | Hexyl | 5-CH$_3$ | Bond | 2 | H/H |
| NH | 6-CF$_3$ | Propyl | 5-CH$_3$ | Bond | 2 | H/H |
| NH | 6-CF$_3$ | Isopropyl | 5-CH$_3$ | Bond | 2 | H/H |
| NCH$_3$ | 6-CF$_3$ | Isopropyl | 5-CH$_3$ | O | 1 | CH$_3$/CH$_3$ |
| NCH$_3$ | 6-CF$_3$ | Isopropyl | H | Bond | 2 | H/H |

Representative compound 10

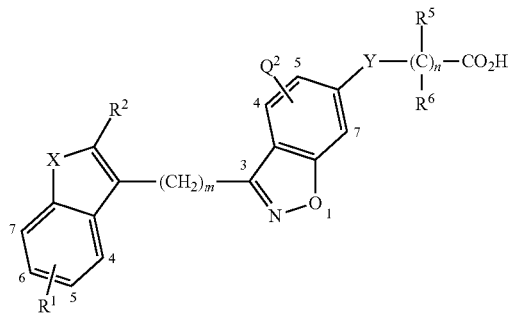

In the formula, X, $R^1$, $R^2$, m, Q, Y, n, $R^5$, and $R^6$ are set forth in Tables 22 and 23.

TABLE 22

| X | $R^1$ | $R^2$ | m | Q | Y | n | $R^5/R^6$ |
|---|---|---|---|---|---|---|---|
| S | 6-CF$_3$ | Isopropyl | 2 | 5-CH$_3$ | O | 1 | H/H |
| O | 6-CF$_3$ | Isopropyl | 2 | 5-CH$_3$ | NCH$_3$ | 1 | H/H |
| S | 6-t-Butyl | Isopropyl | 2 | 5-CH$_3$ | Bond | 2 | H/H |
| O | 5-CF$_2$CF$_3$ | Hexyl | 2 | H | O | 1 | CH$_3$/CH$_3$ |
| S | 6-CH$_3$ | Isopropyl | 2 | H | NCH$_3$ | 1 | H/H |
| O | 6-CF$_3$ | Isopropyl | 2 | H | Bond | 2 | H/H |
| S | 5,6-CH$_3$ | Isopropyl | 3 | 5-CH$_3$ | Bond | 1 | H/H |

TABLE 23

| X | $R^1$ | $R^2$ | m | Q | Y | n | $R^5/R^6$ |
|---|---|---|---|---|---|---|---|
| O | 5,6-OCH$_3$ | Propyl | 2 | 5-CH$_3$ | O | 1 | H/H |
| NH | 6-CF$_3$ | Propyl | 2 | 5-CH$_3$ | Bond | 2 | H/H |
| NCH$_3$ | 6-CH$_3$ | Isopropyl | 2 | 5-CH$_3$ | O | 1 | H/H |
| NCH$_3$ | 6-CH$_3$ | Methyl | 2 | 5-CH$_3$ | S | 1 | H/H |
| NCH$_3$ | 6-CH$_3$ | Methyl | 2 | H | Bond | 2 | H/H |
| NCH$_3$ | 6-Cl | Isopropyl | 2 | 5-CH$_3$ | NCH$_3$ | 1 | H/H |

The compounds of the present invention of the formulas (I), (II), and (III) can be prepared referring to the above-mentioned synthetic processes, as well as the processes of the below-mentioned Examples 1-21, and the processes described in the above-mentioned patent documents 1-4.

The pharmacological effects of the invention are described below.

The PPAR activating effect of the compound of the invention was determined by the following method:

A receptor expression plasmid (pSG5-GAL4-hPPARα or γ or δ (LBD)), a luciferase expression plasmid (pUC8-MH100×4-TK-Luc), and a β-galactosidase expression plasmid (pCMX-β-GAL) are transfected into CV-1 cells. After the gene transfer is conducted utilizing a transfection reagent (Lipofectamine 2000, Invitrogen), it is incubated for about 40 hours in the presence of a compound to be tested. The luciferase activity and β-GAL activity are measured on the soluble cells.

The luciferase activity is calibrated with the β-GAL activity. A relative ligand activity is calculated under the condition that the luciferase activity of the cells treated with GW-590735 (selective agonist for PPARα), Rosiglitazone (selective agonist for PPARγ), or GW-501516 (selective agonist for PPARδ) is set to 100% to determine $EC_{50}$ (Example 29).

As is evident from Table 24, the compounds of the invention show an excellent activating effect for PPARδ. As is also evident from Table 26, the compounds of the present invention described in Examples 22-28 have an excellent activating effect for PPARδ (Example 31).

As is further evident from Table 25, the compounds of the present invention described in Examples 19 and 21 show a high selectivity for PPARδ) compared with GW-501516 (Example 30).

As is described above, the compounds of the present invention represented by the formula (I), (II), and (III) have an excellent activating effect for PPARδ. Therefore, the compounds are expected to be used for treatment or prophylaxis of diseases, which include metabolic diseases such as diabetes, diseases to be treated with a hypoglycemic agent, syndrome X, obesity, hypercholesterolemia, and hyperlipoproteinemia, hyperlipidemia, arteriosclerosis, cardiac insufficiency, cardiomyopathy, non-alcoholic fatty hepatitis, diseases of cardiovascular system, bulimia, ischemic diseases, malignant tumors such as lung cancer, cancer of the breast, colon cancer, large intestine cancer, and ovary cancer, Alzheimer disease, and inflammatory diseases.

The compound of the invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents can be used. As the vehicles, lactose, D-mannitol, crystalline cellulose and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpyrrolidone (PVP) as the binders.

The compound of the invention can be administered to an adult generally in an amount of 0.1 mg to 100 mg a day by parenteral administration and 1 mg to 2,000 mg a day by oral administration. The dosage can be adjusted in consideration of age and conditions of the patient.

The invention is further described by the following non-limiting examples.

EXAMPLES

Reference Example 1

(1) Methyl 3-methylbenzothiophene-2-carboxylate

To a suspension of 55% sodium hydride (390 mg, 9.69 mmol) in THF (7 mL)-DMSO (20 mL) was added methyl thioglycolate (0.64 ml) under $N_2$ atmosphere. After ceasing of bubbling, the mixture was stirred for 15 minutes at room temperature, to which was added slowly a solution of 2-fluoroacetophenone (0.89 mL, 6.46 mmol) in DMSO (5 mL). The mixture was stirred at room temperature for 1 hour, diluted with water, and extracted with ethyl acetate. The organic layer was washed with saturated brine, dried over anhydrous sodium sulfate. The solvent was removed under reduced pressure, and the residue was recrystallized from ethyl acetate/hexane to give the titled compound as a white crystal (533 mg, 36%).

1H NMR ($CDCl_3$, 400 MHz): δ=2.78 (3H, s), 3.93 (3H, s), 7.4-7.5 (2H, m), 7.8-7.9 (2H, m).

(2) 3-Methylbenzothiophene-2-methanol

To an ice-cold suspension of lithium aluminum hydride (103 mg, 2.72 mmol) in THF (4.4 mL) was added dropwise over 15 minutes under $N_2$ atmosphere, a solution of the above-mentioned methyl 3-methylbenzothiophene-2-carboxylate (560 mg, 2.72 mmol) in THF (1 mL). The mixture was stirred under ice-cooling for 45 minutes, then at room temperature for 5 minutes, to which was added dropwise under ice-cooling saturated aqueous ammonium chloride solution. The mixture was filtered through a layer of Celite, washed with ethyl acetate. Combined organic layers were washed with saturated brine. After drying over anhydrous sodium sulfate, the solvent was removed under reduced pressure to give the titled compound as a white crystal (483 mg, yield 99%).

1H NMR ($CDCl_3$, 400 MHz): δ=1.79 (1H, t, J=6 Hz), 2.39 (3H, s), 4.91 (2H, d, J=6 Hz), 7.3-7.4 (2H, m), 7.67 (1H, dd, J=1 Hz, 8 Hz), 7.81 (1H, dd, J=1 Hz, 8 Hz).

Example 1

2-Methyl-4-[3-(3-methylbenzothiophen-2-yl)propionyl]-phenoxyacetic acid (1) 1-(4-Hydroxy-3-methylphenyl)-3-(3-methylbenzothiophen-2-yl)propan-1-one To an ice-cold solution of 3-methylbenzothiophene-2-methanol [Reference example 1] (480 mg, 2.69 mmol) in benzene (10 mL) was added dropwise, a solution of thionyl chloride (0.24 mL, 3.2 mmol) in benzene (3.5 mL). The mixture was stirred at room temperature for 3 hour, and concentrated under reduced pressure to give 2-chloromethyl-3-methylbenzothiophene as a yellow oil (548 mg, yield>99%).

Then, to a suspension of 55% sodium hydride (123 mg, 3.07 mmol) in THF (18 mL) was added dropwise over 10 minutes under $N_2$ atmosphere, a solution of ethyl 3-(4-benzyloxy-3-methylphenyl)-3-oxopropionate (870 mg, 2.79 mmol) in THF (5 mL). After 20 minutes, to the resultant mixture was added dropwise over 10 minutes a solution of 2-chloromethyl-3-methylbenzothiophene (548 mg, 2.79 mmol) in THF (5 mL). The mixture was heated under reflux for 25 hours, cooled to room temperature, and concentrated under reduced pressure. The residue was heated in acetic acid (18 mL) and concentrated hydrochloric acid (4 mL) at 110° C. for 20 hours. The reaction mixture was cooled at room temperature, extracted with ethyl acetate. The organic layer was washed with water, saturated aqueous sodium bicarbonate solution, and saturated brine, successively. After drying over anhydrous sodium sulfate, the solvent was removed under reduced pressure. The residue was purified by silica gel column chromatography (hexane/ethyl acetate=4/1), to give the titled compound as a yellow crystal (790 mg, yield 95%).

1H NMR ($CDCl_3$, 400 MHz): δ=2.27 (3H, s), 2.35 (3H, s), 3.31 (4H, s), 5.36 (1H, brs), 6.79 (1H, d, J=8 Hz), 7.28 (1H, dd, J=1 Hz, 8 Hz), 7.34 (1H, dt, J=1 Hz, 8 Hz), 7.61 (1H, d, J=8 Hz), 7.7-7.8 (3H, m).

(2) Ethyl 2-methyl-4-[3-(3-methylbenzothiophen-2-yl)-propionyl]phenoxyacetate To an ice-cold suspension of the above-mentioned 1-(4-hydroxy-3-methylphenyl)-3-(3-methylbenzothiophen-2-yl)propan-1-one (200 mg, 0.644 mmol) and potassium carbonate (178 mg, 1.29 mmol) in acetone (6.4 mL) was added slowly ethyl bromoacetate (0.14 mL, 1.3 mmol). The mixture was heated under reflux for 3 hours, to which was added saturated aqueous ammonium chloride solution, and extracted with ethyl acetate. The organic layer was washed with saturated brine, dried over anhydrous sodium sulfate. The solvent was removed under reduced pressure, and the residue was purified by silica gel column chromatography (hexane/ethyl acetate=5/1), to give the titled compound as a colorless oil (223 mg, yield 87%).

1H NMR (CDCl$_3$, 400 MHz): δ=1.29 (3H, t, J=7 Hz), 2.31 (3H, s), 2.35 (3H, s), 3.31 (4H, s), 4.26 (2H, q, J=7 Hz), 4.70 (2H, s), 6.70 (1H, d, J=8 Hz), 7.28 (1H, dd, J=1 Hz, 8 Hz), 7.34 (1H, dd, J=1 Hz, 8 Hz), 7.61 (1H, d, J=8 Hz), 7.77 (3H, m).

(3) 2-Methyl-4-[3-(3-methylbenzothiophen-2-yl)propionyl]phenoxyacetic acid

To a solution of ethyl 2-methyl-4-[3-(3-methylbenzothiophen-2-yl)propionyl]phenoxyacetate in ethanol (2 mL)/water (1 mL) was added lithium hydroxide monohydrate (70 mg, 1.7 mmol). The mixture was heated under reflux for 1 hour, cooled at room temperature. After addition of ice, the resultant mixture was acidified with 1M hydrochloric acid, and extracted with ethyl acetate. The organic layer was washed with saturated brine, dried over anhydrous sodium sulfate. The solvent was removed under reduced pressure, and the residue was recrystallized from ethyl acetate/hexane to give the titled compound as a pale yellow crystal (120 mg, 59%).

FAB-MS (m/e): 369 (M+1)

1H NMR (CDCl$_3$, 400 MHz): δ=2.31 (3H, s), 2.35 (3H, s), 3.31 (4H, s), 4.76 (2H, s), 6.73 (1H, d, J=8 Hz), 7.2-7.4 (2H, m), 7.61 (1H, d, J=8 Hz), 7.75 (1H, d, J=8 Hz), 7.7-7.9 (2H, m).

Example 2

2-Methyl-2-[2-methyl-4-[3-(3-methylbenzothiophen-2-yl)propionyl]phenoxy]propionic acid

(1) Ethyl 2-methyl-2-[2-methyl-4-[3-(3-methylbenzothiophen-2-yl)propionyl]phenoxy]propionate To an ice-cold suspension of 1-(4-hydroxy-3-methylphenyl)-3-(3-methylbenzothiophen-2-yl)propan-1-one [Example 1 (1)] (200 mg, 0.645 mmol) and potassium carbonate (445 mg, 3.22 mmol) in 2-butanone (6.4 mL) was added slowly ethyl 2-bromo-2-methylpropionate (0.48 mL, 3.2 mmol). The mixture was heated under reflux for 20 hours, to which was added saturated aqueous ammonium chloride solution, and extracted with ethyl acetate. The organic layer was washed with saturated brine, dried over anhydrous sodium sulfate. The solvent was removed under reduced pressure, and the residue was purified by silica gel column chromatography (hexane/ethyl acetate=7/1), to give the titled compound as a pale yellow oil (198 mg, yield 72%).

1H NMR (CDCl$_3$, 400 MHz): δ=1.21 (3H, t, J=7 Hz), 1.64 (6H, s), 2.25 (3H, s), 2.35 (3H, s), 3.30 (4H, s), 4.22 (2H, q, J=7 Hz), 6.60 (1H, d, J=8 Hz), 7.2-7.3 (1H, m), 7.34 (1H, dt, J=1 Hz, 8 Hz), 7.61 (1H, d, J=8 Hz), 7.70 (1H, dd, J=2 Hz, 8 Hz), 7.75 (1H, d, J=8 Hz), 7.79 (1H, d, J=2 Hz).

(2) 2-Methyl-2-[2-methyl-4-[3-(3-methylbenzothiophen-2-yl)propionyl]phenoxy]propionic acid The titled compound was prepared from the above-mentioned ethyl 2-methyl-2-[2-methyl-4-[3-(3-methylbenzothiophen-2-yl)propionyl]phenoxy]propionate (198 mg, 0.0466 mmol) in a procedure similar to that of Example 1 (3) as a pale yellow amorphous (87 mg, yield 47%).

FAB-MS (m/e): 397 (M+1)

1H NMR (CDCl$_3$, 400 MHz): δ=1.69 (6H, s), 2.24 (3H, s), 2.32 (3H, s), 3.28 (4H, m), 6.72 (1H, d, J=8 Hz), 7.25 (1H, t, J=7 Hz), 7.32 (1H, t, J=7 Hz), 7.58 (1H, d, J=8 Hz), 7.6-7.8 (2H, m), 7.78 (1H, m).

Example 3

2-Methyl-4-[3-[3-methyl-5-(trifluoromethyl)-benzothiophen-2-yl]propionyl]phenoxyacetic acid

(1) 1-(4-Hydroxy-3-methylphenyl)-3-[3-methyl-5-(trifluoromethyl)benzothiophen-2-yl)propan-1-one The titled compound was prepared from the above-mentioned 3-methyl-5-(trifluoromethyl)benzothiophen-2-yl-methanol [WO 2005077926] (930 mg, 3.78 mmol) in a procedure similar to that of Example 1 (1) as a brown crystal (400 mg, yield 31%).

1H NMR (CDCl$_3$, 400 MHz): δ=2.28 (3H, s), 2.40 (3H, s), 3.33 (4H, s), 5.18 (1H, br s), 6.80 (1H, d, J=8 Hz), 7.49 (1H, d, J=8 Hz), 7.75 (1H, d, J=8 Hz), 7.79 (1H, s), 7.84 (1H, d, J=8 Hz), 7.86 (1H, s).

(2) Ethyl 2-methyl-4-[3-[3-methyl-5-(trifluoromethyl)-benzothiophen-2-yl]propionyl]phenoxyacetate The titled compound was prepared from the above-mentioned 1-(4-hydroxy-3-methylphenyl)-3-[3-methyl-5-(trifluoromethyl)benzothiophen-2-yl)propan-1-one (200 mg, 0.529 mmol) in a procedure similar to that of Example 1 (2) as a white crystal (217 mg, yield 88%).

1H NMR (CDCl$_3$, 400 MHz): δ=1.29 (3H, t, J=7 Hz), 2.31 (3H, s), 2.39 (3H, s), 3.33 (4H, s), 4.26 (2H, q, J=7 Hz), 4.70 (2H, s), 6.70 (1H, d, J=8 Hz), 7.49 (1H, d, J=8 Hz), 7.7-7.9 (4H, m).

(3) 2-Methyl-4-[3-[3-methyl-5-(trifluoromethyl)-benzothiophen-2-yl]propionyl]phenoxyacetic acid The titled compound was prepared from the above-mentioned ethyl 2-methyl-4-[3-[3-methyl-5-(trifluoromethyl)benzothiophen-2-yl]propionyl]phenoxyacetate (217 mg, 0.467 mmol) in a procedure similar to that of Example 1 (3) as a white crystal (156 mg, yield 77%).

FAB-MS (m/e): 437 (M+1)

1H NMR (CDCl$_3$, 400 MHz): δ=2.31 (3H, s), 2.39 (3H, s), 3.33 (4H, s), 4.77 (2H, s), 6.74 (1H, d, J=8 Hz), 7.49 (1H, d, J=8 Hz), 7.7-7.9 (4H, m).

IR (KBr, cm-1): 2954, 2923, 2800, 2592, 1772, 1745, 1670, 1649, 1601, 1576, 1508, 1456, 1436, 1434, 1421, 1383, 1350, 1325, 1300, 1257, 1227, 1201, 1173, 1136, 1132, 1070, 1063, 1016, 947, 895, 891, 889, 872, 825, 808, 775, 677, 660.

Example 4

2-Methyl-2-[2-methyl-4-[3-[3-methyl-5-(trifluoromethyl)-benzothiophen-2-yl]propionyl]phenoxy]propionic acid

(1) Ethyl 2-methyl-2-[2-methyl-4-[3-[3-methyl-5-(trifluoromethyl)benzothiophen-2-yl]propionyl]phenoxy]propionate The titled compound was prepared from the above-mentioned 1-(4-hydroxy-3-methylphenyl)-3-[3-methyl-5-(trifluoromethyl)benzothiophen-2-yl]propan-1-one [Example 3 (1)] (200 mg, 0.529 mmol) in a procedure similar to that of Example 2 (1) as a pale yellow oil (211 mg, yield 81%).

1H NMR (CDCl$_3$, 400 MHz): δ=1.21 (3H, t, J=7 Hz), 1.64 (6H, s), 2.25 (3H, s), 2.39 (3H, s), 3.2-3.4 (4H, m), 4.21 (2H, q, J=7 Hz), 6.60 (1H, d, J=8 Hz), 7.49 (1H, d, J=8 Hz), 7.69 (1H, dd, J=2 Hz, 8 Hz), 7.7-7.9 (3H, m).

(2) 2-Methyl-2-[2-methyl-4-[3-[3-methyl-5-(trifluoromethyl)benzothiophen-2-yl]propionyl]phenoxy]propionic acid The titled compound was prepared from the above-mentioned ethyl 2-methyl-2-[2-methyl-4-[3-[3-methyl-5-(trifluoromethyl)benzothiophen-2-yl]propionyl]phenoxy]-propionate (211 mg, 0.428 mmol) in a procedure similar to that of Example 1 (3) as a pale yellow oil (162 mg, yield 81%).

FAB-MS (m/e): 465 (M+1)

1H NMR (CDCl$_3$, 400 MHz): δ=1.68 (6H, s), 2.25 (3H, s), 2.38 (3H, s), 3.32 (4H, s), 6.73 (1H, d, J=8 Hz), 7.48 (1H, dd, J=1 Hz, 8 Hz), 7.73 (1H, dd, J=2 Hz, 8 Hz), 7.79 (1H, d, J=2 Hz), 7.82 (1H, d, J=8 Hz), 7.85 (1H, d, J=1 Hz).

Example 5

2-Methyl-4-[3-[3-methyl-6-(trifluoromethyl)-benzothiophen-2-yl]propionyl]phenoxyacetic acid

(1) 1-(4-Hydroxy-3-methylphenyl)-3-[3-methyl-6-(trifluoromethyl)benzothiophen-2-yl)propan-1-one The titled compound was prepared from the above-mentioned 3-methyl-6-(trifluoromethyl)benzothiophen-2-yl-methanol [WO 2005077926] (906 mg, 3.68 mmol) and Ethyl 3-(4-benzyloxy-3-methylphenyl)-3-oxopropionate (1.14 g, 3.65 mmol) in a procedure similar to that of Example 1 (1) as a brown powder (680 mg, yield 49%).

1H NMR (CDCl$_3$, 400 MHz): δ=2.27 (3H, s), 2.38 (3H, s), 3.33 (4H, s), 5.27 (1H, br s), 6.80 (1H, d, J=8 Hz), 7.57 (1H, d, J=8 Hz), 7.69 (1H, d, J=8 Hz), 7.7-7.9 (2H, m), 8.02 (1H, s).

(2) Ethyl 2-methyl-4-[3-[3-methyl-6-(trifluoromethyl)-benzothiophen-2-yl]propionyl]phenoxyacetate The titled compound was prepared from the above-mentioned 1-(4-hydroxy-3-methylphenyl)-3-[3-methyl-6-(trifluoromethyl)-benzothiophen-2-yl)propan-1-one (200 mg, 0.529 mmol) in a procedure similar to that of Example 1 (2) as a yellow brown crystal (214 mg, yield 87%).

1H NMR (CDCl$_3$, 400 MHz): δ=1.30 (3H, t, J=7 Hz), 2.32 (3H, s), 2.40 (3H, s), 3.34 (4H, s), 4.27 (2H, q, J=7 Hz), 4.71 (2H, s), 6.71 (1H, d, J=8 Hz), 7.58 (1H, d, J=8 Hz), 7.70 (1H, d, J=8 Hz), 7.7-7.8 (2H, m), 8.03 (1H, s).

(3) 2-Methyl-4-[3-[3-methyl-6-(trifluoromethyl) benzothiophen-2-yl]propionyl]phenoxyacetic acid The titled compound was prepared from the above-mentioned ethyl 2-methyl-4-[3-[3-methyl-6-(trifluoromethyl) benzothiophen-2-yl]propionyl]phenoxyacetate (214 mg, 0.461 mmol) in a procedure similar to that of Example 1 (3) as a white crystal (146 mg, yield 73%).

FAB-MS (m/e): 437 (M+1)

1H NMR (CDCl$_3$, 400 MHz): δ=2.31 (3H, s), 2.39 (3H, s), 3.34 (4H, s), 4.77 (2H, s), 6.74 (1H, d, J=8 Hz), 7.56 (1H, dd, J=1 Hz, 8 Hz), 7.69 (1H, d, J=8 Hz), 7.7-7.9 (2H, m), 8.02 (1H, s).

IR (KBr, cm-1): 2913, 2592, 1772, 1745, 1676, 1643, 1601, 1578, 1506, 1425, 1421, 1408, 1385, 1352, 1331, 1277, 1257, 1203, 1161, 1130, 1114, 1099, 1080, 887, 871, 823, 815, 721.

Example 6

2-Methyl-2-[2-methyl-4-[3-[3-methyl-6-(trifluoromethyl)-benzothiophen-2-yl]propionyl]-phenoxypropionic acid

(1) Ethyl 2-methyl-2-[2-methyl-4-[3-[3-methyl-6-(trifluoromethyl)benzothiophen-2-yl]propionyl]phenoxypropionate The titled compound was prepared from the above-mentioned 1-(4-hydroxy-3-methylphenyl)-3-[3-methyl-6-(trifluoromethyl)benzothiophen-2-yl)propan-1-one [Example 5 (1)] (200 mg, 0.529 mmol) in a procedure similar to that of Example 2 (1) as a pale yellow oil (252 mg, yield 97%).

1H NMR (CDCl$_3$, 400 MHz): δ=1.21 (3H, t, J=7 Hz), 1.65 (6H, s), 2.25 (3H, s), 2.38 (3H, s), 3.3-3.4 (4H, m), 4.22 (2H, q, J=7 Hz), 6.60 (1H, d, J=8 Hz), 7.56 (1H, d, J=8 Hz), 7.6-7.8 (2H, m), 7.78 (1H, s), 8.01 (1H, s).

(2) 2-Methyl-2-[2-methyl-4-[3-[3-methyl-6-(trifluoromethyl)benzothiophen-2-yl]propionyl]phenoxypropionic acid The titled compound was prepared from the above-mentioned ethyl 2-methyl-2-[2-methyl-4-[3-[3-methyl-6-(trifluoromethyl)benzothiophen-2-yl]propionyl]phenoxypropionate (252 mg, 0.512 mmol) in a procedure similar to that of Example 1 (3) as a white crystal (170 mg, yield 72%).

FAB-MS (m/e): 465 (M+1)

1H NMR (CDCl$_3$, 400 MHz): δ=1.68 (6H, s), 2.27 (3H, s), 2.38 (3H, s), 3.33 (4H, s), 6.75 (1H, d, J=8 Hz), 7.56 (1H, dd, J=1 Hz, 8 Hz), 7.68 (1H, d, J=8 Hz), 7.73 (1H, dd, J=2 Hz, 8 Hz), 7.81 (1H, d, J=2 Hz), 8.01 (1H, s).

IR (KBr, cm-1): 3072, 2997, 2927, 2563, 1712, 1672, 1603, 1581, 1502, 1413, 1406, 1385, 1352, 1323, 1279, 1257, 1159, 1120, 813.

Example 7

3-[4-[3-[3-Methyl-6-(trifluoromethyl)-benzothiophen-2-yl]propionyl]-2-methylphenyl]propionic acid

(1) Methyl 3-[4-[3-[3-methyl-6-(trifluoromethyl) benzothiophen-2-yl]propenoyl]-2-methylphenyl] acrylate To an ice-cold suspension of methyl (4-acetyl-2-methylphenyl)acrylate [WO 2007119887] (89 mg, 0.41 mmol)

and powdered Molecular sieves 3A (250 mg) in THF (2 mL) was added 0.5M MeONa in MeOH (1.0 mL, 0.49 mmol) under N$_2$ atmosphere. The mixture was stirred for 10 minutes under ice-cooling, to which was added slowly a solution of 3-methyl-6-(trifluoromethyl)benzothiophen-2-carboxaldehyde (100 mg, 0.410 mmol) in THF (1.7 mL). The mixture was stirred for 4 hours under ice-cooling, neutralized with 1N hydrochloric acid, and filtered. The filtrate was washed with water, and the organic layer was dried over anhydrous sodium sulfate. The solvent was removed under reduced pressure, and the residue was recrystallized from ethyl acetate/hexane to give the titled compound as a yellow crystal (87 mg, 48%).

1H NMR (CDCl$_3$, 400 MHz): δ=2.55 (3H, s), 2.61 (3H, s), 3.84 (3H, s), 6.47 (1H, d, J=16 Hz), 7.42 (1H, d, J=15 Hz), 7.62 (1H, d, J=8 Hz), 7.68 (1H, d, J=8 Hz), 7.83 (1H, d, J=8 Hz), 7.8-7.9 (2H, m), 7.99 (1H, d, J=16 Hz), 8.08 (1H, s), 8.21 (1H, d, J=15 Hz).

(2) Methyl 3-[4-[3-[3-methyl-6-(trifluoromethyl) benzothiophen-2-yl]propionyl]-2-methylphenyl] propionate Methyl 3-[4-[3-[3-methyl-6-(trifluoromethyl)benzothiophen-2-yl]propenoyl]-2-methylphenyl]acrylate (85 mg, 0.19 mmol) was hydrogenated in MeOH (1 mL)/THF (1 mL) for 1 hour at room temperature using 10% palladium-carbon (17 mg) as a catalyst. After removal of the catalyst by filtration, the filtrate was concentrated to dryness. The residue was purified by silica gel column chromatography (hexane/ethyl acetate=5/1), to give the titled compound as a pale yellow crystal (38 mg, yield 44%).

1H NMR (CDCl$_3$, 400 MHz): δ=2.37 (3H, s), 2.39 (3H, s), 2.60 (2H, t, J=8 Hz), 2.98 (2H, t, J=8 Hz), 3.35 (4H, s), 3.68 (3H, s), 7.22 (1H, d, J=8 Hz), 7.57 (1H, d, J=8 Hz), 7.68 (1H, s), 7.71 (1H, d, J=8 Hz), 7.7-7.8 (1H, m), 8.02 (1H, s).

(3) 3-[4-[3-[3-Methyl-6-(trifluoromethyl)benzothiophen-2-yl]-propionyl]-2-methylphenyl]propionic acid The titled compound was prepared from the above-mentioned methyl 3-[4-[3-[3-methyl-6-(trifluoromethyl)-benzothiophen-2-yl]propionyl]-2-methylphenyl]propionate (38 mg, 0.085 mmol) in a procedure similar to that of Example 1 (3) as a white crystal (24 mg, yield 65%).

FAB-MS (m/e): 435 (M+1)

1H NMR (CDCl$_3$, 400 MHz): δ=2.37 (3H, s), 2.39 (3H, s), 2.66 (2H, t, J=8 Hz), 2.99 (2H, t, J=8 Hz), 3.35 (4H, s), 7.24 (1H, d, J=8 Hz), 7.57 (1H, d, J=8 Hz), 7.69 (1H, d, J=8 Hz), 7.74 (1H, d, J=8 Hz), 7.75 (1H, s), 8.02 (1H, s).

IR (KBr, cm-1): 3419, 3180, 2916, 2661, 1722, 1662, 1604, 1570, 1456, 1413, 1408, 1354, 1327, 1259, 1230, 1157, 1112, 1082, 1068, 1066, 962, 879, 827, 771, 721, 644, 605.

Example 8

3-[4-[3-[3-Ethyl-6-(trifluoromethyl)benzothiophen-2-yl]propionyl]-2-methylphenyl]propionic acid (1) Methyl 3-[4-[3-[3-ethyl-6-(trifluoromethyl)benzothiophen-2-yl]propenoyl]-2-methylphenyl]acrylate The titled compound was prepared from 3-ethyl-6-(trifluoromethyl)benzothiophen-2-carboxaldehyde [WO 2005077926] (185 mg, 0.716 mmol) and methyl 3-(4-acetyl-2-methylphenyl)acrylate (156 mg, 0.715 mmol) in a procedure similar to that of Example 7 (1) as a yellow crystal (186 mg, yield 57%).

1H NMR (CDCl$_3$, 400 MHz): δ=1.31 (3H, t, J=7 Hz), 2.55 (3H, s), 3.09 (2H, q, J=7 Hz), 3.84 (3H, s), 6.47 (1H, d, J=16 Hz), 7.43 (1H, d, J=15 Hz), 7.62 (1H, d, J=8 Hz), 7.69 (1H, d, J=8 Hz), 7.8-7.9 (3H, m), 8.00 (1H, d, J=16 Hz), 8.08 (1H, s), 8.20 (1H, d, J=15 Hz).

(2) Methyl 3-[4-[3-[3-methyl-6-(trifluoromethyl) benzothiophen-2-yl]propionyl]-2-methylphenyl] propionate The titled compound was prepared from the above-mentioned methyl 3-[4-[3-[3-ethyl-6-(trifluoromethyl)-benzothiophen-2-yl]propenoyl]-2-methylphenyl]acrylate (186 mg, 0.406 mmol) in a procedure similar to that of Example 7 (2) as a pale yellow crystal (100 mg, yield 53%).

1H NMR (CDCl$_3$, 400 MHz): δ=1.24 (3H, t, J=7 Hz), 2.37 (3H, s), 2.60 (2H, t, J=8 Hz), 2.88 (2H, q, J=7 Hz), 2.99 (2H, t, J=8 Hz), 3.36 (4H, s), 3.68 (3H, s), 7.23 (1H, d, J=8 Hz), 7.56 (1H, d, J=8 Hz), 7.7-7.8 (3H, m), 8.03 (1H, s).

(3) 3-[4-[3-[3-Ethyl-6-(trifluoromethyl)benzothiophen-2-yl]-propionyl]-2-methylphenyl]propionic acid The titled compound was prepared from the above-mentioned methyl 3-[4-[3-[3-ethyl-6-(trifluoromethyl)benzothiophen-2-yl]propionyl]-2-methylphenyl]propionate (100 mg, 0.216 mmol) in a procedure similar to that of Example 1 (5) as a pale yellow crystal (55 mg, yield 57%).

FAB-MS (m/e): 449 (M+1)

1H NMR (CDCl$_3$, 400 MHz): δ=1.24 (3H, t, J=7 Hz), 2.38 (3H, s), 2.67 (2H, t, J=7 Hz), 2.88 (2H, q, J=7 Hz), 3.00 (2H, t, J=7 Hz), 3.36 (4H, s), 7.25 (1H, d, J=7 Hz), 7.56 (1H, d, J=7 Hz), 7.7-7.8 (3H, m), 8.03 (1H, s).

IR (KBr, cm-1): 3035, 2968, 2929, 2634, 1709, 1682, 1608, 1436, 1429, 1409, 1363, 1328, 1280, 1259, 1223, 1219, 1159, 1115, 1081, 1053, 883, 815.

Example 9

3-[2-Methyl-4-[3-[3-propyl-6-(trifluoromethyl)benzothiophen-2-yl]propionyl]phenyl]propionic acid (1)
1-[2-Fluoro-4-(trifluoromethyl)phenyl]butan-1-one To a solution of 1-bromo-2-fluoro-4-(trifluoromethyl)benzene (0.30 mL, 2.1 mmol) in THF (6 mL) was added dropwise 1.5M butyllithium in THF (1.65 mL) at −78° C. The mixture was stirred at −78° C. for 15 minutes, to which was added a solution of butyraldehyde (0.18 mL, 2.5 mmol) in THF (2 ml) at −78° C. After stirring at −78° C. for 30 minutes, the mixture was treated with acetic acid (1 mL)/THF (2 mL), and then followed by water at room temperature. The organic layer was separated, and the aqueous layer was extracted with ether. The combined organic layers were washed with saturated brine. After drying over anhydrous sodium sulfate, the solvent was removed under reduced pressure to give 1-[2-fluoro-4-(trifluoromethyl)-phenyl]butanol. To a suspension of the product and powdered Molecular sieves 3A (750 mg) in dichloromethane was added pyridinium chlorochromate (887 mg, 4.12 mmol). The mixture was stirred for 16 hours at room temperature, to which was added ether (20 mL) and silica gel (Wakogel C-300HG, 2 g). The mixture was stirred for 10 minutes at room temperature, and filtered. The filtrate was concentrated to dryness, and the residue was purified by silica gel column chromatography (hexane/ethyl acetate=6/1), to give the titled compound as a white crystal (323 mg, yield 67%).

1H NMR (CDCl$_3$, 400 MHz): δ=1.00 (3H, t, J=7 Hz), 1.7-1.8 (2H, m), 2.97 (2H, t, J=7 Hz), 7.42 (1H, d, J=10 Hz), 7.49 (1H, d, J=8 Hz), 7.95 (1H, t, J=8 Hz).

(2) Methyl 3-propyl-6-(trifluoromethyl)benzothiophen-2-carboxylate

The titled compound was prepared from the above-mentioned 1-[2-fluoro-4-(trifluoromethyl)phenyl]butan-1-one (320 mg, 1.37 mmol) in a procedure similar to that of Reference example 1 (1) as a colorless oil (230 mg, yield 56%).

1H NMR (CDCl$_3$, 400 MHz): δ=1.03 (3H, t, J=7 Hz), 1.71 (2H, m), 3.2-3.4 (2H, m), 3.95 (3H, s), 7.63 (1H, d, J=8 Hz), 7.95 (1H, d, J=8 Hz), 0.12 (1H, s).

(3) [3-Propyl-6-(trifluoromethyl)benzothiophen-2-yl]-methanol

The titled compound was prepared from the above-mentioned methyl 3-propyl-6-(trifluoromethyl)benzothiophene-2-carboxylate (230 mg, 0.761 mmol) in a procedure similar to that of Reference example 1 (2) (126 mg, yield 60%).

1H NMR (CDCl$_3$, 400 MHz): δ=0.98 (3H, t, J=7 Hz), 1.6-1.7 (2H, m), 1.89 (1H, t, J=6 Hz), 2.84 (2H, t, J=7 Hz), 4.96 (2H, d, J=6 Hz), 7.58 (1H, dd, J=1 Hz, 8 Hz), 7.77 (1H, d, J=8 Hz), 8.10 (1H, s).

(4) 3-Propyl-6-(trifluoromethyl)benzothiophene-2-carboxaldehyde

To a suspension of [3-propyl-6-(trifluoromethyl)-benzothiophen-2-yl]methanol (126 mg, 0.459 mmol) and powdered Molecular sieves 3A (250 mg) in dichloromethane (2.3 mL) was added pyridinium chlorochromate (198 mg, 0.919 mmol). The mixture was stirred for 40 minutes at room temperature, to which was added ether (20 mL) and silica gel (Wakogel C-300HG, 2 g). The mixture was stirred for 10 minutes at room temperature, and filtered. The filtered cake was washed out with ether. The filtrate and washings were combined, and concentrated to give the titled compound as a brown crystal (112 mg, yield 90%).

1H NMR (CDCl$_3$, 400 MHz): δ=1.04 (3H, t, J=7 Hz), 1.7-1.9 (2H, m), 3.26 (2H, t, J=7 Hz), 7.65 (1H, d, J=8 Hz), 8.01 (1H, d, J=8 Hz), 8.17 (1H, s), 10.34 (1H, s).

(5) Methyl 3-[2-methyl-4-[3-[3-propyl-6-(trifluoromethyl)benzothiophen-2-yl]propenoyl]phenyl]acrylate The titled compound was prepared from the above-mentioned 3-propyl-6-(trifluoromethyl)benzothiophen-2-carboxaldehyde (112 mg, 0.411 mmol) and methyl 3-(4-acetyl-2-methylphenyl)acrylate (90 mg, 0.41 mmol) in a procedure similar to that of Example 7 (1) as a yellow crystal (107 mg, yield 55%).

1H NMR (CDCl$_3$, 400 MHz): δ=1.01 (3H, t, J=7 Hz), 1.6-1.8 (2H, m), 2.55 (3H, s), 3.04 (2H, t, J=7 Hz), 3.84 (3H, s), 6.47 (1H, d, J=16 Hz), 7.42 (1H, d, J=15 Hz), 7.61 (1H, d, J=8 Hz), 7.69 (1H, d, J=8 Hz), 7.85 (1H, d, J=8 Hz), 7.8-7.9 (2H, m), 8.00 (1H, d, J=16 Hz), 8.08 (1H, s), 8.18 (1H, d, J=15 Hz).

(6) Methyl 3-[2-methyl-4-[3-[3-propyl-6-(trifluoromethyl)benzothiophen-2-yl]propionyl]phenyl]propionate The titled compound was prepared from the above-mentioned methyl 3-[2-methyl-4-[3-[3-propyl-6-(trifluoromethyl)benzothiophen-2-yl]propenoyl]phenyl]acrylate (85 mg, 0.18 mmol) in a procedure similar to that of Example 7 (2) as a colorless oil (22 mg, yield 20%).

1H NMR (CDCl$_3$, 400 MHz): δ=1.00 (3H, t, J=7 Hz), 1.6-1.7 (2H, m), 2.37 (3H, s), 2.61 (2H, t, J=7 Hz), 2.83 (2H, t, J=7 Hz), 2.99 (2H, t, J=7 Hz), 3.36 (4H, s), 3.68 (3H, s), 7.23 (1H, d, J=8 Hz), 7.55 (1H, d, J=8 Hz), 7.7-7.8 (3H, m), 8.02 (1H, s).

(7) 3-[2-Methyl-4-[3-[3-propyl-6-(trifluoromethyl)benzothiophen-2-yl]propionyl]phenyl]propionic acid The titled compound was prepared from the above-mentioned methyl 3-[2-methyl-4-[3-[3-propyl-6-(trifluoromethyl)benzothiophen-2-yl]propionyl]phenyl]propionate (38 mg, 0.08 mmol) in a procedure similar to that of Example (3) as a white crystal (14 mg, yield 66%).

FAB-MS (m/e): 463 (M+1)

1H NMR (CDCl$_3$, 400 MHz): δ=1.00 (3H, t, J=7 Hz), 1.6-1.7 (2H, m), 2.38 (3H, s), 2.67 (2H, t, J=8 Hz), 2.84 (2H, t, J=8 Hz), 3.00 (2H, t, J=8 Hz), 3.3-3.4 (4H, m), 7.25 (1H, d, J=7 Hz), 7.55 (1H, dd, J=2 Hz, 8 Hz), 7.7-7.8 (3H, m), 8.02 (1H, s).

IR (KBr, cm-1): 2964, 2927, 1712, 1693, 1683, 1608, 1428, 1409, 1365, 1330, 1305, 1276, 1259, 1220, 1159, 1114, 1081, 883, 817, 721, 433, 422.

Example 10

3-[2-Methyl-4-[3-[3-butyl-6-(trifluoromethyl)benzothiophen-2-yl]propionyl]phenyl]propionic acid (1) 1-[2-Fluoro-4-(trifluoromethyl)phenyl]pentan-1-one The titled compound was prepared from 1-bromo-2-fluoro-4-(trifluoromethyl)benzene (200 mg, 0.823 mmol) and valeraldehyde (0.05 mL, 0.8 mmol) in a procedure similar to that of Example 9 (1) as a pale yellow oil (114 mg, yield 97%).

1H NMR (CDCl$_3$, 400 MHz): δ=0.95 (3H, t, J=7 Hz), 1.3-1.5 (2H, m), 1.6-1.8 (2H, m), 2.99 (2H, td, J=3 Hz, 7 Hz), 7.42 (1H, d, J=10 Hz), 7.49 (1H, d, J=8 Hz), 7.94 (1H, t, J=8 Hz).

(2) Methyl 3-butyl-6-(trifluoromethyl)benzothiophen-2-carboxylate

The titled compound was prepared from the above-mentioned 1-[2-fluoro-4-(trifluoromethyl)phenyl]pentan-1-one (246 mg, 1.05 mmol) in a procedure similar to that of Example 1 (1) as a pale yellow oil (241 mg, yield 38%).

1H NMR (CDCl$_3$, 400 MHz): δ=0.97 (3H, t, J=7 Hz), 1.4-1.5 (2H, m), 1.6-1.7 (2H, m), 3.31 (2H, t, J=7 Hz), 3.95 (3H, s), 7.63 (1H, d, J=8 Hz), 7.95 (1H, d, J=8 Hz), 8.12 (1H, s).

(3) [3-Butyl-6-(trifluoromethyl)benzothiophen-2-yl]-methanol

The titled compound was prepared from the above-mentioned methyl 3-butyl-6-(trifluoromethyl)benzothiophen-2- carboxylate (240 mg, 0.759 mmol) in a procedure similar to that of Example 1 (2) (100 mg, yield 46%).

1H NMR (CDCl$_3$, 400 MHz): δ=0.95 (3H, t, J=8 Hz), 1.3-1.5 (2H, m), 1.5-1.7 (2H, m), 1.88 (1H, t, J=5 Hz), 2.86 (2H, t, J=8 Hz), 4.96 (2H, d, J=5 Hz), 7.58 (1H, dd, J=1 Hz, 8 Hz), 7.77 (1H, d, J=8 Hz), 8.10 (1H, s).

(4) 3-Butyl-6-(trifluoromethyl)benzothiophene-2-carboxaldehyde

The titled compound was prepared from the above-mentioned [3-butyl-6-(trifluoromethyl)benzothiophen-2-yl] methanol (100 mg, 0.347 mmol) in a procedure similar to that of Example 9 (4) as a pale brown oil (88 mg, yield 89%).

1H NMR (CDCl$_3$, 400 MHz): δ=0.97 (3H, t, J=7 Hz), 1.4-1.5 (2H, m), 1.7-1.8 (2H, m), 3.28 (2H, t, J=7 Hz), 7.65 (1H, d, J=8 Hz), 8.01 (1H, d, J=8 Hz), 8.17 (1H, s), 10.34 (1H, s).

(5) Methyl 3-[4-[3-[3-butyl-6-(trifluoromethyl)benzothiophen-2-yl]propenoyl]-2-methylphenyl]acrylate The titled compound was prepared from the above-mentioned 3-butyl-6-(trifluoromethyl)benzothiophen-2-carboxaldehyde (88 mg, 0.31 mmol) and methyl 3-(4-acetyl-2-methylphenyl)acrylate (67 mg, 0.31 mmol) in a procedure similar to that of Example 7 (1) as a yellow crystal (77 mg, yield 51%).

1H NMR (CDCl$_3$, 400 MHz): δ=0.96 (3H, t, J=7 Hz), 1.4-1.5 (2H, m), 1.6-1.7 (2H, m), 2.55 (3H, s), 3.06 (2H, t, J=7 Hz), 3.85 (3H, s), 6.47 (1H, d, J=16 Hz), 7.42 (1H, d, J=15 Hz), 7.61 (1H, d, J=8 Hz), 7.69 (1H, d, J=8 Hz), 7.84 (1H, d, J=8 Hz), 7.8-7.9 (2H, m), 7.99 (1H, d, J=16 Hz), 8.08 (1H, s), 8.18 (1H, d, J=15 Hz).

(6) Methyl 3-[4-[3-[3-butyl-6-(trifluoromethyl)benzothiophen-2-yl]propionyl]-2-methylphenyl]propionate The titled compound was prepared from the above-mentioned methyl 3-[4-[3-[3-butyl-6-(trifluoromethyl)-benzothiophen-2-yl]propenoyl]-2-methylphenyl]acrylate (77 mg, 0.16 mmol) in a procedure similar to that of Example 7 (2) as a white crystal (43 mg, yield 55%).

1H NMR (CDCl$_3$, 400 MHz): δ=0.95 (3H, t, J=7 Hz), 1.3-1.5 (2H, m), 1.5-1.7 (2H, m), 2.37 (3H, s), 2.61 (2H, t, J=7 Hz), 2.85 (2H, t, J=8 Hz), 2.99 (2H, t, J=8 Hz), 3.36 (4H, s), 3.68 (3H, s), 7.23 (1H, d, J=8 Hz), 7.55 (1H, d, J=8 Hz), 7.71 (1H, d, J=8 Hz), 7.7-7.8 (2H, m), 8.02 (1H, s).

(7) 3-[4-[3-[3-butyl-6-(trifluoromethyl)benzothiophen-2-yl]-propionyl]-2-methylphenyl]propionic acid The titled compound was prepared from the above-mentioned methyl 3-[4-[3-[3-butyl-6-(trifluoromethyl)-benzothiophen-2-yl]-propionyl]-2-methylphenyl]propionate (43 mg, 0.088 mmol) in a procedure similar to that of Example 1 (3) as a white crystal (32 mg, yield 77%).

FAB-MS (m/e): 477 (M+1)

1H NMR (CDCl$_3$, 400 MHz): δ=0.95 (3H, t, J=7 Hz), 1.3-1.5 (2H, m), 1.5-1.7 (2H, m), 2.38 (3H, s), 2.66 (2H, t, J=7 Hz), 2.85 (2H, t, J=8 Hz), 3.00 (2H, t, J=8 Hz), 3.36 (4H, s), 7.25 (1H, d, J=7 Hz), 7.55 (1H, dd, J=1 Hz, 8 Hz), 7.6-7.8 (3H, m), 8.02 (1H, s).

IR (KBr, cm-1): 2956, 2927, 2861, 2360, 2341, 1712, 1681, 1608, 1569, 1428, 1411, 1365, 1328, 1278, 1257, 1214, 1157, 1114, 1083.

Example 11

3-[2-Methyl-4-[3-[3-isobutyl-6-(trifluoromethyl) benzothiophen-2-yl]propionyl]phenyl]propionic acid

(1) 1-[2-Fluoro-4-(trifluoromethyl)phenyl]-3-methylbutanol

To mixed solution of 2M isobutylmagnesium bromide in THF (6.25 mL) and ether (50 mL), was added dropwise a solution of 2-fluoro-4-(trifluoromethyl)benzaldehyde (2.0 g, 10 mmol) in ether (18 mL) under N$_2$ atmosphere. The mixture was stirred at room temperature for 45 minutes, to which was added saturated aqueous ammonium chloride solution and 1M hydrochloric acid under ice-cooling. The aqueous layer was extracted with ether. The organic layer was washed with saturated aqueous sodium bicarbonate solution, saturated brine successively. After drying over anhydrous sodium sulfate, the solvent was removed under reduced pressure. The residue was purified by silica gel column chromatography (hexane/ethyl acetate=10/1), to give the titled compound as a yellow oil (601 mg, yield 23%).

1H NMR (CDCl$_3$, 400 MHz): δ=0.97 (3H, d, J=7 Hz), 0.99 (3H, d, J=7 Hz), 1.4-1.6 (1H, m), 1.6-1.9 (2H, m), 1.89 (1H, d, J=4 Hz), 5.1-5.2 (1H, m), 7.28 (1H, d, J=10 Hz), 7.43 (1H, d, J=8 Hz), 7.63 (1H, d, J=8 Hz).

(2) 1-[2-Fluoro-4-(trifluoromethyl)phenyl]-3-methylbutan-1-one

The titled compound was prepared from the above-mentioned 1-[2-fluoro-4-(trifluoromethyl)phenyl]-3-methylbutanol (600 mg, 2.40 mmol) in a procedure similar to that of Example 9 (1) as a colorless oil (596 mg, yield>99%).

1H NMR (CDCl$_3$, 400 MHz): δ=0.99 (6H, d, J=7 Hz), 2.2-2.4 (1H, m), 2.87 (2H, dd, J=3 Hz, 7 Hz), 7.41 (1H, d, J=10 Hz), 7.49 (1H, d, J=8 Hz), 7.92 (1H, t, J=8 Hz).

(3) Methyl 3-isobutyl-6-(trifluoromethyl)benzothiophene-2-carboxylate

The titled compound was prepared from the above-mentioned 1-[2-fluoro-4-(trifluoromethyl)phenyl]-3-methylbutan-1-one (596 mg, 2.40 mmol) in a procedure similar to that of Reference example 1 (1) as a colorless oil (501 mg, yield 66%).

1H NMR (CDCl$_3$, 400 MHz): δ=0.97 (6H, d, J=7 Hz), 2.0-2.2 (1H, m), 3.22 (2H, d, J=7 Hz), 3.94 (3H, s), 7.62 (1H, d, J=8 Hz), 7.95 (1H, d, J=8 Hz), 8.12 (1H, s).

(4) [3-Isobutyl-6-(trifluoromethyl)benzothiophen-2-yl]-methanol

The titled compound was prepared from the above-mentioned methyl 3-isobutyl-6-(trifluoromethyl)benzothiophen-2-carboxylate (500 mg, 1.58 mmol) in a procedure similar to that of Reference example 1 (2) (380 mg, yield 83%).

1H NMR (CDCl$_3$, 400 MHz): δ=0.95 (6H, d, J=7 Hz), 1.90 (1H, t, J=6 Hz), 1.9-2.1 (1H, m), 2.72 (2H, d, J=7 Hz), 4.96 (2H, d, J=6 Hz), 7.57 (1H, d, J=8 Hz), 7.76 (1H, d, J=8 Hz), 8.10 (1H, s).

(5) 3-Isobutyl-6-(trifluoromethyl)benzothiophen-2-carboxaldehyde

The titled compound was prepared from the above-mentioned [3-isobutyl-6-(trifluoromethyl)benzothiophen-2-yl] methanol (280 mg, 0.971 mmol) in a procedure similar to that of Example 9 (4) as a pale yellow crystal (250 mg, yield 90%).

1H NMR (CDCl$_3$, 400 MHz): δ=1.02 (6H, d, J=7 Hz), 2.0-2.2 (1H, m), 3.14 (2H, d, J=7 Hz), 7.65 (1H, d, J=8 Hz), 7.99 (1H, d, J=8 Hz), 8.17 (1H, s), 10.31 (1H, s).

(6) Methyl 3-[4-[3-[3-isobutyl-6-(trifluoromethyl)benzothiophen-2-yl]propenoyl]-2-methylphenyl]acrylate The titled compound was prepared from the above-mentioned 3-isobutyl-6-(trifluoromethyl)benzothiophen-2-carboxaldehyde (250 mg, 0.873 mmol) and methyl 3-(4-acetyl-2-methylphenyl)acrylate (191 mg, 0.875 mmol) in a procedure similar to that of Example 7 (1) as a yellow crystal (250 mg, yield 71%).

1H NMR (CDCl$_3$, 400 MHz): δ=0.98 (6H, d, J=7 Hz), 1.9-2.1 (1H, m), 2.55 (3H, s), 2.93 (2H, d, J=7 Hz), 3.84 (3H, s), 6.47 (1H, d, J=16 Hz), 7.41 (1H, d, J=15 Hz), 7.60 (1H, d, J=8 Hz), 7.68 (1H, d, J=8 Hz), 7.83 (1H, d, J=8 Hz), 7.8-7.9 (2H, m), 7.99 (1H, d, J=16 Hz), 8.08 (1H, s), 8.16 (1H, d, J=15 Hz).

(7) Methyl 3-[4-[3-[3-isobutyl-6-(trifluoromethyl)benzothiophen-2-yl]propionyl]-2-methylphenylpropionate The titled compound was prepared from the above-mentioned methyl 3-[4-[3-[3-isobutyl-6-(trifluoromethyl)benzothiophen-2-yl]propenoyl]-2-methylphenyl]acrylate (235 mg, 0.483 mmol) in a procedure similar to that of Example 7 (2) as a white crystal (42 mg, yield 14%).

1H NMR (CDCl$_3$, 400 MHz): δ=0.97 (6H, d, J=7 Hz), 1.9-2.1 (1H, m), 2.38 (3H, s), 2.61 (2H, t, J=8 Hz), 2.73 (2H, d, J=7 Hz), 2.99 (2H, d, J=8 Hz), 3.36 (4H, s), 3.68 (3H, s), 7.23 (1H, d, J=8 Hz), 7.54 (1H, d, J=8 Hz), 7.6-7.8 (3H, m), 8.02 (1H, s).

(8) 3-[4-[3-[3-Isobutyl-6-(trifluoromethyl)benzothiophen-2-yl]propionyl]-2-methylphenyl]propionic acid The titled compound was prepared from the above-mentioned methyl 3-[4-[3-[3-isobutyl-6-(trifluoromethyl)benzothiophen-2-yl]propionyl]-2-methylphenylpropionate (40 mg, 81 μmol) in a procedure similar to that of Example 4 (5) as a white crystal (25 mg, yield 64%).

FAB-MS (m/e): 477 (M+1)

1H NMR (CDCl$_3$, 400 MHz): δ=0.97 (6H, d, J=7 Hz), 1.9-2.1 (1H, m), 2.38 (3H, s), 2.67 (2H, t, J=7 Hz), 2.73 (2H, d, J=7 Hz), 3.00 (2H, t, J=7 Hz), 3.36 (4H, s), 7.25 (1H, d, J=7 Hz), 7.54 (1H, d, J=8 Hz), 7.70 (1H, d, J=8 Hz), 7.75 (1H, d, J=8 Hz), 7.77 (1H, s), 8.02 (1H, s).

Example 12

3-[2-methyl-4-[3-[3-isopropyl-6-(trifluoromethyl)benzothiophen-2-yl]propionyl]phenyl]propionic acid

(1) 1-[2-Fluoro-4-(trifluoromethyl)phenyl]-2-methylpropanol

The titled compound was prepared using 0.78M isopropylmagnesium bromide in THF (30 mL) in a procedure similar to that of Example 11 (1) as a pale yellow oil (1.46 g, yield 40%).

1H NMR (CDCl$_3$, 400 MHz): δ=0.89 (3H, d, J=7 Hz), 0.98 (3H, d, J=7 Hz), 1.92 (1H, d, J=5 Hz), 1.9-2.1 (1H, m), 4.81 (1H, t, J=5 Hz), 7.28 (1H, d, J=10 Hz), 7.43 (1H, d, J=8 Hz), 7.60 (1H, t, J=8 Hz).

(2) 1-[2-Fluoro-4-(trifluoromethyl)phenyl]-2-methylpropan-1-one

The titled compound was prepared from the above-mentioned 1-[2-fluoro-4-(trifluoromethyl)phenyl]-2-methylpropanol (1.46 g, 6.18 mmol) in a procedure similar to that of Example 9 (1) as a pale yellow oil (1.1 g, yield 76%).

1H NMR (CDCl$_3$, 400 MHz): δ=1.20 (6H, d, J=7 Hz), 3.3-3.5 (1H, m), 7.41 (1H, d, J=10 Hz), 7.50 (1H, d, J=8 Hz), 7.86 (1H, d, J=8 Hz).

(3) Methyl 3-isopropyl-6-(trifluoromethyl)benzothiophene-2-carboxylate

The titled compound was prepared from the above-mentioned 1-[2-fluoro-4-(trifluoromethyl)phenyl]-2-methylpropan-1-one (1.1 g, 4.7 mmol) in a procedure similar to that of Reference example 1 (1) as a pale yellow oil (820 mg, yield 58%).

1H NMR (CDCl$_3$, 400 MHz): δ=1.50 (6H, d, J=7 Hz), 3.94 (3H, s), 4.4-4.6 (1H, m), 7.59 (1H, dd, J=1 Hz, 8 Hz), 8.12 (1H, s), 8.21 (1H, d, J=8 Hz).

(4) [3-Isopropyl-6-(trifluoromethyl)benzothiophen-2-yl]-methanol

The titled compound was prepared from the above-mentioned methyl 3-isopropyl-6-(trifluoromethyl)benzothiophene-2-carboxylate (720 mg, 2.38 mmol) in a procedure similar to that of Reference example 1 (2) as a pale yellow oil (611 mg, yield 94%).

1H NMR (CDCl$_3$, 400 MHz): δ=1.45 (6H, d, J=7 Hz), 1.95 (1H, t, J=5 Hz), 3.4-3.5 (1H, m), 4.98 (2H, d, J=5 Hz), 7.55 (1H, dd, J=1 Hz, 8 Hz), 7.95 (1H, d, J=8 Hz), 8.09 (1H, s).

(5) 3-Isopropyl-6-(trifluoromethyl)benzothiophen-2-carboxaldehyde

The titled compound was prepared from the above-mentioned [3-isopropyl-6-(trifluoromethyl)benzothiophene-2-yl]methanol (300 mg, 1.09 mmol) in a procedure similar to that of Example 9 (4) as a white crystal (215 mg, yield 72%).

1H NMR (CDCl$_3$, 400 MHz): δ=1.61 (6H, d, J=7 Hz), 3.9-4.1 (1H, m), 7.62 (1H, dd, J=1 Hz, 8 Hz), 8.15 (1H, d, J=8 Hz), 8.16 (1H, s), 10.47 (1H, s).

(6) Methyl 3-[4-[3-[3-isopropyl-6-(trifluoromethyl)-benzothiophen-2-yl]propenoyl]-2-methylphenyl]acrylate The titled compound was prepared from the above-mentioned 3-isopropyl-6-(trifluoromethyl)benzothiophen-2-carboxaldehyde (215 mg, 0.790 mmol) and methyl 3-(4-acetyl-2-methylphenyl)-acrylate (172 mg, 0.788 mmol) in a procedure similar to that of Example 7 (1) as a yellow crystal (259 mg, yield 69%).

1H NMR (CDCl$_3$, 400 MHz): δ=1.53 (6H, d, J=7 Hz), 2.55 (3H, s), 3.7-3.8 (1H, m), 3.84 (3H, s), 6.47 (1H, d, J=16 Hz), 7.42 (1H, d, J=15 Hz), 7.58 (1H, dd, J=1 Hz, 8 Hz), 7.69 (1H, d, J=8 Hz), 7.8-7.9 (2H, m), 8.00 (1H, d, J=16 Hz), 8.05 (1H, d, J=8 Hz), 8.07 (1H, s), 8.30 (1H, d, J=15 Hz).

(7) Methyl 3-[4-[3-[3-isopropyl-6-(trifluoromethyl)-benzothiophen-2-yl]propionyl]-2-methylphenyl] propionate The titled compound was prepared from the above-mentioned methyl 3-[4-[3-[3-isopropyl-6-(trifluoromethyl)benzothiophen-2-yl]propenoyl]-2-methylphenyl]acrylate (213 mg, 0.451 mmol) in a procedure similar to that of Example 7 (2) as a yellow crystal (151 mg, yield 70%).

1H NMR (CDCl$_3$, 400 MHz): δ=1.46 (6H, d, J=7 Hz), 2.37 (3H, s), 2.61 (2H, t, J=8 Hz), 2.99 (2H, t, J=8 Hz), 3.35 (4H, s), 3.4-3.6 (1H, m), 3.68 (3H, s), 7.23 (1H, d, J=8 Hz), 7.52 (1H, d, J=8 Hz), 7.73 (1H, d, J=8 Hz), 7.76 (1H, s), 7.94 (1H, d, J=8 Hz), 8.02 (1H, s).

(8) 3-[4-[3-[3-isopropyl-6-(trifluoromethyl)benzothiophen-2-yl]propionyl]-2-methylphenyl]propionic acid The titled compound was prepared from the above-mentioned methyl 3-[4-[3-[3-isopropyl-6-(trifluoromethyl)benzothiophen-2-yl]propionyl]-2-methylphenyl]-propionate (80 mg, 0.17 mmol) in a procedure similar to that of Example 1 (3) as a pale yellow crystal (60 mg, yield 77%).

FAB-MS (m/e): 463 (M+1)

1H NMR (CDCl$_3$, 400 MHz): δ=1.46 (6H, d, J=7 Hz), 2.38 (3H, s), 2.67 (2H, t, J=8 Hz), 3.00 (2H, t, J=8 Hz), 3.35 (4H, s), 3.4-3.6 (1H, m), 7.25 (1H, d, J=8 Hz), 7.52 (1H, dd, J=2 Hz, 8 Hz), 7.74 (1H, dd, J=2 Hz, 8 Hz), 7.76 (1H, s), 7.94 (1H, d, J=8 Hz), 8.02 (1H, s).

IR (KBr, cm-1): 3033, 2973, 2929, 2630, 1708, 1679, 1608, 1569, 1428, 1409, 1365, 1328, 1280, 1259, 1220, 1159, 1116, 1083, 1056, 1010, 941, 885, 838, 815, 784, 723, 673.

Example 13

3-[4-[1-Hydroxyimino-3-[3-isopropyl-6-(trifluoromethyl)-benzothiophen-2-yl]propyl]-2-methylphenyl] propionic acid

(1) Methyl 3-[4-[1-hydroxyimino-3-[3-isopropyl-6-(trifluoromethyl)benzothiophen-2-yl]propyl]-2-methylphenyl]-propionate To a solution of methyl 3-[4-[3-[3-isopropyl-6-(trifluoromethyl)benzothiophen-2-yl]propionyl]-2-methylphenyl] propionate [Example 12 (7)] (70 mg, 0.15 mmol) in EtOH (1.5 ml) was added a solution of hydroxylamine hydrochloride (11 mg, 0.15 mmol) and sodium acetate (14.5 mg, 0.176 mmol) in water (1 mL). The mixture was heated under reflux for 1 hour, cooled at room temperature, diluted with water, and extracted with ethyl acetate. The organic layer was washed with saturated brine, and dried over anhydrous sodium sulfate. The solvent was removed under reduced pressure, and the residue was recrystallized from ethyl acetate/hexane to give the titled compound as a pale yellow crystal (55 mg, 57%).

1H NMR (CDCl$_3$, 400 MHz): δ=1.44 (6H, d, J=7 Hz), 2.32 (3H, s), 2.59 (2H, t, J=8 Hz), 2.96 (2H, t, J=8 Hz), 3.1-3.3 (4H, m), 3.4-3.5 (1H, m), 3.69 (3H, s), 7.16 (1H, d, J=8 Hz), 7.3-7.4 (2H, m), 7.52 (1H, d, J=8 Hz), 7.94 (1H, d, J=8 Hz), 8.04 (1H, s).

(2) 3-[4-[1-Hydroxyimino-3-[3-isopropyl-6-(trifluoromethyl)benzothiophen-2-yl]propyl]-2-methylphenyl]propionic acid The titled compound was prepared from the above-mentioned methyl 3-[4-[1-hydroxyimino-3-[3-isopropyl-6-(trifluoromethyl)benzothiophen-2-yl]propyl]-2-methylphenyl] propionate (60 mg, 0.12 mmol) in a procedure similar to that of Example 1 (3) as a pale yellow crystal (41 mg, yield 70%).

FAB-MS (m/e): 478 (M+1)

1H NMR (CDCl$_3$, 400 MHz): δ=1.43 (6H, d, J=7 Hz), 2.32 (3H, s), 2.68 (2H, t, J=7 Hz), 2.98 (2H, t, J=7 Hz), 3.1-3.2 (4H, m), 3.4-3.5 (1H, m), 7.20 (1H, d, J=8 Hz), 7.31 (1H, s), 1.33 (1H, d, J=8 Hz), 7.52 (1H, d, J=8 Hz), 7.94 (1H, d, J=8 Hz), 8.03 (1H, s).

IR (KBr, cm-1): 3072, 2964, 2927, 2869, 1702, 1616, 1535, 1506, 1454, 1409, 1380, 1326, 1278, 1230, 1162, 1110, 1089, 1068, 1014, 981, 892, 846, 806, 755, 730, 671, 611.

Example 14

3-[4-[1-[2-[3-Isopropyl-6-(trifluoromethyl)-benzothiophen-2-yl]ethyl]vinyl]-2-methylphenyl]propionic acid

(1) Methyl 3-[4-[1-[2-[3-isopropyl-6-(trifluoromethyl)-benzothiophen-2-yl]ethyl]vinyl]-2-methylphenyl]propionate To a suspension of trimethylphosphonium bromide (84 mg, 0.24 mmol) in THF (4 mL) was added sodium amide (12 mg, 0.31 mmol) under N$_2$ atmosphere. The mixture was stirred for 30 minutes at room temperature, to which was added a solution of methyl 3-[4-[3-[3-isopropyl-6-(trifluoromethyl)benzothiophen-2-yl]propionyl]-2-methylphenyl] propionate [Example 12 (7)] (75 mg, 0.16 mmol) in THF (1 mL). The mixture was stirred for 22 hours at room temperature, treated with saturated aqueous ammonium chloride solution, and extracted with ethyl acetate. The organic layer was washed with saturated brine, and dried over anhydrous sodium sulfate. The solvent was removed under reduced pressure, and the residue was purified by silica gel column chromatography (hexane/ethyl acetate=7/1), to give the titled compound as a pale yellow oil (27 mg, yield 36%).

1H NMR (CDCl$_3$, 400 MHz): δ 1.41 (6H, d, J=7 Hz), 2.34 (3H, s), 2.61 (2H, t, J=8 Hz), 2.86 (2H, t, J=8 Hz), 2.96 (2H, t, J=8 Hz), 3.04 (2H, t, J=8 Hz), 3.2-3.4 (1H, m), 3.70 (3H, s), 5.08 (1H, s), 5.32 (1H, s), 7.13 (1H, d, J=8 Hz), 7.22 (1H, d, J=8 Hz), 7.23 (1H, s), 7.51 (1H, d, J=8 Hz), 7.93 (1H, d, J=8 Hz), 8.03 (1H, s).

(2) 3-[4-[1-[2-[3-Isopropyl-6-(trifluoromethyl)benzothiophen-2-yl]ethyl]vinyl]-2-methylphenyl]propionic acid The titled compound was prepared from the above-mentioned methyl 3-[4-[1-[2-[3-isopropyl-6-(trifluoromethyl) benzothiophen-2-yl]ethyl]vinyl]-2-methylphenyl]-propionate (27 mg, 57 µmol) in a procedure similar to that of Example 1 (3) as a yellow oil (27 mg, yield>99%).

FAB-MS (m/e): 461 (M+1)

1H NMR (CDCl$_3$, 400 MHz): δ=1.41 (6H, d, J=7 Hz), 2.35 (3H, s), 2.67 (2H, t, J=7 Hz), 2.86 (2H, dd, J=7 Hz, 8 Hz), 2.98 (2H, t, J=7 Hz), 3.03 (2H, dd, J=7 Hz, 8 Hz), 3.2-3.4 (1H, m), 5.08 (1H, s), 5.32 (1H, s), 7.15 (1H, d, J=8 Hz), 7.2-7.3 (2H, m), 7.52 (1H, dd, J=1 Hz, 8 Hz), 7.93 (1H, d, J=8 Hz), 8.03 (1H, s).

Example 15

4-[3-[3-Isopropyl-6-(trifluoromethyl)benzothiophen-2-yl]-propionyl]-2-methylphenoxyacetic acid

(1) 1-(4-Hydroxy-3-methylphenyl)-3-[3-isopropyl-6-(trifluoromethyl)benzothiophen-2-yl]propan-1-one The titled compound was prepared from 3-isopropyl-6-(trifluoromethyl)benzothiophene-2-methanol (1.0 g, 3.6 mmol) in a procedure similar to that of Example 1 (1) as a yellow crystal (820 mg, yield 57%).

1H NMR (CDCl$_3$, 400 MHz): δ=1.46 (6H, d, J=7 Hz), 2.28 (3H, s), 3.2-3.4 (4H, m), 3.4-3.6 (1H, m), 5.31 (1H, br s), 6.81 (1H, d, J=8 Hz), 7.52 (1H, d, J=8 Hz), 7.74 (1H, dd, J=2 Hz, 8 Hz), 7.79 (1H, s), 7.94 (1H, d, J=8 Hz), 8.02 (1H, s).

(2) Ethyl 4-[3-[3-isopropyl-6-(trifluoromethyl)benzothiophen-2-yl]propionyl]-2-methylphenoxyacetate The titled compound was prepared from the above-mentioned 1-(4-hydroxy-3-methylphenyl)-3-[3-isopropyl-6-(trifluoromethyl)benzothiophen-2-yl]propan-1-one (600 mg, 1.48 mmol) in a procedure similar to that of Example 1 (2) as a pale yellow oil (727 mg, yield>99%).

1H NMR (CDCl3, 400 MHz): δ=1.28 (3H, t, J=7 Hz), 1.45 (6H, d, J=7 Hz), 2.31 (3H, s), 3.2-3.4 (4H, m), 3.4-3.5 (1H, m), 4.24 (2H, q, J=7 Hz), 4.69 (2H, s), 6.70 (1H, d, J=8 Hz), 7.51 (1H, d, J=8 Hz), 7.78 (1H, d, J=8 Hz), 7.80 (1H, s), 7.93 (1H, d, J=8 Hz), 8.01 (1H, s).

(3) 4-[3-[3-Isopropyl-6-(trifluoromethyl)benzothiophen-2-yl]-propionyl]-2-methylphenoxyacetic acid The titled compound was prepared from the above-mentioned ethyl 4-[3-[3-isopropyl-6-(trifluoromethyl)-benzothiophen-2-yl]propionyl]-2-methylphenoxyacetate (70 mg, 0.14 mmol) in a procedure similar to that of Example 1 (3) as a white crystal (43 mg, yield 65%).

FAB-MS (m/e): 465 (M+1)

1H NMR (CDCl$_3$, 400 MHz): δ=1.46 (6H, d, J=7 Hz), 2.32 (3H, s), 3.2-3.4 (4H, m), 3.4-3.5 (1H, m), 4.77 (2H, s), 6.75 (1H, d, J=8 Hz), 7.52 (1H, d, J=8 Hz), 7.7-7.9 (2H, m), 7.94 (1H, d, J=8 Hz), 8.02 (1H, s).

IR (KBr, cm-1): 2964, 2927, 2792, 2584, 1749, 1670, 1600, 1581, 1506, 1427, 1402, 1365, 1328, 1278, 1245, 1184, 1159, 1132, 1116, 1083, 1056, 1012, 887, 813, 723, 682.

Example 16

4-[1-Hydroxyimino-3-[3-isopropyl-6-(trifluoromethyl)-benzothiophen-2-yl]propyl]-2-methyl-phenoxyacetic acid

(1) Ethyl 4-[1-hydroxyimino-3-[3-isopropyl-6-(trifluoromethyl)benzothiophen-2-yl]propyl]-2-methylphenoxyacetate The titled compound was prepared from ethyl 4-[3-[3-isopropyl-6-(trifluoromethyl)benzothiophen-2-yl]propionyl]-2-methylphenoxyacetate [Example 15 (2)] (400 mg, 0.812 mmol) in a procedure similar to that of Example 13 (1) as a pale yellow oil (316 mg, yield 77%).

1H NMR (CDCl$_3$, 400 MHz): δ=1.30 (3H, t, J=7 Hz), 1.44 (6H, d, J=7 Hz), 2.29 (3H, s), 3.0-3.2 (4H, m), 3.4-3.5 (1H, m), 4.27 (2H, q, J=7 Hz), 4.66 (2H, s), 6.70 (1H, d, J=8 Hz), 7.38 (1H, dd, J=2 Hz, 8 Hz), 7.42 (1H, s), 7.52 (1H, dd, J=2 Hz, 8 Hz), 7.94 (1H, d, J=8 Hz), 8.04 (1H, s).

(2) 4-[1-Hydroxyimino-3-[3-isopropyl-6-(trifluoromethyl)-benzothiophen-2-yl]propyl]-2-methylphenoxyacetic acid The titled compound was prepared from the above-mentioned ethyl 4-[1-hydroxyimino-3-[3-isopropyl-6-(trifluoromethyl)-benzothiophen-2-yl]propyl]-2-methylphenoxyacetate (60 mg, 0.12 mmol) in a procedure similar to that of Example 1 (3) as a grayish white crystal (36 mg, yield 64%).

FAB-MS (m/e): 480 (M+1)

1H NMR (CDCl$_3$, 400 MHz): δ=1.42 (6H, d, J=7 Hz), 2.27 (3H, s), 3.1-3.2 (4H, m), 3.3-3.5 (1H, m), 4.76 (2H, s), 6.76 (1H, d, J=8 Hz), 7.2-7.4 (2H, m), 7.52 (1H, d, J=8 Hz), 7.94 (1H, d, J=8 Hz), 8.03 (1H, s).

IR (KBr, cm-1): 3471, 2969, 2931, 2875, 1751, 1720, 1606, 1581, 1508, 1452, 1432, 1405, 1324, 1278, 1253, 1228, 1199, 1164, 1145, 1118, 1081, 1056, 970, 883, 821, 723.

Example 17

4-[3-[3-Isopropyl-6-(trifluoromethyl)benzothiophen-2-yl]-1-methoxyiminopropyl]-2-methylphenoxyacetic acid

(1) Ethyl 4-[3-[3-isopropyl-6-(trifluoromethyl)benzothiophen-2-yl]-1-methoxyiminopropyl]-2-methylphenoxyacetate The titled compound was prepared from ethyl 4-[3-[3-isopropyl-6-(trifluoromethyl)benzothiophen-2-yl]propionyl]-2-methylphenoxyacetate [Example 15 (2)] (70 mg, 0.14 mmol) and methoxyamine hydrochloride (13 mg, 0.16 mmol) in a procedure similar to that of Example 13 (1) as a yellow oil (74 mg, yield>99%).

1H NMR (CDCl$_3$, 400 MHz): δ=1.29 (3H, t, J=7 Hz), 1.44 (6H, d, J=7 Hz), 2.29 (3H, s), 3.0-3.2 (4H, m), 3.3-3.5 (1H, m), 3.99 (3H, s), 4.26 (2H, q, J=7 Hz), 4.65 (2H, s), 6.68 (1H, d, J=8 Hz), 7.38 (1H, dd, J=1 Hz, 8 Hz), 7.46 (1H, s), 7.52 (1H, dd, J=1 Hz, 8 Hz), 7.94 (1H, d, J=8 Hz), 8.04 (1H, s).

(2) 4-[3-[3-Isopropyl-6-(trifluoromethyl)benzothiophen-2-yl]-1-methoxyiminopropyl]-2-methylphenoxyacetic acid The titled compound was prepared from ethyl 4-[3-[3-isopropyl-6-(trifluoromethyl)benzothiophen-2-yl]-1-methoxyiminopropyl]-2-methylphenoxyacetate (74 mg, 0.14 mmol) in a procedure similar to that of Example 1 (3) as a pale yellow crystal (20 mg, yield 29%).

FAB-MS (m/e): 494 (M+1)

1H NMR (CDCl$_3$, 400 MHz): δ=1.44 (6H, d, J=7 Hz), 2.28 (3H, s), 3.0-3.2 (4H, m), 3.3-3.5 (1H, m), 3.99 (3H, s), 4.71 (2H, s), 6.73 (1H, d, J=8 Hz), 7.41 (1H, dd, J=2 Hz, 8 Hz), 7.47 (1H, s), 7.52 (1H, d, J=8 Hz), 7.94 (1H, d, J=8 Hz), 8.03 (1H, s).

Example 18

4-[1-Benzyloxyimino-3-[3-isopropyl-6-(trifluoromethyl)-benzothiophen-2-yl]propyl]-2-methylphenoxyacetic acid

(1) Ethyl 4-[1-benzyloxyimino-3-[3-isopropyl-6-(trifluoromethyl)benzothiophen-2-yl]propyl]-2-methylphenoxyacetate To an ice-cold solution of ethyl 4-[1-hydroxyimino-3-[3-isopropyl-6-(trifluoromethyl)benzothiophen-2-yl]propyl]-2-methylphenoxyacetate [Example 16 (1)] (90 mg, 0.18 mmol) in THF (1.8 mL) was added 55% sodium hydride (12 mg, 0.27 mmol). The mixture was stirred for 10 minutes, to which was added benzyl bromide (0.03 mL, 0.3 mmol). The mixture was stirred for 72 hours at room temperature, treated with saturated aqueous ammonium chloride solution, and extracted with ethyl acetate. The organic layer was washed with saturated brine, and dried over anhydrous sodium sulfate. The solvent was removed under reduced pressure, and the residue was purified by silica gel column chromatography (hexane/ethyl acetate=7/1), to give the titled compound as a colorless oil (25 mg, yield 24%).

1H NMR (CDCl$_3$, 400 MHz): δ=1.30 (3H, t, J=7 Hz), 1.31 (6H, d, J=7 Hz), 2.29 (3H, s), 3.0-3.2 (4H, m), 3.2-3.4 (1H, m), 4.27 (2H, q, J=7 Hz), 4.65 (2H, s), 5.22 (2H, s), 6.69 (1H, d, J=8 Hz), 7.3-7.4 (5H, m), 7.40 (1H, dd, J=2 Hz, 8 Hz), 7.47 (1H, d, J=2 Hz), 7.50 (1H, d, J=8 Hz), 7.90 (1H, d, J=8 Hz), 8.01 (1H, s).

(2) 4-[1-Benzyloxyimino-3-[3-isopropyl-6-(trifluoromethyl)benzothiophen-2-yl]propyl]-2-methylphenoxyacetic acid The titled compound was prepared from the above-mentioned ethyl 4-[1-benzyloxyimino-3-[3-isopropyl-6-(trifluoromethyl)benzothiophen-2-yl]propyl]-2-methylphenoxyacetate (25 mg, 42 μmol) in a procedure similar to that of Example 1 (3) as a pale white crystal (13 mg, yield 55%).

FAB-MS (m/e): 570 (M+1)

1H NMR (CDCl$_3$, 400 MHz): δ=1.30 (6H, d, J=7 Hz), 2.29 (3H, s), 3.0-3.2 (4H, m), 3.2-3.4 (1H, m), 4.71 (2H, s), 5.22 (2H, s), 6.73 (1H, d, J=8 Hz), 7.3-7.4 (5H, m), 7.42 (1H, dd, J=2 Hz, 8 Hz), 7.4-7.6 (2H, m), 7.90 (1H, d, J=8 Hz), 8.01 (1H, s).

Example 19

[3-[2-[3-Isopropyl-6-(trifluoromethyl)benzothiophen-2-yl]-ethyl]-5-methyl-benzisoxazol-6-yloxy]acetic acid

(1) 2-Chloromethyl-3-isopropyl-6-(trifluoromethyl)-benzothiophene

To a solution of 3-isopropyl-6-(trifluoromethyl)-benzothiophene-2-methanol (obtained in Example 12(4), 878 mg, 3.20 mmol) in benzene (27 mL) was added dropwise a solution of thionyl chloride (0.28 mL, 3.8 mmol) in benzene (5 mL) under cooling with ice. The mixture was stirred for 3 hours at room temperature. After the solvent was removed under reduced pressure, the residue was purified by chromatography on silica gel (hexane/ethyl acetate, 10:1) to give the titled compound as a pale yellow oil (655 mg, y. 70%).

$^1$H-NMR (CDCl$_3$, 400 MHz) δ: 1.50 (6H, d, J=7 Hz), 3.4-3.6 (1H, m), 4.87 (2H, s), 7.56 (1H, d, J=8 Hz), 8.01 (1H, d, J=8 Hz), 8.78 (1H, s)

(2) N-[3-[2-[3-Isopropyl-6-(trifluoromethyl)benzothiophen-2-yl]ethyl]-5-methylbenzisoxazol-6-yl]acetamide To a suspension of N-(3,5-dimethylbenzisoxazol-6-yl)acetamide (381 mg, 1.87 mmol) in anhydrous THF (15 mL) was added dropwise 2M LDA (2.3 mL, 4.6 mmol) for 30 min at −78° C. under N$_2$ atmosphere. The mixture was stirred for 30 min at −78° C., to which a solution of 2-chloromethyl-3-isopropyl-6-(trifluoromethyl)benzothiophene (655 mg, 2.24 mmol) in THF (5.0 mL) was added dropwise for 30 min. The mixture was stirred for 2 h at the same temperature, and then warmed to room temperature. A saturated aqueous ammonium chloride and ethyl acetate were added to the reaction mixture. The organic layer was washed with water, brine, and dried over anhydrous sodium sulfate. After the solvent was removed under reduced pressure, the residue was purified by silica gel column chromatography (hexane/ethyl acetate, 1:1) to give the titled compound as a pale yellow crystal (426 mg, yield. 50%).

$^1$H-NMR (CDCl$_3$, 400 MHz) δ: 1.34 (6H, d, J=7 Hz), 2.24 (3H, s), 2.26 (3H, br s), 3.31 (2H, t, J=8 Hz), 3.3-3.4 (1H, m), 3.46 (2H, t, J=8 Hz), 7.09 (1H, br s), 7.19 (1H, s), 7.54 (1H, d, J=8 Hz), 7.93 (1H, d, J=8 Hz), 8.05 (1H, s), 8.40 (1H, br s).

(3) 6-Amino-3-[2-[3-isopropyl-6-(trifluoromethyl) benzothiophen-2-yl]ethyl]-5-methylbenzisoxazole The above-mentioned N-[3-[2-[3-Isopropyl-6-(trifluoromethyl)benzothiophen-2-yl]ethyl]-5-methylbenzisoxazol-6-yl]acetamide (326 mg, 0.708 mmol) was dissolved in 1M HCl (3.0 mL) and AcOH (7.0 mL). The solution was heated under reflux for 23 hours. Then reaction mixture was cooled to room temperature, diluted with 4M NaOH, and extracted with ethyl acetate. The organic layer was washed with brine, dried over anhydrous sodium sulfate. After the solvent was removed under reduced pressure, the residue was purified by silica gel column chromatography (hexane/ethyl acetate, 2:1) to give the title compound as a brown crystal (201 mg, yield: 68%).

$^1$H-NMR (CDCl$_3$, 400 MHz) δ: 1.36 (6H, d, J=7 Hz), 2.15 (3H, s), 3.26 (2H, t, J=8 Hz), 3.3-3.5 (1H, m), 3.4-3.5 (2H, m), 3.99 (2H, br s), 6.74 (1H, s), 7.09 (1H, s), 7.52 (1H, d, J=8 Hz), 7.93 (1H, d, J=8 Hz), 8.05 (1H, s).

(4) 3-[2-[3-Isopropyl-6-(trifluoromethyl)benzothiophen-2-yl]-ethyl]-6-hydroxy-5-methylbenzisoxazole The above-mentioned 6-amino-3-[2-[3-isopropyl-6-(trifluoromethyl)benzothiophen-2-yl]ethyl]-5-methylbenzisoxazole (100 mg, 0.239 mmol) was suspended in 25% H$_2$SO$_4$ (2.0 mL). A solution of sodium nitrite (25 mg, 0.36 mmol) in water (1.0 mL) was added to the suspension under cooling with ice. After the mixture was stirred for 30 min under the same conditions, and added dropwise to 75% H$_2$SO$_4$ (1.5 mL) that heated to 120° C. The mixture was heated for 1 h at 120° C., cooled to room temperature, diluted with ice-cold water, and extracted with ethyl acetate. The organic layer was washed with brine and dried over anhydrous sodium sulfate. After the solvent was removed, the residue was purified by silica gel column chromatography (hexane/ethyl acetate, 5:1) to give the titled compound (20 mg) as yellow crystal (20 mg, yield 20%).

$^1$H-NMR (CDCl$_3$, 400 MHz) δ: 1.36 (6H, d, J=7 Hz), 2.23 (3H, s), 3.2-3.5 (5H, m), 6.94 (1H, s), 7.37 (1H, s), 7.53 (1H, d, J=8 Hz), 7.93 (1H, d, J=8 Hz), 8.04 (1H, s).

(5) Ethyl 3-[2-[3-isopropyl-6-(trifluoromethyl)benzothiophen-2-yl]ethyl]-5-methylbenzisoxazol-6-yloxyacetate The titled compound was prepared from the above-mentioned 3-[2-[3-isopropyl-6-(trifluoromethyl)benzothiophen-2-yl]ethyl]-6-hydroxy-5-methylbenzisoxazole (20 mg, 0.048 mmol) in a procedure similar to that of Example 1 (2) as a yellow oil (14 mg, yield 60%).

$^1$H-NMR (CDCl$_3$, 400 MHz) δ: 1.26 (3H, t, J=7 Hz), 1.35 (6H, d, J=7 Hz), 2.27 (3H, s), 3.2-3.5 (5H, m), 4.27 (2H, q, J=7 Hz), 4.71 (2H, s), 6.72 (1H, s), 7.18 (1H, s), 7.52 (1H, d, J=8 Hz), 7.93 (1H, d, J=8 Hz), 8.18 (1H, s).

(6) 3-[2-[3-Isopropyl-6-(trifluoromethyl)benzothiophen-2-yl]-ethyl]-5-methylbenzisoxazol-6-yloxyacetic acid The titled compound was prepared from the above-mentioned ethyl 3-[2-[3-isopropyl-6-(trifluoromethyl)-benzothiophen-2-yl]ethyl]-5-methylbenzisoxazol-6-yloxyacetate (14 mg, 28 μmol) in a procedure similar to that of Example 1 (3) as a pale yellow crystal (3 mg, yield 23%)

FAB-MS (m/e): 478 (M+1)

$^1$H-NMR (CDCl$_3$, 400 MHz) δ: 1.36 (6H, d, J=7 Hz), 2.27 (3H, s), 3.30 (2H, dd, J=7 Hz, J=8 Hz), 3.3-3.5 (1H, m), 3.46 (2H, dd, J=7 Hz, J=8 Hz), 4.78 (2H, s), 6.87 (1H, s), 7.23 (1H, d, J=8 Hz), 7.52 (1H, d, J=8 Hz), 7.93 (1H, d, J=8 Hz), 8.05 (1H, s).

Example 20

N-[3-[2-[3-Isopropyl-6-(trifluoromethyl)benzothiophen-2-yl]ethyl]-5-methylbenzisoxazol-6-yl]-N-methylglycine

(1) 3-[2-[3-Isopropyl-6-(trifluoromethyl)benzothiophen-2-yl]-ethyl]-5-methyl-6-methylaminobenzisoxazole N-[3-[2-[3-Isopropyl-6-(trifluoromethyl)benzothiophen-2-yl]-ethyl]-5-methylbenzisoxazol-6-yl]acetamide (100 mg, 0.217 mmol) obtained above was dissolved in anhydrous DMF (1.0 mL). To the resulting solution was added 60% sodium hydride (10 mg, 0.26 mmol) under ice-cooling. The mixture was then stirred for 10 minutes under the same temperature and methyl iodide (0.027 mL, 0.43 mmol) was added. The mixture was stirred for 3 hours under the same temperature, diluted with water, and extracted with ethyl acetate. The organic layer was collected, washed with brine, and dried over anhydrous sodium sulfate. The solvent was removed under reduced pressure, to give N-[3-[2-[3-isopropyl-6-(trifluoromethyl)benzothiophen-2-yl]ethyl]-5-methylbenzisoxazol-6-yl]-N-methylacetamide as a brown oil. The titled compound was prepared from the above-mentioned N-[3-[2-[3-isopropyl-6-(trifluoromethyl)benzothiophen-2-yl]ethyl]-5-methylbenzisoxazol-6-yl]-N-methylacetamide in a procedure similar to that of Example 19-(3) as a brown oil (39 mg, yield 42%).

$^1$H-NMR (CDCl$_3$, 400 MHz) δ: 1.37 (6H, d, J=7 Hz), 2.11 (3H, s), 2.95 (3H, s), 3.25 (2H, t, J=8 Hz), 3.3-3.5 (1H, m), 3.4-3.5 (2H, m), 4.03 (1H, br s), 6.59 (1H, s), 7.06 (1H, s), 7.52 (1H, d, J=8 Hz), 7.93 (1H, d, J=8 Hz), 8.04 (1H, s).

(2) N-[3-[2-[3-Isopropyl-6-(trifluoromethyl)benzothiophen-2-yl]ethyl]-5-methylbenzisoxazol-6-yl]-N-methylglycine ethyl ester To a solution of 3-[2-[3-isopropyl-6-(trifluoromethyl)-benzothiophen-2-yl]ethyl]-5-methyl-6-methylaminobenzisoxazole (39 mg, 90 μmol) obtained above and diisopropylethylamine (80 μL, 0.45 mmol) in anhydrous DMF (0.45 mL) was added ethyl bromoacetate (50 μL, 0.45 mmol). The mixture was heated for 21 hours at 110° C. and cooled to room temperature. Water was added to reaction mixture and extracted with ethyl acetate. The organic layer was washed with brine, dried over anhydrous sodium sulfate, and then the solvent was removed under reduced pressure. The residue was purified by silica gel column chromatography (hexane/chloroform, 5:1) to give the title compound as a yellow oil (35 mg, yield 75%).

$^1$H-NMR (CDCl$_3$, 400 MHz) δ: 1.30 (3H, t, J=7 Hz), 1.35 (6H, d, J=7 Hz), 2.28 (3H, s), 2.94 (3H, s), 3.29 (2H, dd, J=5 Hz, J=8 Hz), 3.3-3.5 (1H, m), 3.45 (2H, dd, J=5 Hz, 8 Hz), 3.77 (2H, s), 4.25 (2H, q, J=7 Hz), 7.19 (1H, s), 7.20 (1H, s), 7.52 (1H, d, J=8 Hz), 7.93 (1H, d, J=8 Hz), 8.05 (1H, s).

(3) N-[3-[2-[3-Isopropyl-6-(trifluoromethyl)benzothiophen-2-yl]ethyl]-5-methylbenzisoxazol-6-yl]-N-methylglycine The titled compound was prepared from the above-mentioned N-[3-[2-[3-isopropyl-6-(trifluoromethyl)benzothiophen-2-yl]ethyl]-5-methylbenzisoxazol-6-yl]-N-methylglycine ethyl ester (35 mg, 68 μmol) in a procedure similar to that of Example 1 (3) as a pale yellow crystal (15 mg, yield 45%).

FAB-MS (m/e): 491 (M+1)

$^1$H-NMR (CDCl$_3$, 400 MHz) δ: 1.35 (6H, d, J=7 Hz), 2.30 (3H, s), 2.91 (3H, s), 3.31 (2H, dd, J=7 Hz, 8 Hz), 3.3-3.4 (1H, m), 3.46 (2H, dd, J=7 Hz, 8 Hz), 3.80 (2H, s), 7.2-7.3 (2H, m), 7.52 (1H, d, J=8 Hz), 7.93 (1H, d, J=8 Hz), 8.05 (1H, s).

Example 21

3-[3-[2-[3-Isopropyl-6-(trifluoromethyl)benzothiophen-2-yl]-ethyl]-5-methylbenzisoxazol-6-yl]propionic acid

(1) Methyl 2-bromo-3-[3-[2-[3-isopropyl-6-(trifluoromethyl)benzothiophen-2-yl]ethyl-5-methylbenzisoxazol-6-yl]propionate To a solution of 6-amino-[3-[2-[3-isopropyl-6-(trifluoromethyl)benzothiophen-2-yl]ethyl]-5-methyl]benzisoxazole (150 mg, 0.358 mmol) in methanol (1 mL)-acetone (2 mL) was added 48% HBr (0.17 mL, 1.4 mmol) under ice-cooling, and then the solution of sodium nitrite (30 mg, 0.43 mmol) in water (1.0 mL) was added to the resultant solution. The mixture was stirred for 2 hours under ice-cooling, and raised to room temperature. Methyl acrylate (0.23 mL, 2.5 mmol) and copper (I) oxide (5.0 mg) were added to the mixture. The resulting mixture was stirred at 40° C. for 30 minutes. After the solvent was removed, the saturated aqueous sodium bicarbonate solution was added to the resultant mixture, and the mixture was extracted with ethyl acetate. The organic layer was washed with brine, and dried over anhydrous sodium sulfate. After the solvent was removed, the residue was purified by silica gel column chromatography (hexane/ethyl acetate, 5:1) to give the titled compound as a pale yellow crystal (135 mg, yield 66%).

$^1$H-NMR (CDCl$_3$, 400 MHz) δ: 1.33 (6H, dd, J=1 Hz, 7 Hz), 2.33 (3H, s), 3.3-3.4 (4H, m), 3.47 (2H, dd, J=5 Hz, 8 Hz), 3.57 (1H, dd, J=5 Hz, 8 Hz), 3.75 (3H, s), 4.42 (1H, dd, J=7 Hz, 8 Hz), 7.23 (1H, s), 7.37 (1H, s), 7.52 (1H, dd, J=1 Hz, 8 Hz), 7.92 (1H, d, J=8 Hz), 8.05 (1H, s).

(2) Methyl 3-[3-[2-[3-isopropyl-6-(trifluoromethyl)benzothiophen-2-yl]ethyl]-5-methylbenzisoxazol-6-yl]acrylate To a solution of the above-mentioned methyl 2-bromo-3-[3-[2-[3-isopropyl-6-(trifluoromethyl)benzothiophen-2-yl]ethyl-5-methyl-benzisoxazol-6-yl]propionate (135 mg, 0.238 mmol) in MeOH (1.2 mL) was added triethylamine (70 μL, 0.48 mmol). The mixture was heated for 19 hours under reflux and cooled to room temperature, diluted with saturated aqueous ammonium chloride solution and 1M HCl, and extracted with ethyl acetate. The organic layer was collected, washed with brine, dried over anhydrous sodium sulfate. The solvent was removed under reduced pressure to give the titled compound as a brown oil (104 mg, yield 90%).

$^1$H-NMR (CDCl$_3$, 400 MHz) δ: 1.35 (6H, d, J=7 Hz), 2.41 (3H, s), 3.3-3.5 (3H, m), 3.48 (2H, dd, J=5, 8 Hz), 3.83 (3H, s), 6.44 (1H, d, J=16 Hz), 7.27 (1H, s), 7.53 (1H, d, J=8 Hz), 7.69 (1H, s), 7.93 (1H, d, J=8 Hz), 7.99 (1H, d, J=16 Hz), 8.05 (1H, s).

(3) 3-[3-[2-[3-Isopropyl-6-(trifluoromethyl)benzothiophen-2-yl]ethyl]-5-methylbenzisoxazol-6-yl]acrylic acid The titled compound (75 mg, yield 72%) was prepared from the above-mentioned methyl 3-[3-[2-[3-isopropyl-6-(trifluoromethyl)benzothiophen-2-yl]ethyl]-5-methylbenzisoxazol-6-yl]acrylate (104 mg, 0.213 mmol) in a procedure similar to that of Example 1 (3).

$^1$H-NMR (CDCl$_3$, 400 MHz) δ: 1.35 (6H, d, J=7 Hz), 2.42 (3H, s), 3.3-3.4 (3H, m), 3.49 (2H, dd, J=5, 8 Hz), 6.47 (1H, d, J=16 Hz), 7.28 (1H, s), 7.53 (1H, d, J=8 Hz), 7.74 (1H, s), 7.93 (1H, d, J=8 Hz), 8.05 (1H, s), 8.09 (1H, d, J=16 Hz).

(4) 3-[3-[2-[3-Isopropyl-6-(trifluoromethyl)benzothiophen-2-yl]ethyl]-5-methylbenzisoxazol-6-yl]propionic acid To a solution of the above-mentioned 3-[3-[2-[3-isopropyl-6-(trifluoromethyl)benzothiophen-2-yl]ethyl]-5-methylbenzisoxazol-6-yl]acrylic acid (75 mg, 0.15 mmol) in MeOH (0.8 mL) was added hydrazine monohydrate (0.15 mL, 3.1 mmol). The mixture was heated reflux for 4 hours, cooled to room temperature, diluted with ice-water and 1M HCl, and extracted with ethyl acetate. The organic layer was collected, washed with brine, dried over anhydrous sodium sulfate. The solvent was removed under reduced pressure to give the titled compound as a brown oil (57 mg, yield 78%).

FAB-MS (m/e): 476 (M+1)

$^1$H-NMR (CDCl$_3$, 400 MHz) δ: 1.35 (6H, d, J=7 Hz), 2.32 (3H, s), 2.71 (2H, t, J=7 Hz), 3.07 (2H, t, J=7 Hz), 3.32 (2H, dd, J=7 Hz, 8 Hz), 3.3-3.5 (1H, m), 3.47 (2H, dd, J=7 Hz, 8 Hz), 7.25 (1H, d, J=8 Hz), 7.36 (1H, s), 7.52 (1H, d, J=8 Hz), 7.93 (1H, d, J=8 Hz), 8.04 (1H, s).

IR (KBr, cm$^{-1}$): 2975, 2929, 1702, 1436, 1328, 1303, 1259, 1234, 1213, 1162, 1153, 1116, 1083, 883, 869, 815, 721, 418.

Example 22

5-Hydroxy-2-methyl-4-[3-propyl-6-(trifluoromethyl)benzothiophen-2-yl]propionyl]phenoxyacetic acid

(1) 1-(2,4-Dibenzyloxy-5-methylphenyl)-3-[3-propyl-6-(trifluoromethyl)benzothiophen-2-yl]propenone To a solution of 1-(2,4-Dibenzyloxy-5-methylphenyl)-ethanone (128 mg, 0.368 mmol) in anhydrous THF (2 mL) was added dropwise 0.5M MeONa (0.9 mL, 0.44 mmol) under ice-cooling. The solution was stirred for 10 minutes under same temperature, and then a solution of 3-propyl-6-(trifluoromethyl)benzothiophen-2-carboxaldehyde (100 mg, 0.368 mmol) in anhydrous THF (1.7 mL) was added to the resultant solution. The mixture was stirred for 2.5 hours, and added 0.5 M MeONa/MeOH (2.2 mL, 1.1 mmol). The mixture was stirred at room temperature for 17.5 hours and heated reflux for 3 hours. And the mixture was cooled to room temperature, neutralized with 1M HCl under ice-cooling, and extracted with ethyl acetate. The organic layer was washed with brine, and dried over anhydrous sodium sulfate. After the solvent was removed, the residue was washed with hexane to give the titled compound as a yellow crystal (154 mg, yield 70%).

$^1$H-NMR (CDCl$_3$, 400 MHz) δ: 0.98 (3H, t, J=7 Hz), 1.67 (2H, q, J=7 Hz), 2.25 (3H, s), 2.98 (2H, t, J=7 Hz), 5.13 (4H, s), 6.56 (1H, s), 7.3-7.4 (4H, m), 7.4-7.5 (6H, m), 7.55 (1H, d, J=9 Hz), 7.61 (1H, d, J=15 Hz), 7.72 (1H, s), 7.78 (1H, d, J=9 Hz), 7.96 (1H, s), 8.01 (1H, d, J=15 Hz).

(2) 1-(2,4-Dihydroxy-5-methylphenyl)-3-[3-propyl-6-(trifluoromethyl)benzothiophen-2-yl]propenone To a solution of the above-mentioned 1-(2,4-dibenzyloxy-5-methylphenyl)-3-[3-propyl-6-(trifluoromethyl)benzothiophen-2-yl]propenone (100 mg, 0.166 mmol) in AcOH (4.0 mL) was added conc HCl (2.0 mL). The mixture was heated for 23 hours under reflux, and then allowed to cool to room temperature and added ice-water. The mixture was neutralized with saturated aqueous sodium bicarbonate solution, and extracted with ethyl acetate. The organic layer was washed with brine, dried over anhydrous sodium sulfate. After the solvent was removed, the residue was purified by silica gel column chromatography (hexane/ethyl acetate, 5:1) to give the titled compound as a pale yellow crystal (66 mg, yield 94%).

$^1$H-NMR (CDCl$_3$, 400 MHz) δ: 1.01 (3H, t, J=7 Hz), 1.7-1.8 (2H, m), 2.27 (3H, s), 3.05 (2H, t, J=7 Hz), 6.41 (1H, s), 7.36 (1H, s), 7.45 (1H, d, J=15 Hz), 7.60 (1H, d, J=9 Hz), 7.84 (1H, d, J=9 Hz), 8.08 (1H, s), 8.21 (1H, d, J=15 Hz), 8.20 (1H, s).

(3) 1-(2,4-Dihydroxy-5-methylphenyl)-3-[3-propyl-6-(trifluoromethyl)benzothiophen-2-yl]propan-1-one 1-(2,4-Dihydroxy-5-methylphenyl)-3-[3-propyl-6-(trifluoromethyl)benzothiophen-2-yl]propenone was dissolved in MeOH (1.6 mL). 5% Pd—C (13 mg) was added to the solution, and the mixture was stirred for 3 hours under H$_2$ atmosphere. The resulting mixture was filtered through celite, the filtrate was concentrated to dryness. The residue was purified by silica gel column chromatography (chloroform/methanol, 100:1) to give the brown crystal. The crystal was recrystallized from hexane-ethyl acetate, to give the titled compound as a pale yellow crystal (33 mg, yield 51%).

$^1$H-NMR (CDCl$_3$, 400 MHz) δ: 1.01 (3H, t, J=7 Hz), 1.6-1.7 (2H, m), 2.16 (3H, s), 2.82 (2H, t, J=7 Hz), 3.34 (4H, s), 6.35 (1H, s), 7.46 (1H, s), 7.56 (1H, d, J=9 Hz), 7.71 (1H, d, J=9 Hz), 8.04 (1H, s), 12.45 (1H, s).

(4) Ethyl 5-hydroxy-2-methyl-4-[3-[3-propyl-6-(trifluoromethyl)benzothiophen-2-yl]propionyl]phenoxyacetate In acetone (0.8 mL) was suspended 1-(2,4-dihydroxy-5-methylphenyl)-3-[3-propyl-6-(trifluoromethyl)benzothiophen-2-yl]propan-1-one and cesium carbonate (33 mg, 0.788 mmol). After addition of 1-Methyl bromoacetate in acetone (79 µL), the mixture was stirred for 7 hours at room temperature, diluted with ice-water, and extracted with ethyl acetate. The organic layer was washed with brine, and dried over anhydrous sodium sulfate. After the solvent was removed under reduced pressure, and the residue was purified by silica gel column chromatography (hexane/ethyl acetate, 6:1) to give the titled compound as a pale yellow crystal (34 mg, yield 86%).

$^1$H-NMR (CDCl$_3$, 400 MHz) δ: 1.01 (3H, t, J=7 Hz), 1.31 (3H, t, J=7 Hz), 1.6-1.7 (2H, m), 2.19 (3H, s), 2.83 (2H, t, J=7 Hz), 3.34 (4H, s), 4.27 (2H, q, J=7 Hz), 4.66 (2H, s), 6.25 (1H, s), 7.47 (1H, s), 7.56 (1H, d, J=8 Hz), 7.71 (1H, d, J=8 Hz), 8.04 (1H, s), 12.54 (1H, s).

(5) 5-Hydroxy-2-methyl-4-[3-[3-propyl-6-(trifluoromethyl)benzothiophen-2-yl]propionyl]phenoxyacetic acid To a mixture of ethanol (0.2 mL) and water (0.1 mL) was suspended ethyl 5-hydroxy-2-methyl-4-[1-hydroxyimino-3-[3-propyl-6-(trifluoromethyl)-benzothiophen-2-yl]propyl]phenoxyacetate (15 mg, 0.0295 mmol) obtained above. After the addition of lithium hydroxide monohydrate (3.7 mg, 0.0885 mmol), the suspension was heated for 1 hour under reflux, and then allowed to cool to room temperature and diluted with ice-water. The mixture was acidified by addition of 1M HCl and extracted with ethyl acetate. The organic layer was washed with brine, and dried over anhydrous sodium sulfate. The solvent was removed under reduced pressure, and the residue was recrystallized from ethyl acetate-hexane, to give the titled compound as a pale yellow crystal (9.7 mg, yield 69%).

FAB-MS (m/e): 481 (M+1)

$^1$H-NMR (CDCl$_3$, 400 MHz) δ: 1.00 (3H, t, J=7 Hz), 1.6-1.7 (2H, m), 2.19 (3H, s), 2.83 (2H, t, J=7 Hz), 3.35 (4H, s), 4.73 (2H, s), 6.29 (1H, s), 7.48 (1H, s), 7.56 (1H, d, J=8 Hz), 7.72 (1H, d, J=8 Hz), 8.03 (1H, s), 12.53 (1H, s).

IR (KBr, cm$^{-1}$): 2964, 2929, 2870, 2584, 2359, 1751, 1637, 1574, 1498, 1460, 1427, 1375, 1327, 1279, 1238, 1215, 1159, 1115, 1082, 1049, 980, 910, 883, 814, 762, 719, 685, 652.

Example 23

5-Hydroxy-4-[1-hydroxyimino-3-[3-propyl-6-(trifluoromethyl)benzothiophen-2-yl]propyl]-2-methylphenoxyacetic acid (1) Ethyl 5-hydroxy-4-[1-hydroxyimino-3-[3-propyl-6-(trifluoromethyl)-benzothiophen-2-yl]propyl]-2-methylphenoxyacetate To a solution of Ethyl 5-hydroxy-2-methyl-4-[3-[3-propyl-6-(trifluoromethyl)benzothiophen-2-yl]propionyl]-phenoxyacetate (obtained in Example 22-(4), 19 mg, 0.0381 mmol) in EtOH (0.4 mL) was added hydroxylamine hydrochloride (2.9 mg, 0.0419 mmol) and sodium acetate (3.8 mg, 0.0457 mmol) in water (0.3 mL). The mixture was heated for 10 hours under reflux and cooled to room temperature, diluted with water, and extracted with ethyl acetate. The organic layer was washed with brine, dried over anhydrous sodium sulfate. The solvent was removed under reduced pressure, and the residue was recrystallized from chloroform-hexane, to give the titled compound as a white crystal (7.5 mg, yield 38%).

$^1$H-NMR (CDCl$_3$, 400 MHz) δ: 0.99 (3H, t, J=7 Hz), 1.31 (3H, t, J=7 Hz), 1.6-1.7 (2H, m), 2.19 (3H, s), 2.80 (2H, t, J=7 Hz), 3.19 (4H, s), 4.27 (2H, q, J=7 Hz), 4.64 (2H, s), 6.34 (1H, s), 6.97 (1H, s), 7.15 (1H, s), 7.56 (1H, d, J=9 Hz), 7.72 (1H, d, J=9 Hz), 8.06 (1H, s), 11.04 (1H, br s).

(2) 5-Hydroxy-4-[1-hydroxyimino-3-[3-propyl-6-(trifluoromethyl)-benzothiophen-2-yl]propyl]-2-methylphenoxyacetic acid To a mixture of EtOH (0.2 mL) and H$_2$O (0.1 mL) was suspended ethyl 5-hydroxy-4-[1-hydroxyimino-3-[3-propyl-6-(trifluoromethyl)-benzothiophen-2-yl]propyl]-2-methylphenoxyacetate (7.5 mg, 0.0143 mmol) obtained above. After the addition of lithium hydroxide monohydrate (1.8 mg, 0.0429 mmol), the mixture was heated for 1 hour under reflux, and then allowed to cool to room temperature and added ice-water. The mixture was acidified by addition of 1M HCl, and extracted with ethyl acetate. The organic layer was washed with brine, and dried over anhydrous sodium sulfate. The solvent was removed under reduced pressure to give the title compound (8.0 mg, yield>99%) as a brown crystal.

FAB-MS (m/e): 496 (M+1)

$^1$H-NMR (CD$_3$OD, 400 MHz) δ: 1.00 (3H, t, J=7 Hz), 1.6-1.7 (2H, m), 2.07 (3H, s), 2.82 (2H, t, J=7 Hz), 3.19 (4H, s), 4.63 (2H, s), 6.31 (1H, s), 7.35 (2H, d, J=8 Hz), 7.10 (1H, s), 7.57 (1H, d, J=8 Hz), 7.80 (1H, d, J=8 Hz), 8.12 (1H, s).

IR (KBr, cm$^{-1}$): 2958, 2931, 2871, 2353, 2322, 1732, 1628, 1581, 1504, 1404, 1350, 1325, 1267, 1194, 1171, 1153, 1117, 1080, 1057, 976, 941, 879, 818, 769, 719, 667.

Example 24

N-[5-Methyl-3-[2-[3-propyl-6-(trifluoromethyl)benzothiophen-2-yl]ethyl]benzisoxazol-6-yl]-N-methylglycine The following compounds were obtained by the similar manner as described in Example 19 and 20.

(1) N-[5-Methyl-3-[2-[3-propyl-6-(trifluoromethyl)benzothiophen-2-yl]ethyl]benzisoxazol-6-yl]acetamide Pale yellow crystal
Yield: 38%

$^1$H-NMR (CDCl$_3$, 400 MHz) δ: 0.94 (3H, t, J=7 Hz), 1.5-1.6 (2H, m), 2.22 (3H, s), 2.26 (3H, s), 2.67 (2H, t, J=7 Hz), 3.2-3.5 (4H, m), 7.09 (1H, br s), 7.16 (1H, s), 7.55 (1H, d, J=8 Hz), 7.67 (1H, d, J=8 Hz), 8.06 (1H, s), 8.40 (1H, br s).

(2) N-Methyl-N-[5-methyl-3-[2-[3-propyl-6-(trifluoromethyl)benzothiophen-2-yl]ethyl]benzisoxazol-6-yl]-acetamide Pale yellow crystal
Yield: 99%

$^1$H-NMR (CDCl$_3$, 400 MHz) δ: 0.95 (3H, t, J=7 Hz), 1.5-1.6 (2H, m), 1.75 (3H, s), 2.19 (3H, s), 2.68 (2H, t, J=7 Hz), 3.20 (3H, s), 3.3-3.4 (2H, m), 3.4-3.5 (2H, m), 7.35 (2H, d, J=8 Hz), 7.55 (1H, d, J=8 Hz), 7.67 (1H, d, J=8 Hz), 8.06 (1H, s).

(3) 5-Methyl-6-methylamino-3-[2-[3-propyl-6-(trifluoromethyl)benzothiophen-2-yl]ethyl]benzisoxazole Purple crystal
Yield: 82%

$^1$H-NMR (CDCl$_3$, 400 MHz) δ: 0.95 (3H, t, J=7 Hz), 1.5-1.6 (2H, m), 2.10 (3H, s), 2.72 (2H, t, J=7 Hz), 2.95 (3H, d, J=3 Hz), 3.2-3.5 (4H, m), 4.02 (1H, br s), 6.60 (1H, s), 7.05 (1H, s), 7.54 (1H, d, J=9 Hz), 7.68 (1H, d, J=9 Hz), 8.05 (1H, s).

(4) N-[5-Methyl-3-[2-[3-propyl-6-(trifluoromethyl)benzothiophen-2-yl]ethyl]benzisoxazol-6-yl]-N-methylglycine ethyl ester Pale orange crystal
Yield: 78%
$^1$H-NMR (CDCl$_3$, 400 MHz) δ: 0.95 (3H, t, J=7 Hz), 1.26 (3H, t, J=7 Hz), 1.5-1.6 (2H, m), 2.28 (3H, s), 2.70 (2H, t, J=7 Hz), 2.94 (3H, s), 3.1-3.5 (4H, m), 3.78 (2H, s), 4.1-4.2 (2H, m), 7.20 (2H, s), 7.55 (1H, d, J=9 Hz), 7.68 (1H, d, J=9 Hz), 8.05 (1H, s).

(5) N-[5-Methyl-3-[2-[3-propyl-6-(trifluoromethyl)benzothiophen-2-yl]ethyl]benzisoxazol-6-yl]-N-methylglycine Pale yellow crystal
Mp: 147-149° C.
Yield: 88%
FAB-MS (m/e): 491 (M+1)
$^1$H-NMR (CDCl$_3$, 400 MHz) δ: 0.95 (3H, t, J=7 Hz), 1.5-1.6 (2H, m), 2.30 (3H, s), 2.70 (2H, t, J=7 Hz), 2.92 (3H, s), 3.3-3.5 (4H, m), 3.80 (2H, s), 7.24 (2H, d, J=8 Hz), 7.56 (1H, d, J=8 Hz), 7.69 (1H, d, J=8 Hz), 8.06 (1H, s).
IR (KBr, cm$^{-1}$): 2958, 2931, 2873, 1738, 1622, 1516, 1489, 1466, 1441, 1406, 1369, 1322, 1257, 1171, 1105, 1078, 1061, 991, 943, 876, 845, 822, 793, 719, 702, 669, 656.

Example 25

[5-Methyl-3-[2-[3-propyl-6-(trifluoromethyl)benzothiophen-2-yl]ethyl]benzisoxazol-6-yloxy]acetic acid The following compounds were obtained by the similar manner as described in Example 19.

(1) 6-Amino-5-methyl-3-[2-[3-propyl-6-(trifluoromethyl)-benzothiophen-2-yl]ethyl]benzisoxazole Orange crystal
Yield: 87%
$^1$H-NMR (CDCl$_3$, 400 MHz) δ: 0.95 (3H, t, J=8 Hz), 1.5-1.6 (2H, m), 2.14 (3H, s), 2.71 (2H, t, J=7 Hz), 3.2-3.5 (4H, m), 3.99 (2H, s), 6.75 (1H, s), 7.08 (1H, s), 7.55 (1H, d, J=8 Hz), 7.68 (1H, d, J=8 Hz), 8.05 (1H, s).

(2) 6-Hydroxy-5-methyl-3-[2-[3-propyl-6-(trifluoromethyl)benzothiophen-2-yl]ethyl]benzisoxazole Orange crystal
Yield: 16%
$^1$H-NMR (CDCl$_3$, 400 MHz) δ: 0.95 (3H, t, J=7 Hz), 1.5-1.6 (2H, m), 2.23 (3H, s), 2.70 (2H, t, J=7 Hz), 3.2-3.5 (4H, m), 5.35 (1H, s), 6.93 (1H, s), 7.16 (1H, s), 7.55 (1H, d, J=9 Hz), 7.68 (1H, d, J=9 Hz), 8.05 (1H, s).

(3) Ethyl [5-methyl-3-[2-[3-propyl-6-(trifluoromethyl)-benzothiophen-2-yl]ethyl]benzisoxazol-6-yloxy]acetate Pale yellow crystal
Yield: 68%
$^1$H-NMR (CDCl$_3$, 400 MHz) δ: 0.95 (3H, t, J=8 Hz), 1.31 (3H, t, J=7 Hz), 1.5-1.6 (2H, m), 2.27 (3H, s), 2.72 (2H, t, J=7 Hz), 3.2-3.5 (4H, m), 4.28 (2H, q, J=7 Hz), 4.71 (2H, s), 6.82 (1H, s), 7.20 (1H, s), 7.55 (1H, d, J=8 Hz), 7.69 (1H, d, J=8 Hz), 8.05 (1H, s).

(4) [5-Methyl-3-[2-[3-propyl-6-(trifluoromethyl)benzothiophen-2-yl]ethyl]benzisoxazol-6-yloxy]acetic acid Pale yellow crystal
Yield: 99%
FAB-MS (m/e): 478 (M+1)
$^1$H-NMR (CDCl$_3$, 400 MHz) δ: 0.95 (3H, t, J=7 Hz), 1.5-1.6 (2H, m), 2.26 (3H, s), 2.70 (2H, t, J=7 Hz), 3.2-3.5 (4H, m), 4.78 (2H, s), 6.87 (1H, s), 7.20 (1H, s), 7.55 (1H, d, J=8 Hz), 7.69 (1H, d, J=8 Hz), 8.05 (1H, s).

Example 26

3-[5-Methyl-3-[2-[3-propyl-6-(trifluoromethyl)benzothiophen-2-yl]ethyl]benzisoxazol-6-yl]propionic acid The following compounds were obtained by the similar manner as described in Example 21.

(1) Methyl 2-bromo-3-[5-methyl-3-[2-[3-propyl-6-(trifluoromethyl)benzothiophen-2-yl]ethyl]benzisoxazol-6-yl]propionate Yellow oil
Yield: 70%
$^1$H-NMR (CDCl$_3$, 400 MHz) δ: 0.94 (3H, t, J=7 Hz), 1.5-1.6 (2H, m), 2.32 (3H, s), 2.68 (2H, t, J=7 Hz), 3.3-3.6 (6H, m), 3.75 (3H, s), 4.42 (1H, t, J=7 Hz), 7.23 (1H, s), 7.37 (1H, s), 7.55 (1H, d, J=8 Hz), 7.67 (1H, d, J=8 Hz), 8.05 (1H, s).

(2) Methyl 3-[5-methyl-3-[2-[3-propyl-6-(trifluoromethyl)benzothiophen-2-yl]ethyl]benzisoxazol-6-yl]acrylate Pale orange crystal
Yield: 94%
$^1$H-NMR (CDCl$_3$, 400 MHz) δ: 0.95 (3H, t, J=7 Hz), 1.5-1.6 (2H, m), 2.40 (3H, s), 2.70 (2H, t, J=7 Hz), 3.3-3.5 (4H, m), 3.84 (3H, s), 6.44 (1H, d, J=16 Hz), 7.25 (1H, s), 7.55 (1H, d, J=9 Hz), 7.68 (1H, d, J=9 Hz), 7.70 (1H, s), 8.00 (1H, d, J=16 Hz), 8.06 (1H, s).

(3) 3-[5-Methyl-3-[2-[3-propyl-6-(trifluoromethyl)benzothiophen-2-yl]ethyl]benzisoxazol-6-yl]acrylic acid Pale yellow crystal
Yield: 97%
$^1$H-NMR (CDCl$_3$, 400 MHz) δ: 0.95 (3H, t, J=7 Hz), 1.5-1.6 (2H, m), 2.41 (3H, s), 2.70 (2H, t, J=8 Hz), 3.3-3.5

(4H, m), 6.47 (1H, d, J=16 Hz), 7.26 (1H, s), 7.55 (1H, d, J=9 Hz), 7.68 (1H, d, J=9 Hz), 7.73 (1H, s), 8.06 (1H, s), 8.07 (1H, d, J=16 Hz).

(4)₃-[5-Methyl-3-[2-[3-propyl-6-(trifluoromethyl)benzothiophen-2-yl]ethyl]benzisoxazol-6-yl]propionic acid Pale yellow crystal
Yield: 72%
FAB-MS (m/e): 476 (M+1)
¹H-NMR (CDCl₃, 400 MHz) δ: 0.94 (3H, t, J=7 Hz), 1.5-1.6 (2H, m), 2.32 (3H, s), 2.70 (2H, t, J=7 Hz), 2.71 (2H, t, J=7 Hz), 3.07 (2H, t, J=7 Hz), 3.3-3.5 (4H, m), 7.24 (1H, s), 7.37 (1H, s), 7.55 (1H, d, J=8 Hz), 7.69 (1H, d, J=8 Hz), 8.05 (1H, s).
IR (KBr, cm⁻¹): 2964, 2929, 2376, 2349, 1705, 1624, 1516, 1518, 1458, 1437, 1406, 1360, 1327, 1257, 1217, 1155, 1113, 1082, 1057, 957, 883, 843, 818, 719, 673, 648.

Example 27

2-[3-[2-[3-Isopropyl-6-(trifluoromethyl)benzothiophen-2-yl]ethyl]benzisoxazol-6-yloxy]propionic acid The following compounds were obtained by the similar manner as described in Example 19.

(1) Ethyl 2-[3-[2-[3-Isopropyl-6-(trifluoromethyl)benzothiophen-2-yl]ethyl]benzisoxazol-6-yloxy]propionate Pale yellow oil
Yield: 26%
¹H-NMR (CDCl₃, 400 MHz) δ: 1.26 (3H, t, J=7 Hz), 1.36 (6H, d, J=7 Hz), 1.68 (3H, d, J=7 Hz), 2.26 (3H, s), 3.1-3.2 (2H, m), 3.3-3.4 (1H, m), 3.4-3.5 (2H, m), 4.22 (2H, q, J=7 Hz), 4.81 (1H, q, J=7 Hz), 6.79 (1H, s), 7.20 (1H, s), 7.52 (1H, d, J=9 Hz), 7.93 (1H, d, J=9 Hz), 8.05 (1H, s).

(2) 2-[3-[2-[3-Isopropyl-6-(trifluoromethyl)benzothiophen-2-yl]ethyl]benzisoxazol-6-yloxy]propionic acid Pale yellow crystal
Yield 98%
Mp: 159-161° C.
FAB-MS (m/e): 492 (M+1)
¹H-NMR (CDCl₃, 400 MHz) δ: 1.35 (6H, d, J=7 Hz), 1.74 (3H, d, J=7 Hz), 2.25 (3H, s), 3.29 (2H, dd, J=6 Hz, 8 Hz), 3.3-3.4 (1H, m), 3.45 (2H, dd, J=6 Hz, 8 Hz), 4.88 (1H, q, J=7 Hz), 6.85 (1H, s), 7.21 (1H, s), 7.52 (1H, d, J=8 Hz), 7.92 (1H, d, J=8 Hz), 8.04 (1H, s).
IR (KBr, cm⁻¹): 2964, 2927, 2854, 2359, 1726, 1622, 1604, 1518, 1448, 1375, 1329, 1300, 1275, 1244, 1151, 1119, 1082, 1045, 1003, 931, 881, 814, 721, 673.

Example 28

N-[3-[2-[3-Isopropyl-6-(trifluoromethyl)benzothiophen-2-yl]ethyl]benzisoxazol-6-yl]-N-methylglycine The following compounds were obtained by the similar manner as described in Example 19.

(1) N-[3-[2-[3-Isopropyl-6-(trifluoromethyl)benzothiophen-2-yl]ethyl]benzisoxazol-6-yl]acetamide Pale yellow crystal
Yield: 37%
¹H-NMR (CD₃OD, 400 MHz) δ: 1.28 (6H, d, J=7 Hz), 2.15 (3H, s), 3.3-3.4 (1H, m), 3.37 (2H, t, J=7 Hz), 3.49 (2H, t, J=7 Hz), 7.24 (1H, dd, J=1 Hz, 8 Hz), 7.52 (1H, dd, J=1 Hz, 8 Hz), 7.55 (1H, dd, J=8 Hz), 8.00 (1H, d, J=8 Hz), 8.10 (2H, s).

(2) N-[3-[2-[3-Isopropyl-6-(trifluoromethyl)benzothiophen-2-yl]ethyl]benzisoxazol-6-yl]-N-methylacetamide Yellow oil
Yield: 66%
¹H-NMR (CDCl₃, 400 MHz) δ: 1.37 (6H, d, J=7 Hz), 1.91 (3H, br s), 3.32 (3H, s), 3.3-3.4 (1H, m), 3.39 (2H, dd, J=6, 7 Hz), 3.51 (2H, dd, J=6, 7 Hz), 7.12 (1H, d, J=8 Hz), 7.42 (1H, d, J=1 Hz), 7.52 (1H, dd, J=1, 8 Hz), 7.57 (1H, d, J=8 Hz), 7.93 (1H, d, J=8 Hz), 8.04 (1H, s).

(3) 3-[2-[3-Isopropyl-6-(trifluoromethyl)benzothiophen-2-yl]ethyl]-6-methylaminobenzisoxazole Pale brown crystal
Yield: 85%
¹H-NMR (CDCl₃, 400 MHz) δ: 1.37 (6H, d, J=7 Hz), 2.90 (3H, s), 3.26 (2H, dd, J=7 Hz, 8 Hz), 3.3-3.4 (1H, m), 3.44 (2H, dd, J=7 Hz, 8 Hz), 4.17 (1H, br s), 6.52 (1H, dd, J=2, 9 Hz), 6.57 (1H, d, J=2 Hz), 7.23 (1H, d, J=9 Hz), 7.51 (1H, d, J=9 Hz), 7.92 (1H, d, J=9 Hz), 8.04 (1H, s).

(4) N-[3-[2-[3-Isopropyl-6-(trifluoromethyl)benzothiophen-2-yl]ethyl]-N-methylglycine ethyl ester Pale yellow crystal
Yield: 74%
¹H-NMR (CDCl₃, 400 MHz) δ: 1.25 (3H, t, J=7 Hz), 1.38 (6H, d, J=7 Hz), 3.15 (3H, s), 3.27 (2H, dd, J=7 Hz, 8 Hz), 3.3-3.4 (1H, m), 3.45 (2H, dd, J=7 Hz, 8 Hz), 4.13 (2H, s), 4.19 (2H, q, J=7 Hz), 6.66 (1H, dd, J=1 Hz, 9 Hz), 6.69 (1H, d, J=1 Hz), 7.34 (1H, d, J=9 Hz), 7.52 (1H, d, J=9 Hz), 7.93 (1H, d, J=9 Hz), 8.04 (1H, s).

(5) N-[3-[2-[3-Isopropyl-6-(trifluoromethyl)benzothiophen-2-yl]ethyl]-N-methylglycine Pale yellow crystal
Mp: 153-156° C.
Yield: 96%
FAB-MS (m/e): 477 (M+1)
¹H-NMR (CDCl₃, 400 MHz) δ: 1.38 (6H, d, J=7 Hz), 3.15 (3H, s), 3.25 (2H, dd, J=7, 8 Hz), 3.3-3.4 (1H, m), 3.45 (2H, dd, J=7, 8 Hz), 4.19 (2H, s), 6.67 (1H, dd, J=1, 9 Hz), 6.71 (1H, d, J=1 Hz), 7.36 (1H, d, J=9 Hz), 7.51 (1H, d, J=9 Hz), 7.92 (1H, d, J=9 Hz), 8.03 (1H, s).
IR (KBr, cm⁻¹): 2972, 2871, 2395, 2350, 1747, 1626, 1520, 1477, 1404, 1371, 1327, 1259, 1246, 1211, 1178, 1161, 1113, 1080, 1059, 976, 955, 881, 817, 723, 642, 615.

Example 29

Pharmacological Experimentals

I. Procedures of Experimental
Transfection

The PPAR activating effects of test compounds were measured by the following method.

A receptor expression plasmid (pSG5-GAL4-hPPAR α or γ or δ LBD), a luciferase expression plasmid (pUC8-MH100× 4-TK-Luc) and β-galactosidase (pCMX-β-GAL) expression plasmid (Kliewer, S. A., et. al., (1992) Nature, 358: 771-774) are transfected into CV-1 cells (ATCC), American type culture collection)). Subsequently, it is incubated for approximately 40 hours in the presence of the test compound. Then, the luciferase activity and β-GAL activity are measured on the soluble cells. The luciferase activity is calibrated by the β-GAL activity. A relative ligand activity is calculated in consideration of a luciferase activity (assigned to 100%) of cells treated with GW-590735 (PPAR α-selective agonist), Rosiglitazone (PPAR γ selective agonist), or GW-501516 (PPAR δ selective agonist).

Experimental Results

TABLE 24

| Test compound | PPAR activity | | |
|---|---|---|---|
| | α | γ | δ |
| Example 3 | Inactive | Inactive | 4.4% |
| Example 4 | 2.6% | 9.0% | 19.2% |
| Example 5 | Inactive | Inactive | 23.0% |
| Example 6 | Inactive | Inactive | 40.8% |
| Example 7 | Inactive | Inactive | 51.4% |
| Example 8 | Inactive | Inactive | 81.0% |
| Example 9 | Inactive | 1.3% | 83.5% |
| Example 10 | Inactive | 2.2% | 66.1% |
| Example 11 | Inactive | Inactive | 60.9% |
| Example 12 | Inactive | Inactive | 87.3% |
| Example 13 | Inactive | Inactive | 90.4% |
| Example 14 | Inactive | Inactive | 73.0% |
| Example 15 | Inactive | Inactive | 77.4% |
| Example 16 | Inactive | Inactive | 51.7% |
| Example 17 | Inactive | Inactive | 45.9% |
| Example 19 | Inactive | Inactive | 91.7% |
| Example 20 | 1.1% | Inactive | 88.0% |
| Example 21 | Inactive | Inactive | 94.2% |

PPAR activity: relative value (%) of the test compound to 100% of the control compound is calculated, and the activity is shown as $EC_{50}$ (μM), that is, the concentration of the test compound giving 50% of the relative value.
α: GW-590735=$10^{-6}$ M
γ: Rosiglitazone=$10^{-5}$ M
δ: GW-501516=$10^{-7}$ M As is clear from Table 24, the compounds of the invention show an excellent PPAR δ activating effect.

Example 30

Pharmacological Experimentals

Procedures of Experimental

The PPAR activating effect ($EC_{50}$ (μM)) was measured on the compounds of Example 19, 21 and GW-501516 by the method described in Example 29.

TABLE 25

| Test compound | PPAR activity ($EC_{50}$ (μM)) | | |
|---|---|---|---|
| | α | γ | δ |
| Example 19 | >10 | >10 | 0.0048 |
| Example 21 | >10 | >10 | 0.0013 |
| GW-501516 | 0.88 | 3.9 | 0.0013 |

As is clear from Table 25, the compounds of Example 19 and 21 according to the invention show a selectivity of PPAR δ-activating effect superior to that of the GW-501516.

Example 31

The PPAR activating effect was measured on the compound of Examples by the method described in Example 29.

Experimental Results

TABLE 26

| Test compound | PPAR activity | | |
|---|---|---|---|
| | α | γ | δ |
| Example 22 | Inactive | Inactive | 70.9% |
| Example 23 | Inactive | Inactive | 5.1% |
| Example 24 | 16.4% | 5.8% | 77.2% |
| Example 25 | Inactive | Inactive | 87.4% |
| Example 26 | Inactive | Inactive | 88.8% |
| Example 27 | Inactive | Inactive | 63.7% |
| Example 28 | Inactive | Inactive | 81.3% |

PPAR activity: relative value (%) of the test compound ($10^{-7}$ M) to 100% of the control compound
α: GW-590735—$10^{-6}$ M
γ: Rosiglitazone—$10^{-5}$ M
δ: GW-501516—$10^{-7}$ M As is clear from Table 26, the compound of Example 22-28 according to the invention shows an excellent PPAR δ activating effect.

The invention claimed is:

1. A compound having the following formula (I) or a pharmacologically acceptable salt thereof:

$$R^1\text{-}\underset{X}{\text{[ring]}}\text{-}R^2\text{-}\underset{R^4}{\overset{R^3}{(C)_m}}\text{-}\underset{A}{\overset{\|}{(C)_p}}\text{-}B\text{-}Y\text{-}\underset{R^6}{\overset{R^5}{(C)_n}}\text{-}CO_2H \quad (I)$$

wherein:
$R^1$ is hydrogen, halogen, hydroxyl, nitro, amino, cyano, carboxyl, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, a heterocyclic group of five-membered or six-membered ring, aralkyl consisting of $C_{6-10}$ aryl and $C_{1-8}$ alkylene, or $C_{1-8}$ alkyl substituted with a heterocyclic group of five-membered or six-membered ring;
$R^2$ is hydrogen, $C_{1-8}$ alkyl, $C_{2-8}$ alkenyl, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{2-8}$ acyl, $C_{6-10}$ aryl, or aralkyl consisting of $C_{6-10}$ aryl and $C_{1-8}$ alkylene;

each of $R^3$, $R^4$, $R^5$, and $R^6$ independently is hydrogen, $C_{1-8}$ alkyl, or $C_{1-8}$ alkyl substituted with halogen;

X is sulfur;

Y is a bond:

p is 0 or 1:

A is oxygen, $CH_2$, N—$NH_2$ or N—$OR^9$, wherein $R^9$ is hydrogen, $C_{1-8}$ alkyl, $C_{1-8}$ alkyl substituted with halogen, $C_{2-8}$ acyl, $C_{2-8}$ alkenyl, or aralkyl consisting of $C_{6-10}$ aryl and $C_{1-8}$ alkylene;

when p is 1, B is phenyl, which can have a substituent selected from the group consisting of halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene;

when p is 0, B is a condensed ring selected from the group consisting of indole, benzofuran, benzisoxazole, or 1,2-benzisothiazole, each of which can have a substituent selected from the group consisting of halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene, wherein Y binds to the benzene ring of B, and —$(C(R^3)(R^4))$m- binds to the condensed ring at the 3-position of B;

m is an integer of 1 to 4;

n is an integer of 0 to 5; and when n is 0, Y is a bond.

2. A compound having the following formula (II) or a pharmacologically acceptable salt thereof:

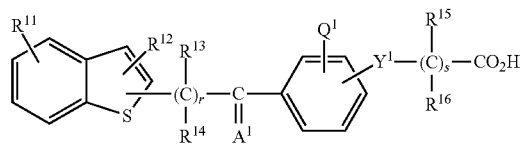

(II)

wherein:
$R^{11}$ is hydrogen, halogen, hydroxyl, nitro, amino, cyano, carboxyl, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, a heterocyclic group of five-membered or six-membered ring, aralkyl consisting of $C_{6-10}$ aryl and $C_{1-8}$ alkylene, or $C_{1-8}$ alkyl substituted with a heterocyclic group of five-membered or six-membered ring;

$R^{12}$ is hydrogen, $C_{1-8}$ alkyl, $C_{2-8}$ alkenyl, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{2-8}$ acyl, $C_{6-10}$ aryl, or aralkyl consisting of $C_{6-10}$ aryl and $C_{1-8}$ alkylene;

each of $R^{13}$, $R^{14}$, $R^{15}$, and $R^{16}$ independently is hydrogen, $C_{1-8}$ alkyl, or $C_{1-8}$ alkyl substituted with halogen;

$Y^1$ is a bond;

$A^1$ is oxygen, $CH_2$, N—$NH_2$, or N—$OR^{19}$, wherein $R^{19}$ is hydrogen, $C_1$ alkyl, $C_{1-8}$ alkyl substituted with halogen, $C_{2-8}$ acyl, $C_{2-8}$ alkenyl, or aralkyl consisting of $C_{6-10}$ aryl and $C_{1-8}$ alkylene;

$Q^1$ is hydrogen, halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene;

r is an integer of 1 to 4; and s is an integer of 1 to 5.

3. The compound or a pharmacologically acceptable salt thereof defined in claim 2, wherein $R^{11}$ is hydrogen, $C_{1-8}$ alkyl, or $C_{1-8}$ alkyl substituted with halogen.

4. The compound or a pharmacologically acceptable salt thereof defined in claim 2, wherein $R^{12}$ is $C_{1-8}$ alkyl or $C_{1-8}$ alkyl substituted with halogen.

5. The compound or a pharmacologically acceptable salt thereof defined in claim 2, wherein each of $R^{13}$ and $R^{14}$ is hydrogen.

6. The compound or a pharmacologically acceptable salt thereof defined in claim 2, wherein each of $R^{15}$ and $R^{16}$ independently is hydrogen or $C_{1-8}$ alkyl.

7. The compound or a pharmacologically acceptable salt thereof defined in claim 2, wherein $A^1$ is oxygen, $CH_2$, N—OH, or N—O-benzyl.

8. The compound or a pharmacologically acceptable salt thereof defined in claim 2, wherein $Q^1$ is $C_{1-8}$ alkyl or $C_{1-8}$ alkyl substituted with halogen.

9. The compound or a pharmacologically acceptable salt thereof defined in claim 2, wherein r is 2.

10. The compound or a pharmacologically acceptable salt thereof defined in claim 2, wherein s is 1 or 2.

11. A compound having the following formula (III) or a pharmacologically acceptable salt thereof:

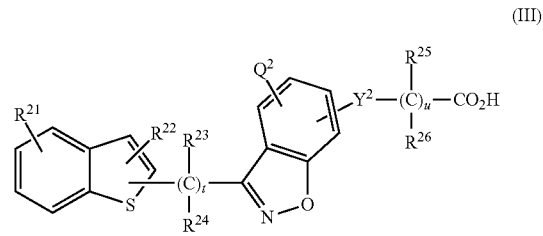

(III)

wherein:
$R^{21}$ is hydrogen, halogen, hydroxyl, nitro, amino, cyano, carboxyl, $C_{1-8}$ alkyl, cycloalkyl of three-membered to seven-membered ring, $C_{2-8}$ alkenyl, alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, a heterocyclic group of five-membered or six-membered ring, aralkyl consisting of $C_{6-10}$ aryl and $C_{1-8}$ alkylene, or $C_{1-8}$ alkyl substituted with a heterocyclic group of five-membered or six-membered ring;

R22 is hydrogen, $C_{1-8}$ alkyl, $C_{2-8}$ alkenyl, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{2-8}$ acyl, $C_{6-10}$ aryl, or aralkyl consisting of $C_{6-10}$ aryl and $C_{1-8}$ alkylene;

each of $R^{23}$, $R^{24}$, $R^{25}$, and $R^{26}$ independently is hydrogen, $C_{1-8}$ alkyl, or $C_{1-8}$ alkyl substituted with halogen;

$Y^2$ is a bond;

$Q^2$ is hydrogen, halogen, hydroxyl, nitro, amino, $C_{1-8}$ alkyl, cycloalkyl of three-membered to seven-membered ring, $C_{2-8}$ alkenyl, $C_{2-8}$ alkynyl, $C_{1-8}$ alkoxy, $C_{1-8}$ alkyl substituted with cycloalkyl of three-membered to seven-membered ring, $C_{1-8}$ alkyl substituted with halogen, $C_{1-8}$ alkyl substituted with $C_{1-8}$ alkoxy, $C_{1-8}$ alkoxy substituted with halogen, $C_{2-8}$ acyl, $C_{6-10}$ aryl, or aralkyl consisting of $C_{6-10}$ aryl and $C_{1-8}$ alkylene;

t is an integer of 1 to 4; and u is an integer of 1 to 5.

12. The compound or a pharmacologically acceptable salt thereof defined in claim 11, wherein $R^{21}$ is hydrogen, $C_{1-8}$ alkyl, or $C_{1-8}$ alkyl substituted with halogen.

13. The compound or a pharmacologically acceptable salt thereof defined in claim 11, wherein $R^{22}$ is $C_{1-8}$ alkyl or $C_{1-8}$ alkyl substituted with halogen.

14. The compound or a pharmacologically acceptable salt thereof defined in claim 11, wherein each of $R^{23}$ and $R^{24}$ is hydrogen.

15. The compound or a pharmacologically acceptable salt thereof defined in claim 11, wherein each of $R^{25}$ and $R^{26}$ independently is hydrogen or $C_{1-8}$ alkyl.

16. The compound or a pharmacologically acceptable salt thereof defined in claim 11, wherein $Q^2$ is $C_{1-8}$ alkyl or $C_{1-8}$ alkyl substituted with halogen.

17. The compound or a pharmacologically acceptable salt thereof defined in claim 11, wherein t is 2.

18. The compound or a pharmacologically acceptable salt thereof defined in claim 12, wherein u is 1 or 2.

19. The compound or a pharmacologically acceptable salt thereof defined in claim 11, wherein the compound is selected from the group consisting of
  3-[4-[3-[3-methyl-6-(trifluoromethyl)benzothiophen-2-yl]propionyl]-2-methylphenyl]propionic acid,
  3-[4-[3-[3-ethyl-6-(trifluoromethyl)benzothiophen-2-yl]propionyl]-2-methylphenyl]propionic acid,
  3-[2-methyl-4-[3-[3-propyl-6-(trifluoromethyl)benzothiophen-2-yl]propionyl]phenyl]propionic acid,
  3-[2-methyl-4-[3-[3-butyl-6-(trifluoromethyl)benzothiophen-2-yl]propionyl]phenyl]propionic acid,
  3-[2-methyl-4-[3-[3-isobutyl-6-(trifluoromethyl)benzothiophen-2-yl]propionyl]phenyl]propionic acid,
  3-[2-methyl-4-[3-[3-isopropyl-6-(trifluoromethyl)benzothiophen-2-yl]propionyl]phenyl]propionic acid,
  3-[4-[1-hydroxyimino-3-[3-isopropyl-6-(trifluoromethyl)benzothiophen-2-yl]propyl]-2-methylphenyl]propionic acid,
  3-[4-[1-[2-[3-isopropyl-6-(trifluoromethyl)benzothiophen-2-yl]ethyl]vinyl]-2-methylphenyl]propionic acid, and
  3-[3-[2-[3-isopropyl-6-(trifluoromethyl)benzothiophen-2-yl]ethyl]-5-methylbenzisoxazol-6-yl]propionic acid.

20. The compound or a pharmacologically acceptable salt thereof defined in claim 1, wherein the compound is 3-[5-methyl-3-[2-[3-propyl-6-(trifluoromethyl)benzothiophen-2-yl]ethyl]benzisoxazol-6-yl]propionic acid.

21. An activator of peroxisome proliferator activated receptor δ which contains as an effective component a compound or a pharmacologically acceptable salt thereof defined in claim 1.

22. A pharmaceutical composition for treatment of a disease mediated by peroxisome proliferator activated receptor δ, which contains as an effective component a compound or a pharmacologically acceptable salt thereof defined in claim 1, and wherein the disease is hyperlipidemia, obesity, atherosclerosis or diabetes.

* * * * *

UNITED STATES PATENT AND TRADEMARK OFFICE
CERTIFICATE OF CORRECTION

PATENT NO.       : 8,648,208 B2                              Page 1 of 1
APPLICATION NO.  : 12/937986
DATED            : February 11, 2014
INVENTOR(S)      : Sakuma et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 108 days.

Signed and Sealed this

Twenty-ninth Day of September, 2015

Michelle K. Lee
*Director of the United States Patent and Trademark Office*